US009814885B2

(12) United States Patent
Molnar et al.

(10) Patent No.: US 9,814,885 B2
(45) Date of Patent: Nov. 14, 2017

(54) STIMULATION ELECTRODE SELECTION

(75) Inventors: Gabriela C. Molnar, Fridley, MN (US); Steven M. Goetz, North Oaks, MN (US); Andrew N. Csavoy, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 2148 days.

(21) Appl. No.: 12/768,403

(22) Filed: Apr. 27, 2010

(65) Prior Publication Data

US 2011/0264165 A1 Oct. 27, 2011

(51) Int. Cl.
  *A61N 1/36* (2006.01)
  *A61N 1/05* (2006.01)
  *A61N 1/08* (2006.01)
  *A61N 1/372* (2006.01)

(52) U.S. Cl.
  CPC ....... *A61N 1/36185* (2013.01); *A61N 1/0529* (2013.01); *A61N 1/08* (2013.01); *A61N 1/37247* (2013.01)

(58) Field of Classification Search
  CPC .......... A61N 1/08; A61N 1/36; A61N 1/3605; A61N 1/3606; A61N 1/36082; A61N 1/36185; A61N 1/37247; A61N 1/0529
  USPC ............................................. 607/45, 46, 62
  See application file for complete search history.

(56) References Cited

U.S. PATENT DOCUMENTS

| | | | |
|---|---|---|---|
| 3,069,654 A | 12/1962 | Hough | |
| 5,241,472 A | 8/1993 | Gur et al. | |
| 5,722,999 A | 3/1998 | Snell | |
| 6,026,142 A | 2/2000 | Gueziec et al. | |
| 6,066,163 A | 5/2000 | John | |

(Continued)

FOREIGN PATENT DOCUMENTS

| AU | 709374 B2 | 12/1997 |
|---|---|---|
| CN | 101918855 | 12/2010 |

(Continued)

OTHER PUBLICATIONS

International Search Report and Written Opinion for corresponding PCT Application No. PCT/US2011/027060, dated May 3, 2011 (10 pgs.).

(Continued)

*Primary Examiner* — Michael Carey
*Assistant Examiner* — Pamela M Bays
(74) *Attorney, Agent, or Firm* — Shumaker & Sieffert, P.A.

(57) ABSTRACT

One or more stimulation electrodes may be selected based on a bioelectrical signal sensed in a brain of a patient with a sense electrode combination that comprises at least one electrode and a physiological model that indicates one or more anatomical structures of the brain of the patient that are proximate the implanted at least one electrode. In some examples, the bioelectrical brain signal indicates which electrodes are located closest to a target tissue site. The physiological model can be generated based on a location of implanted at least one electrode within a patient and patient anatomy data, which can, for example, indicate one or more characteristics of patient tissue proximate to the implanted at least one electrode. In some example, the physiological model includes a therapy field model that represents a region of the tissue of the patient to which therapy is delivered via a selected set of electrodes.

34 Claims, 24 Drawing Sheets

(56) References Cited

U.S. PATENT DOCUMENTS

| | | | |
|---|---|---|---|
| 6,068,652 A | 5/2000 | Cohen et al. | |
| 6,358,245 B1 | 3/2002 | Edwards et al. | |
| 6,373,918 B1 | 4/2002 | Wiemker et al. | |
| 6,393,325 B1 | 5/2002 | Mann et al. | |
| 6,625,482 B1 | 9/2003 | Panescu et al. | |
| 6,697,664 B2 | 2/2004 | Kienzle III et al. | |
| 6,993,384 B2 | 1/2006 | Bradley et al. | |
| 7,044,942 B2 | 5/2006 | Jolly et al. | |
| 7,239,920 B1 | 7/2007 | Thacker et al. | |
| 7,239,926 B2 | 7/2007 | Goetz | |
| 7,283,867 B2 | 10/2007 | Strother et al. | |
| 7,346,382 B2 | 3/2008 | McIntyre et al. | |
| 7,385,443 B1 | 6/2008 | Denison | |
| 7,477,723 B2 | 1/2009 | Kamegawa et al. | |
| 7,505,809 B2 | 3/2009 | Strommer et al. | |
| 7,519,431 B2 | 4/2009 | Goetz et al. | |
| 7,567,834 B2 | 7/2009 | Clayton et al. | |
| 7,623,918 B2 | 11/2009 | Goetz | |
| 7,831,307 B1 | 11/2010 | Moffitt | |
| 7,983,757 B2 | 7/2011 | Miyazawa et al. | |
| 8,160,328 B2 | 4/2012 | Goetz et al. | |
| 8,208,993 B2 | 6/2012 | Piferi et al. | |
| 8,288,628 B2 | 10/2012 | Larkins et al. | |
| 8,406,890 B2 | 3/2013 | Goetz | |
| 8,744,591 B2 | 6/2014 | Davis et al. | |
| 8,934,986 B2 | 1/2015 | Goetz | |
| 8,996,123 B2 | 3/2015 | Goetz et al. | |
| 2003/0013977 A1 | 1/2003 | Daum | |
| 2003/0139781 A1 | 7/2003 | Bradley et al. | |
| 2004/0088027 A1 | 5/2004 | Burnes et al. | |
| 2004/0098063 A1 | 5/2004 | Goetz | |
| 2004/0210273 A1 | 10/2004 | Wang | |
| 2005/0131474 A1 | 6/2005 | Jenkins et al. | |
| 2005/0150418 A1 | 7/2005 | Bakeev et al. | |
| 2005/0150535 A1 | 7/2005 | Samavedam et al. | |
| 2005/0150734 A1 | 7/2005 | Breier et al. | |
| 2005/0171587 A1 | 8/2005 | Daglow et al. | |
| 2006/0122653 A1 | 6/2006 | Bradley et al. | |
| 2006/0122654 A1 | 6/2006 | Bradley et al. | |
| 2006/0195145 A1 | 8/2006 | Lee et al. | |
| 2006/0217781 A1 | 9/2006 | John | |
| 2007/0066998 A1 | 3/2007 | Hansen et al. | |
| 2007/0106360 A1 | 5/2007 | Gibson et al. | |
| 2007/0129770 A1 | 6/2007 | Younis | |
| 2007/0142888 A1 | 6/2007 | Chavez et al. | |
| 2007/0156136 A1 | 7/2007 | Godara et al. | |
| 2007/0185544 A1 | 8/2007 | Dawant et al. | |
| 2007/0203538 A1 | 8/2007 | Stone et al. | |
| 2007/0203539 A1 | 8/2007 | Stone et al. | |
| 2007/0203541 A1 | 8/2007 | Goetz et al. | |
| 2007/0203543 A1 | 8/2007 | Stone et al. | |
| 2007/0203545 A1 | 8/2007 | Stone et al. | |
| 2007/0203546 A1 | 8/2007 | Stone et al. | |
| 2007/0203583 A1 | 8/2007 | Slone | |
| 2007/0225674 A1 | 9/2007 | Molnar et al. | |
| 2007/0255339 A1 | 11/2007 | Torgerson | |
| 2007/0265489 A1 | 11/2007 | Fowler et al. | |
| 2007/0288064 A1 | 12/2007 | Butson et al. | |
| 2007/0288070 A1 | 12/2007 | Libbus et al. | |
| 2008/0004675 A1 | 1/2008 | King et al. | |
| 2008/0052312 A1 | 2/2008 | Tang et al. | |
| 2008/0070521 A1 | 3/2008 | West et al. | |
| 2008/0079362 A1 | 4/2008 | Kawakami et al. | |
| 2008/0111523 A1 | 5/2008 | Kim | |
| 2008/0154340 A1 | 6/2008 | Goetz et al. | |
| 2008/0154341 A1 | 6/2008 | McIntyre et al. | |
| 2008/0183256 A1 | 7/2008 | Keacher | |
| 2008/0201037 A1 | 8/2008 | Suyama et al. | |
| 2008/0218510 A1 | 9/2008 | Grass et al. | |
| 2008/0269836 A1 | 10/2008 | Foffani et al. | |
| 2008/0288029 A1 | 11/2008 | Healy et al. | |
| 2009/0012416 A1 | 1/2009 | Belalcazar et al. | |
| 2009/0082691 A1 | 3/2009 | Denison et al. | |
| 2009/0083070 A1 | 3/2009 | Giftakis et al. | |
| 2009/0099627 A1 | 4/2009 | Molnar et al. | |
| 2009/0118635 A1 | 5/2009 | Lujan et al. | |
| 2009/0118786 A1 | 5/2009 | Meadows et al. | |
| 2009/0192556 A1 | 7/2009 | Wu et al. | |
| 2009/0196471 A1 | 8/2009 | Goetz et al. | |
| 2009/0196472 A1 | 8/2009 | Goetz et al. | |
| 2009/0198306 A1 | 8/2009 | Goetz et al. | |
| 2009/0228070 A1 | 9/2009 | Goetz et al. | |
| 2009/0234422 A1 | 9/2009 | Goetz et al. | |
| 2009/0276005 A1* | 11/2009 | Pless | 607/46 |
| 2009/0287273 A1 | 11/2009 | Carlton et al. | |
| 2009/0306746 A1 | 12/2009 | Blischak | |
| 2010/0100153 A1 | 4/2010 | Carlson et al. | |
| 2010/0100154 A1 | 4/2010 | Roche | |
| 2010/0135553 A1 | 6/2010 | Joglekar | |
| 2011/0093030 A1 | 4/2011 | Goetz et al. | |
| 2011/0313487 A1 | 12/2011 | Kokones et al. | |

FOREIGN PATENT DOCUMENTS

| | | | |
|---|---|---|---|
| WO | 97/43871 A1 | 11/1997 | |
| WO | 99/37358 A1 | 7/1999 | |
| WO | 01/54579 A1 | 8/2001 | |
| WO | 2001058351 A1 | 8/2001 | |
| WO | WO 2006/110206 A1 | 10/2006 | |
| WO | WO 2006/110690 A1 | 10/2006 | |
| WO | 2007007058 A1 | 1/2007 | |
| WO | 2007112061 A2 | 10/2007 | |
| WO | 2009/042135 A2 | 4/2009 | |
| WO | 2009055127 A1 | 4/2009 | |
| WO | 2009073891 A1 | 6/2009 | |
| WO | 2009134475 A1 | 11/2009 | |
| WO | WO 2009134475 * | 11/2009 | A61N 1/372 |
| WO | 2010030904 A2 | 3/2010 | |
| WO | 2010044989 A2 | 6/2011 | |

OTHER PUBLICATIONS

Office Action dated May 21, 2012 for U.S. Appl. No. 12/639,717, (10 pgs.).

Office Action dated May 21, 2012 for U.S. Appl. No. 12/639,678, (10 pgs.).

Examination Report from counterpart Australian patent application No. 2011245691, dated Feb. 5, 2013, 3 pp.

Responsive Amendment dated Aug. 21, 2012 for U.S. Appl. No. 12/639,717, (27 pgs.).

Responsive Amendment dated Aug. 21, 2012 for U.S. Appl. No. 12/639,678, (29 pgs.).

Office Action from U.S. Appl. No. 12/639,717, dated Sep. 28, 2012, 9 pp.

Office Action from U.S. Appl. No. 12/639,678, dated Oct. 1, 2012, 9 pp.

Response to Office Action dated Feb. 1, 2013, from U.S. Appl. No. 12/639,717, filed Mar. 26, 2013, 3 pp.

Notice of Allowance for U.S. Appl. No. 12/639,717, dated Apr. 22, 2013, 8 pp.

Response to Office Action dated Jan. 30, 2013, from U.S. Appl. No. 12/639,678, filed Mar. 27, 2013, 3 pp.

Notice of Allowance for U.S. Appl. No. 12/639,678, dated Apr. 29, 2013, 8 pp.

Jensen et al., "Information, Energy, and Entropy: Design Principles for Adaptive, Therapeutic Modulation of Neural Circuits," European Patent Office, Downloaded on Dec. 22, 2009, from IEEE Xplore (8 pgs.).

Chen et al., "Intra-operative recordings of local field potentials can help localize the subthalamic nucleus in Parkinson's disease surgery," Exp Neurol, (2005) (8 pgs.).

Debatisse et al., "DBS in STN and macrorecording using electrodes of stimulation: what can be done and where we are?," http://files.chuv.ch/internet-docs/nch/posters/nch_dbs_in_stn.pdf, (Jun. 13-17, 2005) (1 pg.).

Wingeier et al. "Intra-operative STN DBS attenuates the prominent beta rhythm in the STN in Parkinson's disease," Experimental Neurology 197 (2006) pp. 244-251.

(56) References Cited

OTHER PUBLICATIONS

Kühn et al., "High-Frequency Stimulation of the Subthalamic Nucleus Suppresses Oscillatory β Activity in Patients with Parkinson's Disease in Parallel with Improvement in Motor Performance," Journal of Neuroscience, 28(24), Jun. 11, 2008, pp. 6165-6173.

Marceglia et al., "Basal ganglia local field potentials: applications in the development of new deep brain stimulation devices for movement disorders," Expert Rev. Med. Devices 4(5), (2007) pp. 605-614.

Rossi et al., "Subthalamic local field potential oscillations during ongoing deep brain stimulation in Parkinson's disease," Brain Research Bulletin 76 (2008) pp. 512-521.

Yelnik et al., "Localization of stimulating electrodes in patients with Parkinson disease by using a three-dimensional atlas-magnetic resonance imaging coregistration method," J. Neurosurg. vol. 99, (2003) pp. 89-99.

U.S. Appl. No. 12/639,717, filed Dec. 16, 2009 entitled "Stimulation Electrode Selection," by Molnar et al.

U.S. Appl. No. 12/639,678, filed Dec. 16, 2009 entitled "Stimulation Electrode Selection," by Molnar et al.

U.S. Appl. No. 61/105,943, filed Oct. 16, 2008 entitled "Stimulation Electrode Selection," by Carlson et al.

U.S. Appl. No. 12/563,845, filed Sep. 21, 2009 entitled "Stimulation Electrode Selection," by Carlson et al.

U.S. Appl. No. 60/975,372, filed Sep. 29, 2007 entitled "Frequency Selective Monitoring of Physiological Signals," by Jensen et al.

U.S. Appl. No. 61/025,503, filed Feb. 1, 2008 entitled "Frequency Selective Monitoring of Physiological Signals," by Jensen et al.

U.S. Appl. No. 61/083,381, filed Jul. 24, 2008 entitled "Frequency Selective Monitoring of Physiological Signals," by Denison et al.

Response to Office Action dated Sep. 28, 2012, from U.S. Appl. No. 12/639,717, filed Dec. 28, 2012, 28 pp.

Response to Office Action dated Oct. 1, 2012, from U.S. Appl. No. 12/639,678, filed Dec. 28, 2012, 31 pp.

Office Action for U.S. Appl. No. 12/639,717, dated Feb. 1, 2013, 5 pp.

Office Action for U.S. Appl. No. 12/639,678, dated Jan. 30, 2013, 5 pp.

Patel et al., "Overview of Computer-Assisted Image-Guided Surgery of the Spine," Seminars in Spine Surgery, Elsevier, Sep. 30, 2008, pp. 186-194.

Final Office Action, and translation thereof, from Counterpart Japanese Patent Application No. 2013-507957, dated Sep. 16, 2014, 25 pp.

Office Action, and translation thereof, from counterpart Japanese Application No. 2013-507957, dated May 18, 2015, 5 pp.

Freeman et al. "Determining the Minimum-Area Encasing Rectangle for an Arbitrary Closed Curve," Communications of the ACM, vol. 18, No. 7, Jul. 1975, pp. 409-413.

Lindeberg, "Detecting Salient Blob-Like Image Structures and Their Scales with a Scale-Space Primal Sketch: A Method for Focus-of-Attention," International Journal of Computer Vision, vol. 11, No. 3, Dec. 1993, pp. 283-318.

Lowe, "Distinctive Image Features from Scale-Invariant Keypoints," International Journal of Computer Vision, vol. 60, No. 2, Jan. 22, 2004, pp. 91-110.

McIntyre et al., "Electric Field and Stimulating Influence Generated by Deep Brain Stimulation of the Subthalamic Nucleus," Clinical Neurophsyiology, vol. 115, Mar. 2004, pp. 589-595.

Summonds to Attend Oral Proceedings pursuant to Rule 115(1) EPC dated Nov. 30, 2016 from counterpart European Application No. 11709246.0, 5 pp.

Response to Summonds to Attend Oral Proceedings pursuant to Rule 115(1) EPC dated Nov. 30, 2016, from counterpart European Application No. 11709246.0, filed Mar. 20, 2017, 9 pp.

Auxiliary Request from European Application No. 11709246.0, filed Apr. 18, 2017, 8 pp.

Notice of the Second Office Action, and translation thereof, from Counterpart Chinese Patent Application No. 201180032077.1, dated Oct. 31, 2014, 19 pp.

Third Office Action and translation thereof, from counterpart Chinese Application No. 201180032077.1, dated Jun. 20, 2015, 11 pp.

First Office Action and Search Report, and translation thereof, from Counterpart Chinese Application No. 201180032077.1, dated Apr. 10, 2014, 21 pp.

Decision to refuse a European Patent Application from counterpart European Application No. 11709246.0, dated May 29, 2017, 15 pp.

\* cited by examiner

STIMULATION ELECTRODE SELECTION

The disclosure relates to medical devices, and, more particularly, to medical device programming.

BACKGROUND

Implantable medical devices, such as electrical stimulators, may be used in different therapeutic applications. In some therapy systems, an implantable electrical stimulator delivers electrical therapy to a target tissue site within a patient with the aid of one or more medical leads that include electrodes. During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may include the configuration of electrodes used to deliver the electrical stimulation therapy.

SUMMARY

In general, the disclosure is directed to selecting one or more electrodes from an array of electrodes for delivering electrical stimulation to a brain of a patient. A group of one or more selected electrodes used to deliver stimulation may be referred to as a stimulation electrode combination. In examples described herein, the stimulation electrode combination may be selected based on a bioelectrical signal sensed in a brain of a patient with a sense electrode combination that comprises at least one electrode (e.g., on a lead or medical device housing) and a physiological model that indicates one or more characteristics of tissue proximate the electrode within the brain of the patient. For example, the physiological model can indicate one or more anatomical structures of the brain of the patient that are proximate the implanted lead or can include a therapy field model that indicates a therapy field that results, or is expected to result, from stimulation delivered via the stimulation electrode combination.

In one aspect, the disclosure is directed to a method comprising sensing a bioelectrical signal in a brain of a patient with a sense electrode combination that comprises at least one electrode, accessing a physiological model that indicates one or more characteristics of tissue proximate the at least one electrode within the brain of the patient, and selecting a stimulation electrode combination for delivering electrical stimulation to the brain of the patient based on the bioelectrical signal and the physiological model.

In another aspect, the disclosure is directed to a system comprising a sensing module that senses a bioelectrical signal in a brain of a patient with a sense electrode combination that comprises at least one electrode and a processor that accesses a physiological model that indicates one or more characteristics of tissue proximate the at least one electrode within the brain of the patient and selects a stimulation electrode combination for delivering electrical stimulation to the brain of the patient based on the bioelectrical signal and the physiological model.

In another aspect, the disclosure is directed to a system comprising means for sensing a bioelectrical signal in a brain of a patient with a sense electrode combination that comprises at least one electrode, and means for selecting a stimulation electrode combination for delivering electrical stimulation to the brain of the patient based on the bioelectrical signal and a physiological model that indicates one or more characteristics of tissue proximate the at least one electrode within the brain of the patient.

In another aspect, the disclosure is directed to a computer-readable medium comprising instructions that cause a programmable processor to receive, from a sensing module, a bioelectrical signal sensed by the sensing module in a brain of a patient with a sense electrode combination that comprises at least one electrode, access a physiological model that indicates one or more characteristics of tissue proximate the at least one electrode within the brain of the patient, and select a stimulation electrode combination for delivering electrical stimulation to the brain of the patient based on the bioelectrical signal and the physiological model.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

The details of one or more examples of the invention are set forth in the accompanying drawings and the description below. Other features, objects, and advantages of the invention will be apparent from the description and drawings, and from the claims.

DETAILED DESCRIPTION

Figure 1:
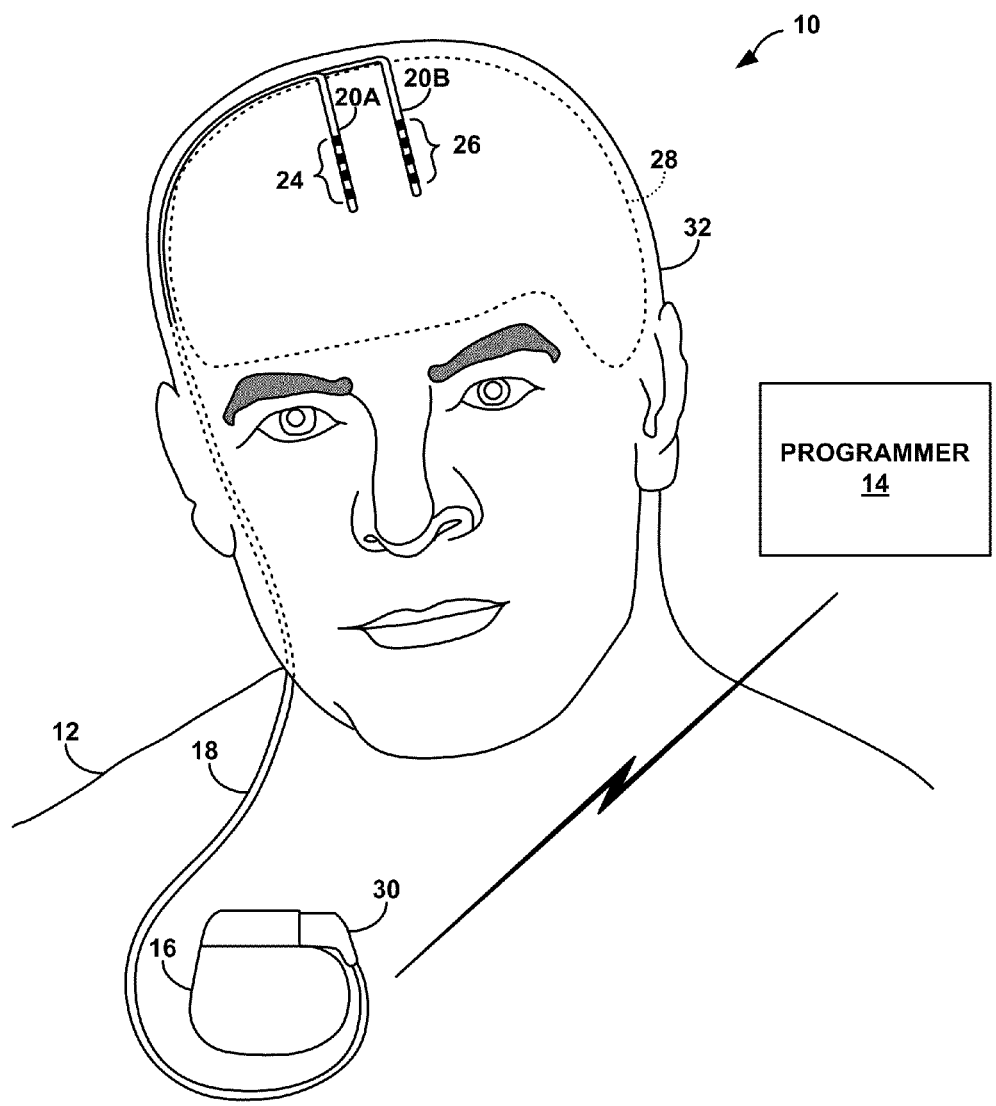
FIG. 1 is a conceptual diagram illustrating an example deep brain stimulation (DBS) system.

FIG. 1 is a conceptual diagram illustrating an example therapy system 10 that delivers therapy to manage a patient condition, such as a movement disorder, neurodegenerative impairment, a mood disorder or a seizure disorder of patient 12. Patient 12 ordinarily will be a human patient. In some cases, however, therapy system 10 may be applied to other mammalian or non-mammalian, non-human patients. While movement disorders and neurodegenerative impairment are primarily referred to herein, in other examples, therapy system 10 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post traumatic stress disorder, dysthymic disorder or obsessive-compulsive disorder (OCD)).

Therapy system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B (collectively referred to as "leads 20"), respectively, are positioned to deliver electrical stimulation to a tissue site within brain 28, such as a deep brain site under the dura mater of brain 28 of patient 12. In some examples, delivery of stimulation to one or more regions of brain 28, such as the subthalamic nucleus (e.g., the dorsal subthalamic nucleus), globus pallidus, internal capsule, thalamus or motor cortex, may be an effective treatment to mitigate or even eliminate one or more symptoms of movement disorders. A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Electrodes 24, 26 may also be positioned to sense bioelectrical brain signals within brain 28 of patient 12. In some examples, some of electrodes 24, 26 may be configured to only sense bioelectrical brain signals and other electrodes 24, 26 may be configured to only deliver electrical stimulation to brain 28. In other examples, some or all of electrodes 24, 26 are configured to both sense bioelectrical brain signals and deliver electrical stimulation to brain 28.

IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 includes at least one electrode and can include a plurality of electrodes. The subset of electrodes 24, 26 that are used to deliver electrical stimulation to patient 12, and, in some cases, the polarity of the subset of electrodes 24, 26, may be referred to as a stimulation electrode combination or configuration. In some examples, the stimulation electrode combination includes a first electrode positioned on a lead 20A or 20B and a reference electrode positioned relatively far from the first electrode (e.g., unipolar stimulation) or two or more electrodes positioned on one or more leads 20A, 20B (e.g., bipolar stimulation).

As described in further detail below, the stimulation electrode combination can be selected for a particular patient 12 and patient condition based on a bioelectrical brain signal sensed within brain 28 of patient 12 and a physiological model that is based on placement of electrodes of leads 20 within the brain of the patient. As described in further detail below, the physiological model can be generated by a computing device (e.g., a medical data computing device implemented in a general purpose computer, a medical device programmer, an external medical device, or an implantable medical device) executing instructions defining an algorithm that references a location of leads 20 within brain 28 relative to patient anatomy data. The location of leads 20 can be determined using any suitable technique, such as based on a medical image generated using any suitable imaging modality (e.g., computed tomography (CT), magnetic resonance imaging (MRI), x-ray or fluoroscopy), based on the stereotactic coordinates used to implant leads 20 within brain 28, based on correlations of signals sensed by IMD 16 with anatomical structures expected to yield those signals, correlations of stimulation effects at electrodes with anatomical structures expected to yield those effects, or based on a clinician-estimated location of leads 20 within brain 28.

In other examples, the stimulation electrode combination can be selected for a particular patient 12 and patient condition based on a bioelectrical brain signal sensed within brain 28 of patient 12 and a physiological model that is based on placement of electrodes of another medical member, such as a leadless electrical stimulator. Thus, although described with respect to electrodes of leads 20, the devices, systems, and techniques described herein can also be used to select a stimulation electrode combination based on placement of electrodes within brain 28 of patient 12, regardless of the type of component to which the electrodes are coupled. In such examples, the physiological model can be generated by a computing device (executing instructions defining an algorithm that references a location of the electrodes (or the medical member comprising the electrodes) within brain 28 relative to patient anatomy data. The location of the electrodes or medical component can be determined using any suitable technique, such as the techniques described with respect to leads 20.

Patient anatomy data indicates one or more characteristics of patient tissue proximate to implanted leads 20, such as one or more anatomical structures proximate implanted leads 20. The patient anatomy data may include at least one of an anatomical image of a patient, a reference anatomical image, an anatomical atlas or a tissue conductivity data set. The patient anatomy data may be specific to patient 12 or may represent data for more than one patient, e.g., model or averaged data of the anatomical structure and tissue conductivity of multiple patients. For example, in some examples, the patient anatomy data may include tissue conductivity data or other relevant tissue data that is typical for the particular lead 20 location for the particular therapeutic application (e.g., deep brain stimulation in the case of FIG. 1), and may be, but need not be, specific to patient 12. In some examples, the computing device generates the patient anatomy data from an imaging modality, such as, but not limited to, CT, MRI, x-ray, fluoroscopy, and the like.

In some examples, the bioelectrical signals sensed within brain 28 may reflect changes in electrical current produced by the sum of electrical potential differences across brain tissue. Examples of bioelectrical brain signals include, but are not limited to, electrical signals generated from local field potentials (LFP) sensed within one or more regions of brain 28, such as an electroencephalogram (EEG) signal, or an electrocorticogram (ECoG) signal. Local field potentials, however, may include a broader genus of electrical signals within brain 28 of patient 12.

In some examples, the bioelectrical brain signals that are used to select a stimulation electrode combination may be sensed within the same region of brain 28 as the target tissue site for the electrical stimulation or a different region of brain 28. As previously indicated, these tissue sites may include tissue sites within the thalamus, subthalamic nucleus (STN) or globus pallidus of brain 28, as well as other target tissue sites (e.g., other basal ganglia structures). The specific target tissue sites and/or regions within brain 28 may be selected based on the patient condition. Thus, in some examples, both a stimulation electrode combination and sense electrode combinations may be selected from the same set of electrodes 24, 26. In other examples, the electrodes used for delivering electrical stimulation may be different than the electrodes used for sensing bioelectrical brain signals.

A processor of therapy system 10 accesses a physiological model from, e.g., a memory of therapy system 10, which can be a memory of programmer 14, IMD 16 or a memory of another device (e.g., a database remotely located from programmer 14 or IMD 16 that stores one or more physiological models). The physiological model can be generated by the processor and stored in the memory, or generated by a different computing device and stored in the memory. The stored physiological model may be specific to patient 12 or may be general to more than one patient. For example, the stored physiological model may be generated based on placement of leads 20 and electrodes 24, 26 within brain 28 of patient 12. On the other hand, in some examples, the stored physiological model may indicate the lead location suggested for patients diagnosed with a patient condition similar to patient 12, as well as indicate characteristics of tissue proximate the electrodes of the lead when the lead is implanted in the suggested location.

In some examples, the processor generates a physiological model based on a placement of leads 20 and electrodes 24, 26 within brain 28. The physiological model can be generated with the aid of modeling software, hardware or firmware executing on a computing device, such as programmer 14 or a separate dedicated or multifunction computing device. In some examples, the processor displays the physiological model on a display of a user interface in order to provide information that guides a clinician in the selection of the stimulation electrodes. In other examples, the computing device provides a stimulation electrode combination recommendation based on the physiological model generated based on the location of lead 20 and the patient anatomy data.

In some examples, the physiological model comprises a graphical representation of a therapy field that represents a region of the patient's tissue to which therapy is delivered. For example, the therapy field can include an electrical stimulation field (also referred to as an electrical field) that is generated when IMD 16 delivers electrical stimulation to brain 28 of patient 12 via a selected subset of electrodes 24, 26 and a therapy program defining stimulation parameters. The electrical field represents the region of tissue that will be covered by an electrical field (e.g., an electrical field or an electromagnetic field) during therapy. In other examples, the therapy field can be an activation field, which indicates the neurons that will be activated by the electrical field in the patient anatomical region covered by the stimulation therapy, thereby indicating the tissue area activated by the electrical stimulation delivered via the specific therapy program, which includes a selected subset of electrodes 24, 26 and other stimulation parameter values (e.g., current or voltage amplitude value and/or frequency value). Another type of therapy field model is a voltage gradient or a current density model that indicates the voltage gradient or current density of an electrical field generated when IMD 16 delivers electrical stimulation to brain 28 of patient 12 via a selected subset of electrodes 24, 26 and a particular set of therapy parameter values.

In other examples, the physiological model includes a graphical representation of the one or more anatomical structures of brain 28 proximate the implanted leads 20, and, in some examples, also includes a graphical representation of leads 20. In some examples, the physiological model is determined based on the actual implant site of leads 20 within brain 28. For example, a processor of a computing device (e.g., programmer 14 or another computing device) can implement an algorithm that maps the 3D coordinates (e.g., stereotactic coordinates) of electrodes 24, 26 within brain 28 to at least one of an anatomical image of brain 28, a reference anatomical image of brain 28, or an anatomical atlas of brain 28 to determine and display the anatomical structures proximate implanted electrodes 24, 26.

The 3D coordinates can be the coordinates with which leads 20 were implanted in brain 28 or coordinates provided by a clinician that estimate the location of leads 20 within brain 28. The location of the anatomical structures within brain 28 can be determined based on patient anatomy data specific to patient 12 or generic to more than one patient. For example, the physiological model that includes the graphical representation of the anatomical structures of brain 28 can display an image of at least a portion of brain 28 of patient 12, an image of a brain that is not specific to patient 12 or a graphical, non-image based model of a human brain that is generic to more than one patient.

In other examples, the physiological model can include a representation of the one or more anatomical structures of brain 28 proximate leads 20, where the anatomical structures are selected based on the estimated implant site of leads 20. For example, programmer 14 or another computing device can generate and display an anatomical atlas based on the intended implant site for leads 20. The intended implant site for leads 20 can be determined, e.g., based on the target electrical stimulation sites that are believed to be useful for managing the patient condition, based on clinician input, or based on another input. In addition, the anatomical atlas of brain 28 can be generated based on medical imaging of brain 28 of a specific patient 12 or the anatomical atlas can be general to more than one patient (e.g., based on imaging of the brains of one or more other patients). While the anatomical atlas may not indicate the location in brain 28 at which leads 20 are actually implanted, the anatomical atlas can be useful for determining which target structures within brain 28 are useful for stimulating, or the target structures for which stimulation should be avoided (e.g., to minimize or even eliminate one or more stimulation-induced side effects).

In some examples, the stimulation electrode combination may be selected during a programming session following the implantation of IMD 16 and leads 20 in patient 12. A stimulation electrode combination can be selected for a particular patient 12 and patient condition based on a bioelectrical brain signal sensed within brain 28 of patient 12 by implanted leads 20 and a physiological model that indicates one or more anatomical structures of brain 28 proximate implanted leads 20. In some examples, the electrodes of the stimulation electrode combination can be selected based on a sensed bioelectrical brain signal and subsequently confirmed (e.g., validated) or otherwise verified based on the physiological model. Confirmation of the stimulation electrode combination can indicate, for example, whether the selected stimulation electrode combination is useful for delivering stimulation to the one or more target anatomical structures within brain 28 and/or reducing or even eliminating the delivery of stimulation to an anatomical structure associated with one or more stimulation-induced side effects. In other examples, an external device can sense the one or more bioelectrical brain signals, e.g., via surface electrodes positioned on an outer surface of cranium 32 of patient 12. Examples in which IMD 16 senses the bioelectrical signal within brain 28 are primarily referred to herein. However, the techniques for selecting a stimulation electrode combination can also be applied using bioelectrical brain signals sensed via external electrodes and/or an external, non-implanted medical device.

In some examples, during the programming session, bioelectrical brain signals may be sensed within brain 28 via a plurality of sense electrode combinations. Each sense electrode combination may include a different subset of one or more electrodes 24, 26. One or more signal characteristics (e.g., time domain characteristic or a frequency domain characteristic) of each of the sensed bioelectrical brain signals may be compared to each other and one or more sense electrode combinations may be selected based on the comparison. An example of a time domain characteristic includes a pattern in the time domain signal over time (e.g., a pattern or number of neuron spikes over time), variability of the time domain signal over time, a mean, median, average or peak amplitude of the signal, and the like. An example of a frequency domain characteristic may include power level (or energy level) within a particular frequency band. The power level may be determined based on, for example, a spectral analysis of a bioelectrical brain signal. The spectral analysis may indicate the distribution over frequency of the power contained in a signal based on a finite set of data.

In some examples, a stimulation electrode combination can be selected based on the one or more sense electrodes with which the bioelectrical brain signal with a time domain pattern substantially correlating to a template stored by programmer 14 was sensed. In other examples, a stimulation electrode combination can be selected based on the one or more sense electrodes with which the bioelectrical brain signal with a threshold number of spikes within a particular time frame were observed was sensed. The threshold number of spikes may be indicative of activity within a particular region of brain 28, and, therefore, sensing a bioelectrical signal with the threshold number of spikes can indicate the sense electrodes are positioned proximate the associated region of brain 28.

In other examples, a stimulation electrode combination can be selected based on a variability of sensed bioelectrical brain signals. For example, a stimulation electrode combination can be selected based on the one or more sense electrodes with which the bioelectrical brain signal having a variability that matches or substantially matches (e.g., is within a threshold percentage, such as about 1% to about 25%) a predetermined variability was sensed. As another example, a stimulation electrode combination can be selected based on the one or more sense electrodes with which the bioelectrical brain signal having a variability that is less than a predetermined threshold variability was sensed. The template and the threshold variability value may be indicative of activity within a particular region of brain 28, and, therefore, sensing a bioelectrical signal with a variability less than or equal to the threshold variability can indicate the sense electrodes are positioned proximate the associated region of brain 28.

In other examples, a stimulation electrode combination can be selected based on the one or more sense electrodes with which the bioelectrical brain signal with a mean, median, average or peak amplitude that is greater than or, in some examples, less than, a predetermined threshold value was sensed. The threshold value may be associated with activity within a particular region of brain 28 and, therefore, sensing a bioelectrical signal with an amplitude less than or equal to the threshold amplitude value can indicate the sense electrodes are positioned proximate the associated region of brain 28.

In other examples, a stimulation electrode combination can be selected based on the one or more sense electrodes with which the bioelectrical brain signal with the highest relative band power (or energy) level in a selected frequency band was sensed. This may indicate, for example, that the one or more electrodes with which the bioelectrical brain signal with the highest relative band power level was sensed is located closest to the target tissue site, which can be a region within brain 28 that produces a bioelectrical signal with the highest relative power level within a selected frequency band. The relative power level may be a ratio of the power in the selected frequency band of the sensed signal to the overall power of the sensed signal. The particular frequency band of interest may be selected based on the patient condition. For example, it is believed that abnormal activity within a beta band (e.g., about 8 hertz (Hz) to about 30 Hz or about 16 Hz to about 30 Hz) of a bioelectrical brain signal is indicative of brain activity associated with a movement disorder (e.g., Parkinson's disease), as well as revealing of a target tissue site for therapy delivery to manage the patient condition. Therefore, in some examples, the power level within a beta band of a bioelectrical brain signal can be used to identify a target tissue site for stimulation therapy to manage a movement disorder.

In other examples, depending on the patient condition, electrical activity within a gamma band (e.g., about 35 Hz to about 120 Hz) of a bioelectrical brain signal may reveal a target tissue site. For example, a target tissue site, e.g., the subthalamic nucleus, within the brain of a patient with Parkinson's disease or another movement disorder may exhibit bioelectrical brain signals with high gamma band activity when the patient is treated with medication or when the patient moves. Therefore, in some examples, the power level within a gamma band of a bioelectrical brain signal can be used to identify a target tissue site.

Some algorithms for selecting a stimulation electrode combination based on a bioelectrical brain signal described herein help identify the location of a target tissue site in a direction substantially along a longitudinal axis of one or both leads 20. That is, some algorithms described herein help identify which electrode 24, 26 along the respective lead 20 is closest to the target tissue site, whereby each of the electrodes 24 is displaced from an adjacent electrode in an axial direction along the longitudinal axis of lead 20A, and each of the electrodes 26 is displaced from an adjacent electrode in an axial direction along the longitudinal axis of lead 20B. Such algorithms may be useful for identifying the location of a target tissue site in a direction substantially along a longitudinal axis of a cylindrical lead, a paddle lead or grid electrodes (e.g., used for stimulation of a cortex of brain 28).

In addition, in some examples, some algorithms described herein may help identify the location of a target tissue site in a direction other than a direction indicated by the longitudinal axis of one or both leads 20. For example, algorithms described herein may help identify the location of a target tissue site in a direction indicated by each of a plurality of segmented or partial ring electrodes that share an axial position along a longitudinal axis of one or both leads 20, but have different radial positions (e.g., a direction substantially perpendicular to the longitudinal axis of one or both leads 20). When both types of algorithms are combined, such that the location of a target tissue site is determined in two directions, the combined algorithm can be referred to as a 3D algorithm, which can be used to locate a relative target tissue site in three dimensions.

In some cases, the target tissue site for therapy delivery may be located between two sense electrodes. If the target tissue site is located directly between two sense electrodes, determining which of the sense electrodes is closest to the target tissue site may require a more complex algorithm than simply determining the electrode or electrodes that sensed the bioelectrical signal with the highest relative power level within the selected frequency band. In examples described herein, an algorithm that determines whether the target tissue site is located between sensed electrodes may be applied to determine the electrode or electrodes that are located closest to a target tissue site.

In some examples, the algorithm for selecting a stimulation electrode combination based on a bioelectrical brain signal includes sensing a plurality of bioelectrical brain signals and determining the relative beta band power levels. The relative beta band power may be a ratio of the power in a beta band of the sensed signal to the overall power of the sensed signal. The relative beta band power may be used instead of the beta band power in order to normalize the bioelectrical signals sensed by sense electrodes located in different regions of a patient's brain. This normalization of sensed brain signals applies to the power level within any selected frequency band. Thus, while "power levels" within a selected frequency band of a sensed brain signal are generally referred to herein, the power level may be a relative power level, which is a ratio of a power level in a selected frequency band of a sensed brain signal to the overall power of the sensed brain signal.

The power level in the selected frequency band may be determined using any suitable technique. In some examples, a processor of IMD 16 may average the power level of the selected frequency band of a sensed brain signal over a predetermined time period, such as about ten seconds to about two minutes, although other time ranges are also contemplated. In other examples, the selected frequency band power level may be a median power level over a predetermined range of time, such as about ten seconds to about two minutes. The activity within the selected frequency band of a brain signal, as well as other frequency bands of interest, may fluctuate over time. Thus, the power level in the selected frequency band at one instant in time may not provide an accurate and precise indication of the energy of the brain signal in the selected frequency band. Averaging or otherwise monitoring the power level in the selected frequency band over time may help capture a range of power levels, and, therefore, a better indication of the patient's pathological state in the particular brain region sensed by IMD 16.

The overall power of a sensed bioelectrical brain signal may be determined using any suitable technique. In one example, a processor of IMD 16 (or another device, such as programmer 14) may determine an overall power level of a sensed bioelectrical brain signal based on the total power level of a swept spectrum of the brain signal. To generate the swept spectrum, the processor can control a sensing module to tune to consecutive frequency bands over time, and the processor may assemble a pseudo-spectrogram of the sensed bioelectrical brain signal based on the power level in each of the extracted frequency bands. The pseudo-spectrogram may be indicative of the energy of the frequency content of the bioelectrical brain signal within a particular window of time.

The algorithm for selecting a stimulation electrode combination based on a bioelectrical brain signal further includes determining a plurality of relative values of the relative beta band power level, where each relative value is based on the relative beta band power levels of two bioelectrical signals sensed by two different electrodes, and selecting the sense electrode or electrodes that are closest to the target tissue site based on the plurality of relative values. The selected electrode or electrodes may be associated with one or more stimulation electrode combinations, which may be programmed into IMD 16 for the delivery of stimulation therapy to brain 28. In this way, the stimulation electrode combination may be selected based on a characteristic of a bioelectrical brain signal. While frequency domain characteristics are primarily referred to herein, the techniques described herein for selecting a stimulation electrode may also be applicable to selecting one or more stimulation electrodes based on a time domain characteristic of a bioelectrical brain signal (e.g., individual neuron spikes, a pattern in an amplitude over time, variability of the time domain signal over time, comparison of an amplitude to a threshold value, and the like).

In some examples, other stimulation parameter values may be selected based on the frequency domain characteristics of a bioelectrical brain signal sensed via one or more groups of sense electrodes associated with a stimulation electrode combination. For example, a beta band power level may be associated with a stimulation amplitude value that may provide efficacious therapy to patient 12. A group of electrodes includes at least one electrode and can include a plurality of electrodes.

After selecting one of the sense electrode combinations based on the bioelectrical brain signal, the electrodes of the sense electrode combination can be selected as the stimulation electrode combination if the physiological model indicates the selected electrodes are useful for providing efficacious stimulation therapy to patient 12. For example, the physiological model can indicate whether the electrodes of the sense electrode combination are proximate the target anatomical structures within brain 28 or whether the electrodes are proximate anatomical structures that are to be avoided, e.g., because the stimulation of the anatomical structures may induce side effects. The target anatomical structures can be, for example, the anatomical structures (or regions) of brain 28 for electrical stimulation (or other therapy delivery) that result in relatively efficacious therapy for the patient condition. Example anatomical structures of brain 28 include, but are not limited to, the frontal lobe, the parietal lobe, the occipital lobe, the temporal lobe, thalamus (e.g., the anterior hypothalamic nucleus or the dorsomedial hypothalamic nucleus), the hypothalamus, the amygdala, the hippocampus, the primary motor cortex, the premotor cortex, the dorsolateral prefrontal cortex, the posterior parietal cortex, and the cerebellum.

With placement of one or both leads 20 in the subthalamic nucleus (STN) of brain 28, structures of brain 28 to avoid activating may include corticobulbar and/or corticospinal tracts coursing within the internal capsule that may induce muscle contractions, medial lemniscal fibers which may induce paresthesia, and oculomotor nerve fibers which may induce skewed deviation of the eyes of patient 12. In another example, with placement of one or both leads 20 in the globus pallidus interna (GPi), structures of brain 28 to avoid activating may include the internal capsule which may induce muscle contractions, and the optic tract which may cause phosphenes and other visual disturbances. In addition, with placement of one or both leads 20 in the Vim of thalamus, structures to avoid activating may include the thalamic nucelus ventralis caudalis (also referred to as "Vc nucleus") which may induce paresthesia, and the internal capsule which may induce muscle contractions. In other examples, activating other structures within brain 28 and/or fiber pathways may lead to other stimulation induced side effects.

In some examples, programmer 14 or another computing device can generate the physiological model and display the physiological model on a display of a user interface. The clinician can then determine, based on the display of the physiological model, whether the electrodes of the sense electrode combination are proximate the target anatomical structures or the anatomical structures to be avoided. As another example, programmer 14 or another computing device can automatically determine whether the electrodes of the sense electrode combination are proximate the target anatomical structures based on the physiological model that indicates the anatomical structure of brain 28 of patient 12 proximate the implanted electrodes 24, 26.

In other examples, the electrodes of the stimulation electrode combination can be selected based on a physiological model and the stimulation electrode selection can be confirmed (e.g., validated) based on a bioelectrical brain signal sensed via the electrodes of the stimulation electrode combination. For example, programmer 14 or another computing device can generate a display of the physiological model, based on which the clinician can select the electrodes of the stimulation electrode combination. As an example, the clinician can select the electrodes and other stimulation parameter values that deliver stimulation to the one or more target anatomical structures for the stimulation signals and minimize or even avoid stimulating other anatomical structures, such as anatomical structures that are associated with one or more stimulation-induced side effects.

Selecting one or more stimulation electrode combinations for therapy system 10 based on a sensed bioelectrical brain signal and a physiological model may be useful for reducing the amount of time required to select efficacious stimulation electrode combinations. In the example shown in FIG. 1, therapy system 10 comprises eight electrodes 24, 26, whereby any combination of the eight electrodes 24, 26 may be selected to provide stimulation therapy to brain 28. In some existing techniques, a clinician randomly selects and tests stimulation electrode combinations in order to find an efficacious stimulation electrode combination. In some cases, the clinician's knowledge and experience in selecting stimulation electrode combinations may help limit the amount of time required to select stimulation electrode combinations. The clinician may select a stimulation electrode combination based on a balance of side effects experienced by patient 12 and the extent to which the symptoms of the patient's movement disorder (or other patient condition) are mitigated. In these existing techniques, the clinician may not consider the specific anatomical configuration of brain 28 of patient 12 to select electrode combinations to test, nor the particular physiological characteristics of patient 12 and the particular dysfunctional state of the patient's brain 28. Moreover, these techniques for selecting and testing stimulation electrode combinations and identifying a relatively efficacious stimulation electrode combination may be relatively time consuming and tedious.

In contrast, in the systems, devices, and techniques described herein, physiological information regarding the brain 28 of patient 12 guide the selection of stimulation electrodes, which can help increase the efficiency with which an efficacious stimulation electrode combination is selected. In particular, sensed bioelectrical brain signals in combination with a physiological model that indicates a region of brain 28 of patient 12 proximate implanted electrodes 24, 26 may provide a clinician with useful information for determining which electrodes 24, 26 are positioned to deliver efficacious stimulation therapy to brain 28 of patient 12. With respect to the bioelectrical brain signals, the physiological information for selecting an efficacious stimulation electrode combination may be in the form of one or more time domain characteristics (e.g., amplitude) or frequency domain characteristics of a bioelectrical brain signal sensed by a particular group of sense electrodes. Differences in the amplitude of the one or more frequency domain characteristics of bioelectrical signals sensed with different electrodes may provide additional information for determining a sense electrode or electrodes that are closest to a target tissue site within brain 28 and may facilitate selection of an efficacious stimulation electrode combination. The sensed bioelectrical brain signals are specific to patient 12 because they are sensed within the patient's brain 28, and, therefore, may be used to relatively quickly ascertain the stimulation electrode combinations that may provide efficacious therapy to the specific patient 12.

In addition to decreasing the time required to select an efficacious stimulation electrode combination, the techniques described herein may also help decrease the amount of expertise or experience required to find an efficacious stimulation electrode combination in an efficient manner. For example, as described in further detail below, programmer 14 or another computing device may automatically evaluate one or more electrode combinations and determine which particular electrode combination is may provide efficacious therapy to patient 12 based on the bioelectrical brain signals specific to patient 12 and specific to the actual lead placement within the patient's brain 28.

With respect to the physiological model, the physiological information for selecting an efficacious stimulation electrode combination for patient 12 can be an identification of one or more target anatomical structures for the therapeutic electrical stimulation, one or more anatomical structures for which it is desirable to minimize the delivery of stimulation, e.g., because the anatomical structures are related to a stimulation-induced side effect or a therapy model that indicates the therapy field that can result from delivering stimulation to patient 12 via the selected stimulation electrode combination. In examples in which programmer 14 or another computing device displays a graphical representation of the physiological model, the physiological model can help a clinician visualize the location of leads 20 within brain 28 of patient 12, which can help the clinician determine which electrodes 24, 26 are proximate the target anatomical structures for the stimulation and the anatomical structures to avoid.

In examples in which the physiological model includes a therapy field model that indicates the therapy field that can result from delivering stimulation to patient 12 via the selected stimulation electrode combination, the physiological information provided by the physiological model may include an indication of how stimulation may affect tissue within brain 28. As discussed above, example therapy field models include an electrical field model, an activation field model, or a voltage gradient or current density model. In examples in which programmer 14 or another computing device displays a graphical representation of the therapy field model, the displayed model can also help a clinician visualize a characteristic (e.g., a volume or location) of a therapy field that results from therapy delivery via a selected stimulation electrode combination. Visualization of the therapy field model can be useful for, for example, visualizing whether the therapy field overlaps with the target anatomical structures for the stimulation and the anatomical structures associated with stimulation-induced side effects. The selected electrodes and/or one or more stimulation parameter values can be modified to adjust the therapy field.

In addition to decreasing the time required to select an efficacious stimulation electrode combination, the techniques described herein may also help decrease the amount of expertise or experience required to find an efficacious stimulation electrode combination in an efficient manner. For example, as described in further detail below, programmer 14 or another computing device may automatically evaluate one or more groups of sense electrodes and determine which particular group of sense electrodes is associated with a stimulation electrode combination that may provide efficacious therapy to patient 12 based on the bioelectrical brain signals specific to patient 12 and specific to the actual lead placement within the patient's brain 28. Programmer 14 can then automatically select the stimulation electrode combination based on a selected sense electrode combination. With some patient conditions, such as movement disorders, the bioelectrical brain signals help guide the clinician to the region of brain 28 that is associated with the patient condition.

In addition, in some examples, programmer 14 or another computing device can automatically determine whether the selected electrode combination is proximate the one or more target anatomical structures within brain 28 of patient 12 or proximate an anatomical structure associated with a stimulation-induced side effect based on a physiological model. The physiological model indicates the structure of brain 28 of patient 12 proximate an estimated or actual location of leads 20 within brain 28, thereby providing physiological information with which programmer 14 can automatically determine whether the selected stimulation electrodes are positioned in a physiologically significant location within brain 28 (e.g., a location proximate the target anatomical structure for the stimulation or proximate a structure associated with stimulation-induced side effects). In other examples, the physiological model provides physiological information that guides a clinician in determining whether the selected stimulation electrodes are positioned in a physiologically significant location within brain 28 (e.g., a location proximate the target anatomical structure for the stimulation or proximate a structure associated with stimulation-induced side effects).

While it may be useful to select a stimulation electrode combination based on a sensed bioelectrical brain signal and without consideration of a physiological model, the physiological model can provide additional physiological information that may be useful for confirming that the stimulation electrodes selected based on the sense electrode combination used to sense the bioelectrical brain signal is proximate to the target tissue site and/or for confirming that the stimulation electrodes are not proximate to an tissue site within brain 28 to which stimulation delivery may result in one or more side effects.

Similarly, while it may be useful to select stimulation electrode combination based on a physiological model and without consideration of bioelectrical brain signals sensed via the electrodes of the stimulation electrode combination, it can be useful to confirm the stimulation electrode selection based on a sensed bioelectrical brain signal. As discussed in further detail below, the sensed bioelectrical brain signal can be revealing of the location of the stimulation electrodes relative to the target tissue site.

After selecting stimulation electrode combinations in accordance with the systems and techniques described herein, a clinician, alone or with the aid of a computing device, such as programmer 14, may select the other stimulation parameter values that provide efficacious therapy to patient 12. These other stimulation parameter values may include, for example, a frequency and amplitude of stimulation signals, and, in the case of stimulation pulses, a duty cycle and pulse width of the stimulation signals. In other cases, programmer 14 may suggest information about the stimulation waveform as well as pattern of delivered stimulation pulses.

In some examples, after IMD 16 is implanted within patient 12 and programmed for chronic therapy delivery, IMD 16 may periodically reassess the selected stimulation electrode combination to determine whether another stimulation electrode combination may provide more efficacious therapy. IMD 16 may determine, for example, whether the target tissue site for stimulation therapy has changed, e.g., based on physiological changes in brain 28 or whether one or both leads 20A, 20B have migrated away from the original implant site within brain 28.

In some examples, in order to periodically reassess the selected stimulation electrode combination, IMD 16 may periodically sense bioelectrical brain signals with one or more groups of sense electrodes comprising electrodes 24, 26 of leads 20A, 20B, respectively. The processor of programmer 14 or IMD 16 may determine whether stimulation should be delivered to brain 28 with a different stimulation electrode combination based on an analysis of the frequency band characteristics of the sensed bioelectrical brain signals. For example, the processor of IMD 16 may switch the subset of electrodes with which IMD 16 delivers stimulation to patient 12 if the currently selected stimulation electrode combination is not associated with a group of sense electrodes that is closest to a target tissue site exhibiting a bioelectrical signal having the highest relative beta band power. In this way, the stimulation electrode combination used by IMD 16 to deliver electrical stimulation to patient 12 may be dynamically changed in a closed-loop system.

In addition to or instead of reassessing the selected stimulation electrode combination based on bioelectrical brain signals with one or more groups of sense electrodes comprising electrodes 24, 26 of leads 20A, 20B, respectively, the processor of programmer 14, IMD 16 or another device can periodically assess whether the stimulation electrodes provide efficacious therapy to brain 28 based on a physiological model that is generated based on the actual implant location of the electrodes 24, 26. The physiological model can indicate, for example, whether one or more of leads 20 have migrated within brain 28 such that one or more stimulation electrodes are no longer positioned to deliver electrical stimulation to the target tissue site or such that one or more stimulation electrodes are delivering stimulation to a tissue site associated with a stimulation-induced side effect.

In order to assess the selected stimulation electrode combination based on the physiological model, a clinician can obtain a medical image of leads 20 and respective electrodes 24, 26 using any suitable imaging modality. Programmer 14 or another computing device can generate the physiological model based on the location of electrodes 24, 26 indicated by the medical image and patient anatomy data. The physiological model can indicate, for example, whether the selected stimulation electrodes are still positioned to deliver electrical stimulation to the one or more target anatomical structure and/or avoid the one or more anatomical structures associated with a stimulation-induced side effect. For example, the physiological model can indicate whether the electrical field, activation field, voltage gradient or current density of the therapy field resulting from stimulation delivery via the selected stimulation electrode combination is still targeting the target anatomical structures and/or avoiding the anatomical structures associated with stimulation-induced side effects.

Electrical stimulation generated by IMD 16 may be configured to manage a variety of disorders and conditions. In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. As previously indicated, the stimulation electrode combination may indicate the specific electrodes 24, 26 that are selected to deliver stimulation signals to tissue of patient 12 and the respective polarity of the selected electrodes.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory.

As shown in FIG. 1, implanted lead extension 18 is coupled to IMD 16 via connector 30 (also referred to as a connector block or a header of IMD 16). In the example of FIG. 1, lead extension 18 traverses from the implant site of IMD 16 and along the neck of patient 12 to cranium 32 of patient 12 to access brain 28. In the example shown in FIG. 1, leads 20A and 20B (collectively "leads 20") are implanted within the right and left hemispheres, respectively, of patient 12 in order to deliver electrical stimulation to one or more regions of brain 28, which may be selected based on the patient condition or disorder controlled by therapy system 10. The stimulation electrodes used to deliver stimulation to the target tissue site may be selected based on one or more sensed bioelectrical brain signals and a physiological model that indicates a region of brain 28 proximate the implanted electrodes, e.g., using the algorithms described herein, e.g., with respect to FIGS. 5-10. Other lead 20 and IMD 16 implant sites are contemplated. For example, IMD 16 may be implanted on or within cranium 32, in some examples. As another example, leads 20 may be implanted within the same hemisphere of brain 28 or IMD 16 may be coupled to a single lead.

Although leads 20 are shown in FIG. 1 as being coupled to a common lead extension 18, in other examples, leads 20 may be coupled to IMD 16 via separate lead extensions or directly to connector 30. Leads 20 may be positioned to deliver electrical stimulation to one or more target tissue sites within brain 28 to manage patient symptoms associated with a patient condition, such as a movement disorder. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 or within the cerebral cortex of brain 28 via a burr hole in cranium 32 of patient 12, and electrically coupled to IMD 16 via one or more leads 20.

In the example shown in FIG. 1, electrodes 24, 26 of leads 20 are shown as ring electrodes. Ring electrodes may be used in DBS applications because they are relatively simple to program and are capable of delivering an electrical field to any tissue adjacent to electrodes 24, 26. In other examples, electrodes 24, 26 may have different configurations. For example, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed in a specific direction from leads 20 to enhance therapy efficacy and reduce possible adverse side effects from stimulating a large volume of tissue. An example of a complex electrode array geometry including segmented electrodes is shown and described with reference to FIGS. 3A and 3B. In some examples, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12 and/or minimizing invasiveness of leads 20. In addition, in other examples, leads 20 may include both macro electrodes (e.g., rings, segments adapted to sensing local field potentials and stimulation) and micro electrodes (e.g., adapted to sensing spike trains in the time domain) in any combination.

In the example shown in FIG. 1, IMD 16 includes a memory (shown in FIG. 3) to store a plurality of therapy programs that each define a set of therapy parameter values. In some examples, IMD 16 may select a therapy program from the memory based on various parameters, such as a detected patient activity level, a detected patient state, based on the time of day, and the like. IMD 16 may generate electrical stimulation based on the selected therapy program to manage the patient symptoms associated with a movement disorder (or another patient condition).

During a trial stage in which IMD 16 is evaluated to determine whether IMD 16 provides efficacious therapy to patient 12, a plurality of therapy programs may be tested and evaluated for efficacy. In addition, one or more stimulation electrode combinations may be selected for the one or more therapy programs based on at least one sensed bioelectrical brain signal and a physiological model that is determined based on a location of leads 20 within brain 28, as described in further detail below. Therapy programs may be selected for storage within IMD 16 based on the results of the trial stage.

During chronic therapy in which IMD 16 is implanted within patient 12 for delivery of therapy on a non-temporary basis, IMD 16 may generate and deliver stimulation signals to patient 12 according to different therapy programs. In addition, in some examples, patient 12 may modify the value of one or more therapy parameter values within a single given program or switch between programs in order to alter the efficacy of the therapy as perceived by patient 12 with the aid of programmer 14. The memory of IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., activation of power, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that provide efficacious therapy to patient 12 to address symptoms associated with the patient condition, and, in some cases, specific to one or more different patient states, such as a sleep state, movement state or rest state. For example, the clinician may select one or more stimulation electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient 12 (e.g., muscle activity or muscle tone). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the IEEE 802.11 or Bluetooth® specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 can be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads, implanted leads via a percutaneous extension or one or more external leads. If the trial stimulator indicates DBS system 10 provides effective treatment to patient 12, the clinician may implant a chronic stimulator within patient 12 for relatively long-term treatment.

In other examples of therapy system 10, therapy system 10 includes only one lead or more than two leads. The devices, systems, and techniques described below with respect to selecting a stimulation electrode combination can be applied to a therapy system that includes only one lead or more than two leads.

Figure 2:
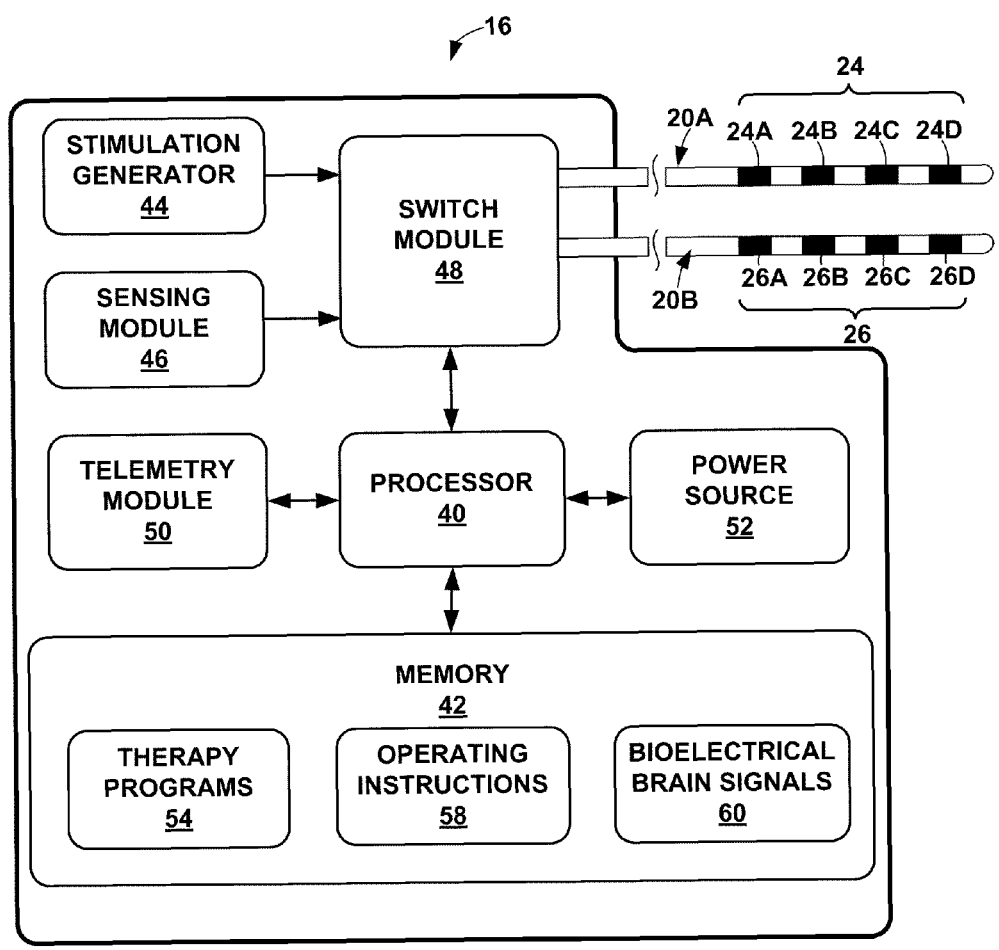
FIG. 2 is functional block diagram illustrating components of an example medical device.

FIG. 2 is a functional block diagram illustrating components of an example IMD 16. In the example shown in FIG. 2, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

In the example shown in FIG. 2, memory 42 stores therapy programs 54, bioelectrical brain signals 60, and operating instructions 58 in separate memories within memory 42 or separate areas within memory 42. Each stored therapy program 54 defines a particular set of electrical stimulation parameters, such as a stimulation electrode combination, current or voltage amplitude, frequency (e.g., pulse rate in the case of stimulation pulses), and pulse width. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Bioelectrical brain signals 60 include bioelectrical brain signals sensed within brain 28 of patient 12 by sensing module 46. Example bioelectrical brain signals include, but are not limited to, a signal generated from local field potentials within one or more regions of brain 28. EEG and ECoG signals are examples of local field potentials that may be measured within brain 28. However, local field potentials may include a broader genus of electrical signals within brain 28 of patient 12. In some examples, bioelectrical brain signals 60 are raw bioelectrical brain signals sensed by sensing module 46 (or another sensing module), a parameterized bioelectrical brain signal generated by sensing module 46 or data generated based on the raw bioelectrical brain signal. Operating instructions 58 guide general operation of IMD 16 under control of processor 40.

Stimulation generator 44, under the control of processor 40, generates stimulation signals for delivery to patient 12 via a selected subset of electrodes 24, 26. An example range of electrical stimulation parameters believed to be effective in DBS to manage a movement disorder of patient include:

1. Frequency: between approximately 100 Hz and approximately 500 Hz, such as approximately 130 Hz.
2. Voltage Amplitude: between approximately 0.1 volts and approximately 50 volts, such as between approximately 0.5 volts and approximately 20 volts, or approximately 5 volts.
3. Current Amplitude: A current amplitude may be the charge flow caused by controlling a voltage across a biological load. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 44 generates electrical stimulation signals in accordance with the electrical stimulation parameters noted above. Other ranges of therapy parameter values may also be useful, and may depend on the target stimulation site within patient 12. While stimulation pulses are described, stimulation signals may be of any form, such as continuous-time signals (e.g., sine waves) or the like.

Processor 40 may include any one or more of a microprocessor, a controller, a digital signal processor (DSP), an application specific integrated circuit (ASIC), a field-programmable gate array (FPGA), or discrete logic circuitry. The functions attributed to processors described herein may be embodied in a hardware device via software, firmware, hardware or any combination thereof. Processor 40 controls stimulation generator 44 according to therapy programs 54 stored in memory 42 to apply particular stimulation parameter values specified by one or more of programs, such as amplitude, pulse width, and pulse rate.

In the example shown in FIG. 2, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48.

Stimulation generator 44 can be a single channel or multi-channel stimulation generator. In particular, stimulation generator 44 may be capable of delivering a single stimulation pulse, multiple stimulation pulses, or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

In some examples, processor 40 dynamically changes the selected combinations of electrodes 24, 26, i.e., the stimulation electrode combination, based on one or more frequency domain characteristics of bioelectrical signals sensed within brain 28. Sensing module 46, under the control of processor 40, may sense bioelectrical brain signals and provide the sensed bioelectrical brain signals to processor 40. Processor 40 may control switch module 48 to couple sensing module 46 to a selected combinations of electrodes 24, 26, e.g., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal sensed across the selected electrodes 24, 26 to sensing module 46. The bioelectrical brain signal may include electrical signals that are indicative of electrical activity within brain 28 of patient 12. Processor 40 can store the sensed bioelectrical brain signals in memory 42.

Although sensing module 46 is incorporated into a common housing with stimulation generator 44 and processor 40 in FIG. 2, in other examples, sensing module 46 may be in a separate housing from IMD 16 and may communicate with processor 40 (and, in some examples, programmer 14) via wired or wireless communication techniques.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by RF communication techniques. In addition, telemetry module 50 may communicate with external medical device programmer 14 via proximal inductive interaction of IMD 16 with programmer 14. Accordingly, telemetry module 50 may send information, such as information relating to sensed bioelectrical brain signals, to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Throughout the disclosure, a group of electrodes may refer to any electrodes located at the same position along the longitudinal axis of one or more leads. A group of electrodes may include one electrode or a plurality of electrodes (e.g., two or more electrodes).

Figure 3A:
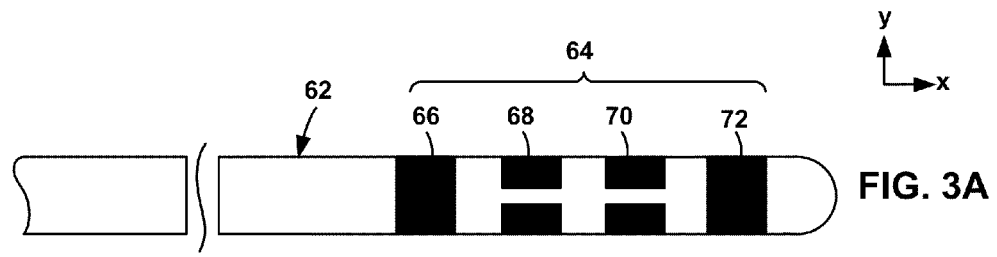
FIGS. 3A and 3B are diagrams illustrating an example electrode configuration of a medical lead.
Figure 3B:
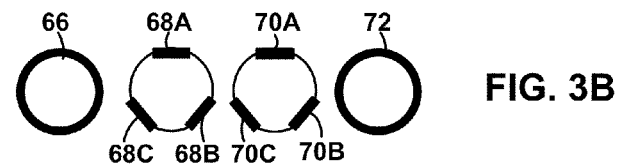

FIGS. 3A and 3B are schematic illustrations of an example lead 62 and groups of electrodes 64 that may be used with IMD 16 instead of or in addition to one or both leads 20A, 20B including respective sets of electrodes 24, 26. FIG. 3A shows a two-dimensional (2D) side view in the x-y plane (orthogonal x-y axes are shown in FIG. 3A for ease of description only) of lead 62, which includes four groups of electrodes 66, 68, 70, and 72. FIG. 3B shows a cross-sectional view in the y-z plane of each of the four groups of electrodes. Groups of electrodes 66 and 72 each comprise one ring electrode, which may be similar to each of electrodes 24, 26 shown in FIG. 2. In contrast, groups of electrodes 68 and 70 each comprise three segmented electrodes 68A-68C and 70A-70C distributed around the outer perimeter of lead 62. In other examples, lead 62 may comprise any number and combination of groups of ring electrodes or segmented electrodes. For example, lead 62 may comprise only groups of segmented electrodes. As another example, groups 68, 70 of electrodes may comprise more than three segmented (or partial ring) electrodes or one or two segmented or partial ring electrodes.

Figure 4:
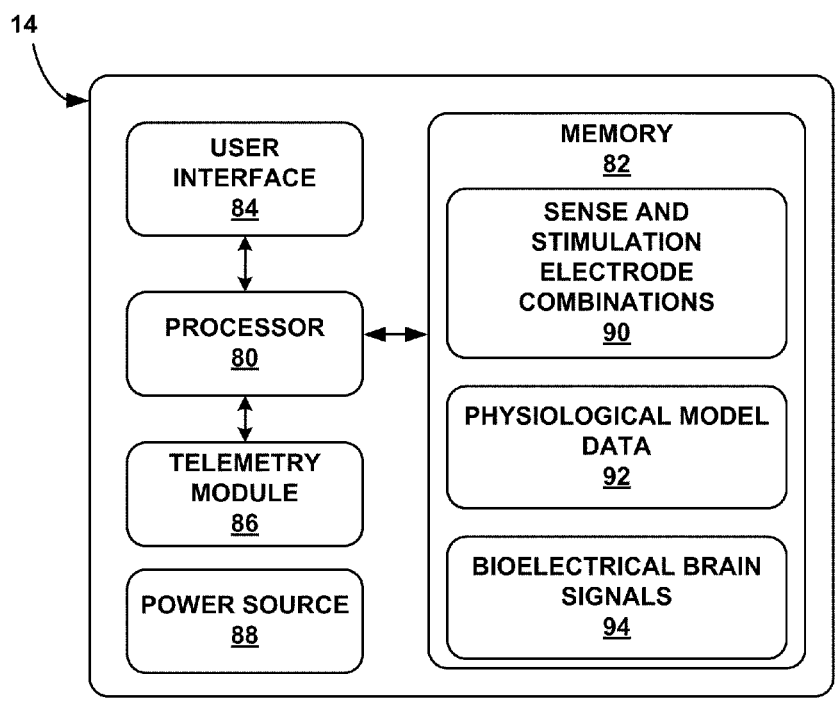
FIG. 4 is a functional block diagram illustrating components of an example medical device programmer.

FIG. 4 is a conceptual block diagram of an example external medical device programmer 14, which includes processor 80, memory 82, user interface 84, telemetry module 86, and power source 88. Processor 80 controls user interface 84 and telemetry module 86, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 84. User interface 84 includes a display (not shown), such as a LCD or LED display or other type of screen, to present information related to the therapy, such as information related to bioelectrical signals sensed via a plurality of sense electrode combinations. In addition, user interface 84 may include an input mechanism to receive input from the user. The input mechanisms may include, for example, buttons, a keypad (e.g., an alphanumeric keypad), a peripheral pointing device, or another input mechanism that allows the user to navigate though user interfaces presented by processor 80 of programmer 14 and provide input.

If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the display (not shown) of programmer 14 may be a touch screen that allows the user to provide input directly to the user interface shown on the display. The user may use a stylus or a finger to provide input to the display. In other examples, user interface 84 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 80 of programmer 14. In addition, in some examples, processor 80 may select a stimulation electrode combination based on a bioelectrical brain signal sensed by IMD 16 and a physiological model that indicates a one or more characteristics of tissue of brain 28 of patient 12 proximate implanted electrodes 24, 26 of leads 20. The examples described herein primarily refer to a bioelectrical brain signal sensed by IMD 16, but are also applicable to selecting an electrode combination based on a bioelectrical brain signal sensed by a sensing module that is separate from IMD 16. The separate sensing module may, but need not be, implanted within patient 12.

In some examples, processor 80 may select one or more electrodes based on time domain characteristics of a sensed bioelectrical signal, such as a sensed spike train from an individual or small group of neurons. As described in further detail below, in some examples, processor 80 may select one or more electrodes based on the differences in amplitude of a frequency domain characteristic of bioelectrical brain signals sensed with different sense electrode combinations associated with at least one of the stimulation electrode combinations. Processor 80 may select a stimulation electrode combination for IMD 16 based on the analysis of the frequency domain characteristics of the sensed bioelectrical brain signals, e.g., by implementing an algorithm described below with respect to FIGS. 12, 13, 15A-15C, 16 or 17, as well as based on a physiological model that is generated based on the placement of leads 20 within brain 28. In some cases, e.g., after determining another stimulation electrode combination is desirable based on a comparison of the frequency domain characteristics of a plurality of bioelectrical brain signals sensed by a respective electrode combination and a physiological model, processor 80 may transmit a signal to IMD 16 to instruct IMD 16 to switch stimulation electrode combinations.

Processor 40 of IMD 16 may receive the signal from programmer 14 via its respective telemetry module 50 (FIG. 3). Processor 40 of IMD 16 may switch stimulation electrode combinations by selecting a stored therapy program from memory 42 based on the signal from processor 80 of programmer 14. Alternatively, processor 80 of programmer 14 may select a therapy program or a specific stimulation electrode combination and transmit a signal to IMD 16, where the signal indicates the therapy parameter values to be implemented by IMD 16 to help improve the efficacy of the stimulation to manage the patient's movement disorder. The indication may be, for example, an alphanumeric identifier or symbol that is associated with the therapy program in memory 42 of IMD 16.

In the example shown in FIG. 4, memory 82 stores sense and stimulation electrode combinations 90, physiological model data 92, and bioelectrical brain signals 94 in separate memories within memory 82 or separate areas within memory 82. Memory 82 may also include instructions for operating user interface 84 and telemetry module 86, and for managing power source 88. Memory 82 may also store any therapy data retrieved from IMD 16 during the course of therapy, such as bioelectrical brain signals 94 sensed by IMD 16. The clinician may use this therapy data to determine the progression of the patient condition in order to predict future treatment. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Sense and stimulation electrode combinations 90 stores sense electrode combinations and associated stimulation electrode combinations. As described above, in some examples, the sense and stimulation electrode combinations may include the same subset of electrodes 24, 26, or may include different subsets of electrodes. Thus, memory 82 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 80 or a processor of another device (e.g., IMD 16).

In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 28 in order to mitigate any irregular oscillations or other irregular brain activity within the tissue site associated with the sense electrode combination. In another example, stimulation may be delivered via a stimulation electrode combination to a tissue site that is different than the tissue site closest to the corresponding sense electrode combination but is within the same pathway or brain circuit, e.g., IMD 16 may sense bioelectrical brain signals in the GPi and stimulate in the STN of brain 28 in order to mitigate any abnormal oscillatory activity or other abnormal brain activity within the tissue site associated within the sense electrode combination. The regions of the brain circuit may be functionally related to one another via neurological pathways in a manner that causes activity within one region of the network to be influenced by activity within another region of the network.

Memory 82 also stores an algorithm that processor 80 may execute in order to determine which electrodes from a sense electrode combination are, for example, closest to a target tissue site for stimulation therapy to manage a particular patient. As described in further detail below with respect to FIGS. 12 and 13, in some cases, the target tissue site is a tissue site within brain 28 that exhibits a high relative beta band power level based on bioelectrical signals measured by the sense electrode combination. However, the specific frequency band that is revealing of the target tissue site can differ depending on the anatomical region of brain 28 in which leads are implanted (e.g., the thalamus, anterior nucleus, and the like) or based on the patient condition. Different frequency bands may be biomarkers for different patient conditions. Thus, the algorithm with which processor 80 determines which electrodes 24, 26 are closest to a target tissue site can rely on different frequency band characteristics of a sensed bioelectrical brain signal.

Physiological model data 92 stores information with which processor 80 of programmer 14 generates a physiological model that indicates one or more characteristics of tissue proximate leads 20. In some examples, the characteristics of the tissue include one or more anatomical structures within brain 28 of patient 12 proximate implanted leads 20. In some examples, physiological model data 92 stores lead placement information that identifies a location of leads 20, which can be an actual location of leads 20 within brain 28 or an approximate location of leads 20 within brain 28. The information relating to the actual location of leads 20 can include, for example, a medical image generated using any suitable imaging modality (e.g., CT, MRI, x-ray or fluoroscopy), the stereotactic coordinates used to implant leads 20 within brain 28. Information indicating an approximate location of leads 20 can include, for example, stereotactic coordinates or other 3D coordinates provided by a clinician, whereby the coordinates were not used to implant leads 20 within brain 28 but are provided as a reference point for an estimated implant location of leads 20, correlations of signals sensed by IMD 16 with anatomical structures expected to yield those signals, or correlations of stimulation effects at electrodes with anatomical structures expected to yield those effects.

Physiological model data 92 also stores patient anatomy data, which indicates one or more characteristics of patient tissue proximate to implanted leads 20 and/or one or more anatomical structures of brain 28 proximate implanted leads 20. In some examples, the patient anatomy data includes at least one of an anatomical image of patient 12, a reference anatomical image not specifically based on patient 12, an anatomical atlas (e.g., a non-image, schematic drawing, such as a computer generated drawing, illustrating at least a portion of a human brain proximate the expected lead implant location) or a tissue conductivity data set. The patient anatomy data may be specific to patient 12 or may represent data for more than one patient, e.g., model or averaged data of the anatomical structure and tissue conductivity of multiple patients. For example, in some examples, the patient anatomy data may include tissue conductivity data or other relevant tissue data that is typical for the particular lead 20 location for the particular therapeutic application (e.g., deep brain stimulation in the case of FIG. 1), and may be, but need not be, specific to patient 12. The tissue conductivity data set can indicate, for example, the conductivity of tissue at specific points or regions of brain 28 of patient 12.

In some examples, patient anatomy data may also include expected bioelectrical brain signals or biomarkers associated with specific anatomical structures. Processor 80 may determine whether an electrode is positioned at a target tissue site based on a bioelectrical signal sensed with the electrode by comparing the bioelectrical brain signal to the expected bioelectrical brain signals or biomarkers associated with specific anatomical structures of brain 28.

In addition to or instead of the patient anatomy data, physiological model data 92 can store one or more algorithms for implementation by processor 80 for generating a physiological model. In examples in which the physiological model indicates a tissue site within brain 28 proximate the implanted electrodes 24, 26 of leads 20, the algorithm can include, for example, instructions with which processor 80 identifies the one or more anatomical structures of brain 28 based on the information identifying a location of leads 20 and the patient anatomy data. For example, the algorithm can specify the steps with which processor 80 correlates the location of leads 20 to a coordinate system of brain 28 to determine the one or more anatomical structures of brain 28 proximate electrodes 24, 26 of leads 20, where the anatomical structures of brain 28 are associated with specific coordinates.

The algorithm stored by physiological model data 92 can further cause processor 80 to display a graphical representation of the one or more anatomical structures of brain 28 proximate electrodes 24, 26. In some examples, the graphical representation can also include a representation of leads 20 and/or electrodes 24, 26. In these examples, the algorithm stored by memory 82 can include, for example, instructions with which processor 80 positions leads 20 proximate one or more anatomical structures of brain 28 based on the information identifying a location of leads 20 and the patient anatomy data. For example, the algorithm can specify the steps with which processor 80 correlates the location of leads 20 to a coordinate system associated with the one or more anatomical structures of brain 28, and generates a graphical user interface with the anatomical structures, where the graphical user interface is presented to the user (e.g., a clinician) via a display of user interface 84.

In addition to or instead of the patient anatomy data, physiological model data 92 can store one or more algorithms for implementation by processor 80 for generating a therapy field model. As discussed above, a therapy field model can indicate the electrical field, activation field, voltage gradient or current density of the electrical field resulting from delivery of stimulation via a specific stimulation electrode combination (e.g., a subset of electrodes 24, 26). Physiological model data 92 can store the patient anatomy data that is used to generate an electrical field model. Processor 80 can generate an electrical field model based upon patient anatomy data and a therapy program defining stimulation parameter values, where the electrical field model represents where electrical stimulation propagates through tissue from electrodes 24, 26 of leads 20A, 20B, respectively. The patient anatomy data may include a tissue conductivity data set created from any type of imaging modality, such as, but not limited to, CT, MRI, x-ray, fluoroscopy, and the like. The patient anatomy data may be specific to patient 12 or may represent data for more than one patient, e.g., model or averaged data of the anatomical structure and tissue conductivity of multiple patients.

Processor 80 can also use the stored tissue conductivity data set to generate a therapy field model that includes a current density or voltage gradient map, which provides further details on how electrical stimulation propagates through tissue from electrodes 24, 26 of leads 20A, 20B, respectively.

In addition to or instead of the information used to generate an electrical field model, in other examples, physiological model data 92 can store information with which processor 80 generates an activation field model. An activation field model is generated based on a neuron model that indicates one or more characteristics of patient neural tissue proximate to electrodes 24, 26 of implanted leads 20A, 20B, respectively. The activation field model can indicate the neurons that will be activated by the electrical field in the anatomical region. Processor 80, alone or with the aid of the clinician, can select stimulation electrodes for a particular patient 12 and patient condition by selecting the electrodes that deliver stimulation to patient 12 to activate the desired neurons and substantially avoid activating other neurons (e.g., neurons associated with anatomical structures may result in one or more stimulation-induced side effects).

While the examples of therapy system 10 described herein primarily refer to examples in which sense and stimulation electrode combinations 90, physiological model data 92, and bioelectrical brain signals 94 are stored by memory 80 of programmer 14, the techniques, devices, and systems described herein are also applicable to examples of therapy system 10 in which sense and stimulation electrode combinations 90, physiological model data 92, and/or bioelectrical brain signals 94 can be stored by memory 42 (FIG. 2) of IMD 16 or a memory of another device, such as a remote database, in addition to or instead of being stored by memory 80 of programmer 14.

Wireless telemetry in programmer 14 may be accomplished by RF communication or proximal inductive interaction of external programmer 14 with IMD 16. This wireless communication is possible through the use of telemetry module 86. Accordingly, telemetry module 86 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 delivers operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 88 may include circuitry to monitor power remaining within a battery. In this manner, user interface 84 may provide a current battery level indicator or low battery level indicator when the battery needs to be replaced or recharged. In some cases, power source 88 may be capable of estimating the remaining time of operation using the current battery.

Figure 5:
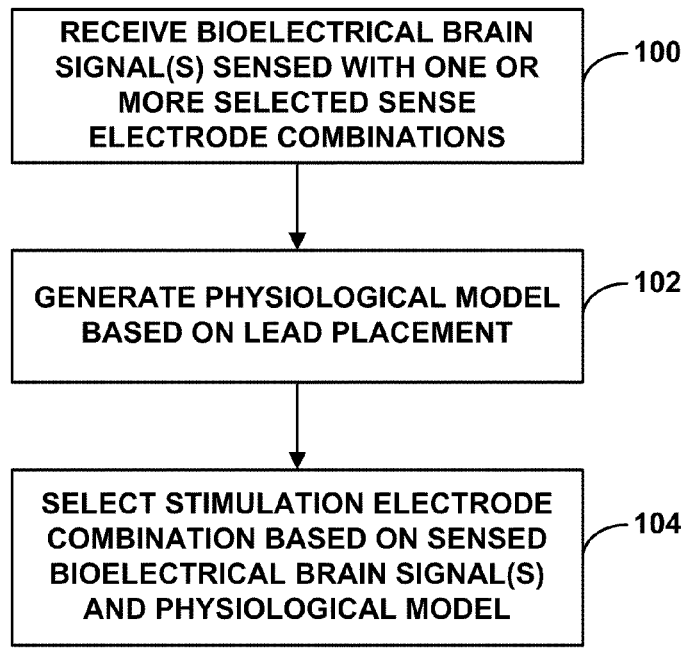
FIG. 5 is a flow diagram illustrating an example technique for selecting a stimulation electrode combination based on a bioelectrical signal sensed via a sense electrode combination and a physiological model that is determined based on placement of the lead within the brain of the patient.

FIG. 5 is a flow diagram illustrating an example technique for selecting a stimulation electrode combination. The techniques shown in FIG. 5, as well as FIGS. 6-13, 15A-15C, 16, and 17, are described as being implemented by processor 80 of programmer 14 alone, processor 40 of programmer 14 alone, or a combination of processors 40, 80. In other examples, one of processor 40, 80, a processor of another device or any combination of processors can implement the techniques shown in FIGS. 5-13, 15A-15C, 16, and 17.

In the technique shown in FIG. 5, processor 80 receives at least one bioelectrical brain signal sensed by IMD 16 or another sensing device (e.g., an external sensing device, such as a microelectrode recorder) with one or more selected sense electrode combinations (e.g., a plurality of bioelectrical brain signal sensed with a respective sense electrode combination) (100). The sense electrode combination includes a respective subset of electrodes 24, 26 (FIG. 2) and, in some examples, another electrode, e.g., on an outer housing of IMD 16. In some examples, sensing module 46 of IMD 16 senses a bioelectrical brain signal in a unipolar configuration in which sensing module 46 senses the bioelectrical brain signal with a first electrode positioned on a lead 20A or 20B and a reference electrode (e.g., an electrode on an outer housing of IMD 16) positioned relatively far from the first electrode. In addition to or instead of the unipolar configuration, sensing module 46 senses a bioelectrical brain signal in a bipolar configuration, e.g., with two or more electrodes 24, 26 of leads 20A, 20B. Processor 40 of IMD 16 transmits the one or more sensed bioelectrical brain signals (e.g., the raw signals, parameterized signals or other data determined based on the raw bioelectrical brain signals) to processor 80 of programmer 14 via the respective telemetry modules 50, 86.

Processor 80 generates a physiological model based on the placement of leads 20 (or electrodes 24, 26) within brain 28 (102). In some examples, processor 80 generates the physiological model based on physiological model data 92 stored by memory 82 of programmer 14. An example technique that processor 80 can implement to generate the physiological model is described with respect to FIGS. 6 and 7. In other examples, the physiological model may already be generated and processor 80 may access the physiological model from a memory of therapy system 10, which can be, for example, memory 82 of programmer 14, memory 42 of IMD 16 or a memory of another device (e.g., a database remotely located from programmer 14 or IMD 16 that stores one or more physiological models). The physiological model can be generated by processor 80 (e.g., during a time period preceding the time period in which processor 80 selects a stimulation electrode combination) and stored in the memory, or generated by a different computing device and stored in the memory. Processor 80 can select the physiological model from the memory using any suitable technique, such as selecting the physiological model associated with patient 12, the patient condition, the implant site of electrodes 24, 26 within brain 12, or any other suitable factor. In some examples, processor 80 selects the physiological model based on input from a user, which is received via user interface 84.

After generating (or accessing) the physiological model, processor 80 selects a stimulation electrode combination based on the one or more of sensed bioelectrical brain signals and the physiological model (104). As described in further detail below with reference to FIG. 8, in some examples, processor 80 selects a stimulation electrode combination based on one or more of the sensed bioelectrical brain signals and subsequently confirms the stimulation electrode combination selection based on the physiological model.

In other examples, as described below with reference to FIG. 9, processor 80 selects a stimulation electrode combination based on the physiological model and subsequently confirms the stimulation electrode combination selection based on bioelectrical brain signals sensed via the electrodes of the stimulation electrode combination. In addition, in other examples, as described below with reference to FIG. 10, processor 80 generates and displays the physiological model via user interface 84, receives user input selecting a stimulation electrode combination based on the physiological model, and confirms the stimulation electrode combination selection based on one or more of the sensed bioelectrical brain signals.

Figure 6:
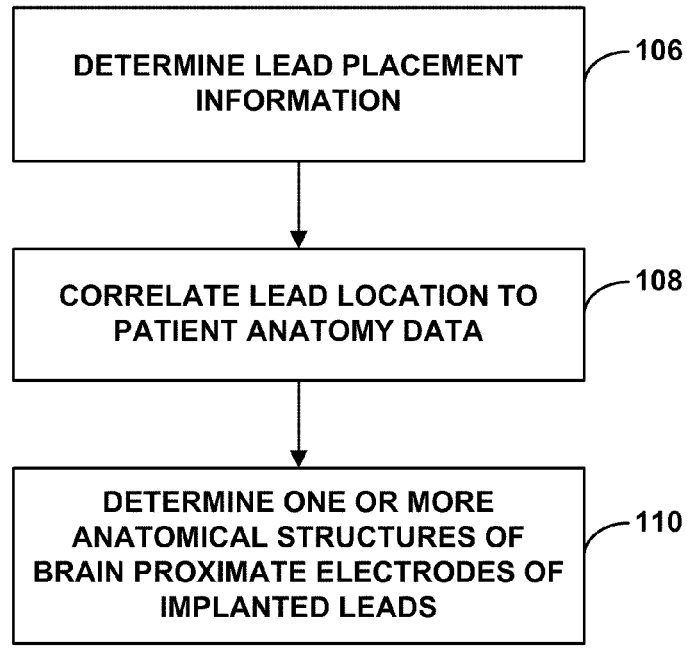
FIG. 6 is a flow diagram illustrating an example technique for generating a physiological model.

FIG. 6 is a flow diagram illustrating an example technique that processor 80 of programmer 14 (or a processor of another device, such as IMD 16) can implement in order to generate a physiological model that indicates the one or more anatomical structures of brain 28 proximate the implanted leads 20. Processor 80 determines lead placement information (106), e.g., based on physiological model data 92 stored by memory 82 of IMD 16. The lead placement information can indicate the actual location of implanted leads 20 within brain 28 of patient 12 or an approximate location of leads 20 within brain 28.

In the example shown in FIG. 6, processor 80 determines the placement of electrodes 24, 26 of leads 20 within brain 28 of patient. For example, processor 80 can determine the stereotactic coordinates used to implant leads 20 within brain 28 or receive input from a clinician via user interface 84 indicating 3D coordinates of electrodes 24, 26 relative to a coordinate system associated with brain 28. The coordinate system can be arbitrarily assigned to brain 28 or can be based on a convention used by one or more clinicians. The coordinates provided by the clinician may not be the coordinates used to implant leads 20 within brain 28, and may instead be an estimated location of electrodes 24, 26.

As another example, processor 80 can determine the location of leads 20 and electrodes 24, 26 carried by leads 20 based on a patient specific medical image of implanted electrodes 24, 26 and the region of brain 28 of patient 12 in which electrodes 24, 26 are implanted. Processor 80 can assign, for example, coordinates to the implanted electrodes 24, 26, whereby the coordinates are based on a coordinate system associated with brain 28 of patient 12. As previously discussed, the location of the one or more anatomical structure of brain 28 can also be indicated by coordinates associated with the coordinate system. In this way, the coordinates of implanted electrodes 24, 26 can indicates the location of electrodes 24, 26 relative to one or more anatomical structure of brain 28.

Processor 80 correlates the location of leads 20 indicated by the lead placement information to patient anatomy data stored by memory 82 (108). For example, processor 80 can reference the patient anatomy data stored by memory 82 and map the stereotactic coordinates of leads 20 (e.g., electrodes 24, 26) or another set of 3D coordinates (e.g., inputted by a clinician) to the patient anatomy data. The patient anatomy data can be, for example, a medical image of brain 28 of patient 12, an image of a brain of a patient other than patient 12, a reference medical image not specifically based on patient 12, an anatomical atlas that is not specific to patient 12, or another data set that indicates the locations of anatomical structures of brain 28 of patient 12. In examples in which processor 80 determines lead placement information based on a medical image of implanted electrodes 24, 26 and brain 28, the medical image can correlate the lead location to patient anatomy data.

After correlating the location of leads 20 to patient anatomy data (108), processor 80 determines the one or more anatomical structures of brain 28 proximate the electrodes 24, 26 of implanted leads 20 (110). For example, after mapping stereotactic or other coordinates of leads 20 to a medical image or another data set, processor 80 can identify the one or more anatomical structures of brain 28 proximate electrodes 24, 26 within the medical image or other data set. In examples in which processor 80 determines lead placement information based on a medical image of implanted electrodes 24, 26 and brain 28, processor 80 can reference the medical image to determine the one or more anatomical structures of brain 28 proximate electrodes 24, 26. For example, processor 80 can utilize template matching to identify, within the medical image, the one or more anatomical structures of brain 28 proximate electrodes 24, 26. The template can be, for example, an anatomical atlas that provides a map of the anatomical structures within brain 28. As another example, processor 80 can reference data that indicates the coordinates of the one or more anatomical structures of brain 28 and compare the coordinates of leads 20 to the coordinates of the one or more anatomical structures of brain 28 to determine the one or more anatomical structures proximate implanted leads 20.

In some examples, processor 80 may determine the one or more anatomical structures of brain 28 proximate the electrodes 24, 26 of implanted leads 20 based on a bioelectrical brain signal sensed with electrodes 24, 26. As discussed above, in some examples, memory 82 (FIG. 4) of programmer 14 can store patient anatomy data, such as a bioelectrical brain signal characteristic or other biomarker that is expected to be sensed at a particular anatomical structure within brain 28. Processor 80 may compare the bioelectrical brain signal sensed with some or all of electrodes 24, 26 to the stored patient anatomy data to determine the one or more anatomical structures of brain 28 proximate the electrodes 24, 26 of implanted leads 20.

Processor 80 can store the one or more anatomical structures of brain 28 proximate the electrodes 24, 26 within memory 82. In other examples, processor 80 can display a graphical user interface via user interface 84 that provides a graphical representation of the one or more anatomical structures of brain 28 proximate the electrodes 24, 26, and, in some examples, also includes a graphical representation of the electrodes 24, 26. The display generated and presented by programmer 14 can help the clinician visualize the placement of electrodes 24, 26 within brain 28 of patient 12.

In some examples, a physiological model includes a therapy field model that indicates the therapy field that may result from delivering stimulation to patient 12 via a selected stimulation electrode combination and a specific electrode combination. Thus, in some examples, processor 80 generates a physiological model by implementing an algorithm for generating a therapy field model. Electrical current from an electrode propagates in all directions from the active electrode. The resulting therapy field reaches anatomical regions of brain 28 within a certain distance in all directions. A therapy field may reach the target anatomical region, but the therapy field may also affect non-target anatomical regions and produce unwanted side effects. By generating a therapy field model, processor 80 can determine whether a therapy field reaches a target anatomical region of brain 28 and/or affects anatomical regions of brain 28 associated with stimulation-induced side effects.

Figure 7:
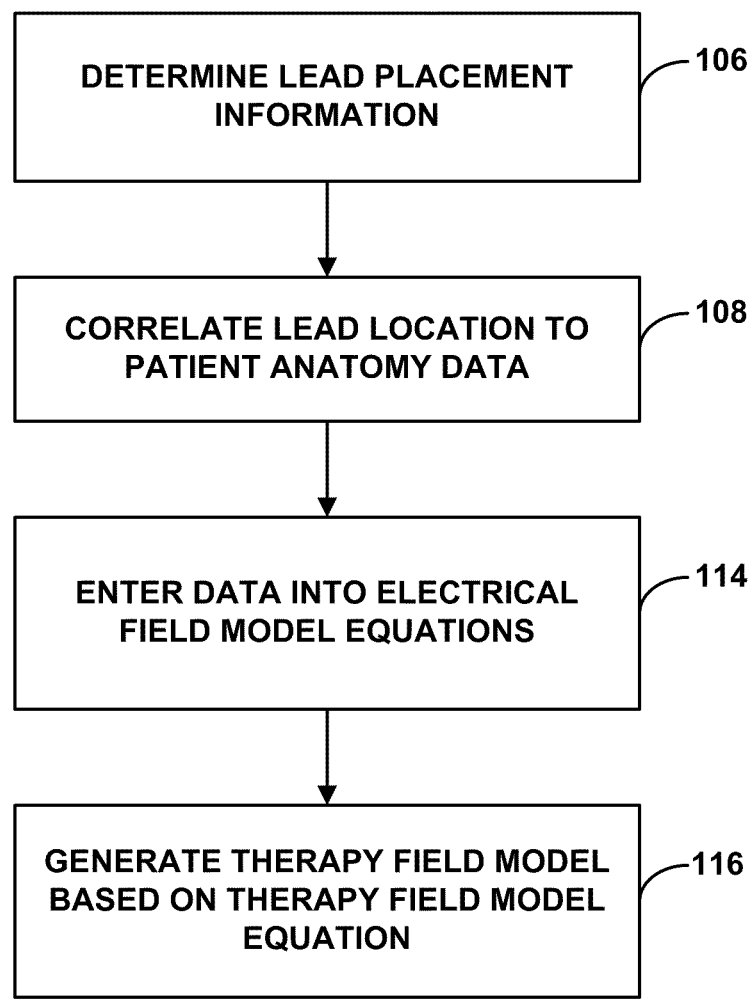
FIG. 7 is a flow diagram illustrating an example technique for generating a physiological model that includes a therapy field model.

FIG. 7 is a flow diagram illustrating an example technique with which processor 80 can generate a physiological model that includes a therapy field model, which indicates where the electrical stimulation delivered via a selected subset of electrodes 24, 26 will propagate within brain 28. In the technique shown in FIG. 7, processor 80 determines lead placement information (106) and correlates the location of leads 20 to patient anatomy data (108). Processor 80 enters the patient anatomy data in a therapy field model equation that defines how the electrical stimulation affects tissue within brain 28 (114) and generates the therapy field model based on the equation (116). The one or more therapy field model equations can be stored in memory 82 of programmer 14 or a memory of another device (e.g., IMD 16).

For example, the therapy field model equation can be an electrical field model equation that defines how an electrical field propagates away from an origin location (e.g., a specific electrode) with a specific set of stimulation parameter values (e.g., current or voltage amplitude, electrode combination, frequency, and the like). The stimulation parameter values that are inputted into the electrical field model equation (or other therapy field model equation) can be inputted by a user (e.g., a clinician) or may be stored by memory 82 of programmer 14 or another device. The electrical field model equation may be specific to or customized for patient 12. One variable of the electrical field model equation is the physical tissue characteristics of the tissue adjacent leads 20, which is included in the patient anatomy data set stored by programmer 14. From this information, processor 80 is able to generate the estimated electrical field that will be produced in therapy. Example physical tissue characteristics include, but are not limited to, any one or more of tissue conductivity or tissue impedance values.

As another example, the therapy field model equation can be a voltage gradient or current density model equation with which processor 80 determines the voltage gradient or current density of an electrical field generated when stimulation is delivered via a selected subset of electrodes 24, 26 and with a particular set of stimulation parameter values. For example, processor 80 can enter tissue conductivity or impedance values for the tissue proximate the implanted electrodes 24, 26 into the voltage gradient or current density model equation, which provides a mathematical formula that represents how the stimulation signal propagates through the tissue. In some examples, processor 80 controls IMD 16 to sense the tissue conductivity or impedance values for the tissue proximate the implanted electrodes 24, 26. Processor 80 can then determine the voltage gradient or current density of an electrical field generated by electrical stimulation delivered signals via electrodes 24, 26 based on the tissue conductivity values and the voltage gradient or current density model equation.

As another example, the therapy field model equation can be an activation field model equation that defines how a neuron model fits to the electrical field model. Processor 80 can determine an activation field model based upon the electrical field model and neuron model. The neuron model may be a set of equations, a lookup table, or another type of model that defines threshold action potentials of particular neurons that make up the anatomical structure, as defined by the patient anatomy data, affected by the electrical field determined based on the electrical field model equation. The neuron model can be generated based on information specific to patient 12 or non-specific to patient 12. If the voltage or current amplitude of the electrical field is above the threshold of any neuron within the electrical field, that neuron will be activated, e.g., cause a nerve impulse. In some examples, processor 80 can generate a graphical user interface that includes a graphical representation of the electrical field model, the activation field model, and/or the voltage gradient or current density of an electrical field.

In some examples, processor 80 may confirm the equations or parameters (e.g., tissue conductivity values) with which processor 80 generates a therapy field model by controlling IMD 16 to deliver stimulation via the selected stimulation parameter values and electrode combination, generating a therapy field model using the therapy field model equation, and then controlling IMD 16 to sense with electrodes to determine whether the expected therapy field values are indeed achieved. If the same electrodes that delivered the stimulation are used to sense the electrical field resulting from the delivery of stimulation, there may be a time delay following the delivery of stimulation before the electrodes sense a signal.

The electrodes that are used to sense the electrical field can sense the local field potential (e.g., a voltage value) and processor 80 can compare the local field potential values to ones expected given the therapy field model predictions. Processor 80 may, in some examples, control sensing module 46 of IMD 16 to sense bioelectrical brain signals with some or all electrodes 24, 26 in a unipolar configuration or subset of pairs of electrodes 24, 26, post-process the signals if necessary (e.g. extract a power band or power spectrum), and compare the results to the therapy model predictions. Processor 80 can determine, for example, whether the sensed bioelectrical brain signals indicate the correct electrode(s) are being activated by the delivery of stimulation according to the selected electrode combination and other stimulation parameter values.

If the expected therapy field values are not achieved, processor 80 can modify parameters of the therapy field model (tissue conductivity values, etc) or the equation until the expected therapy field values are achieved. In some examples, processor 80 can control stimulation generator 44 of IMD 16 to deliver a stimulation signal that sweeps through a frequency range, and the frequency response (e.g., power spectral density) may be measured at other, non-stimulation delivering electrodes to yield complex impedances (e.g., inductive or capacitive aspects) of the tissue, in addition to simple conductivities. These complex impedances can then be used to update the parameters of the therapy field model.

Example devices, systems, and techniques for generating therapy field models, such as electrical field models, activation field models, and voltage gradient or current density models, are described in commonly-assigned U.S. Patent Application Publication No. 2007/0203546 by Stone et al., entitled, "ELECTRICAL AND ACTIVATION FIELD MODELS FOR CONFIGURING STIMULATION THERAPY" and filed on Oct. 31, 2006, and commonly-assigned U.S. Patent Application Serial No. 2007/0203541 by Goetz et al., entitled, "PROGRAMMING INTERFACE WITH A CROSS-SECTIONAL VIEW OF A STIMULATION LEAD WITH COMPLEX ELECTRODE ARRAY GEOMETRY," and filed on Oct. 31, 2006. The entire content of U.S. Patent Application Publication Nos. 2007/0203546 and 2007/0203541 is incorporated herein by reference.

In accordance with techniques described in U.S. Patent Application Publication No. 2007/0203541 by Goetz et al., programmer 14 may present a user interface that displays electrodes of leads 20 and enables a user to select individual electrodes to form a stimulation electrode combination and specify parameters for stimulation delivered via the electrode combination. U.S. Patent Application Serial No. 2007/0203541 also describes programming methods and systems that display different therapy field models and are configured to receive user input manipulating a therapy field (e.g., manipulating a therapy field, such as an electrical or activation field, in terms of size, direction and shape) in order to adjust one or more stimulation parameter values. In accordance with some systems and techniques described by U.S. Patent Application Serial No. 2007/0203541 by Goetz et al., after selecting an electrode combination, a clinician can interact with a graphical representation of the therapy field presented by programmer 14 in order to select or otherwise adjust one or more other stimulation parameter values, such as the amplitude or frequency of the stimulation signal.

Figure 8:
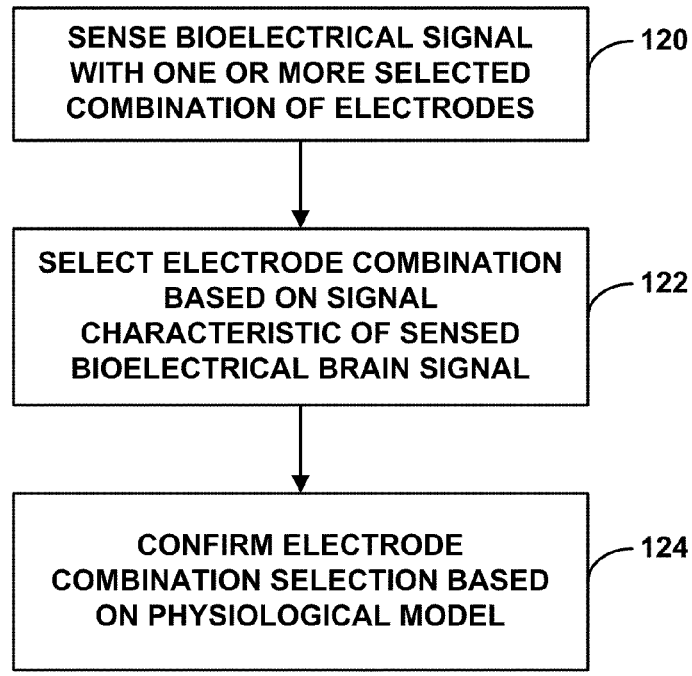
FIGS. 8-10 are flow diagrams illustrating example techniques for selecting a stimulation electrode combination based on a bioelectrical brain signal and physiological model.

FIG. 8 is a flow diagram illustrating an example technique with which a stimulation electrode combination can be selected based on one or more sensed bioelectrical brain signals and a physiological model that indicates one or more anatomical structures of brain 28 proximate implanted electrodes 24, 26. Processor 40 of IMD 16 controls sensing module 46 to sense one or more bioelectrical brain signals with one or more selected combination of electrodes (120). For example, switch module 48 (FIG. 3), under the control of processor 40, may selectively couple sensing module 46 to a first subset of electrodes 24, 26, and sensing module 46 may sense a first local field potential within brain 28 via the first subset of electrodes 24, 26. This first subset of electrodes may also be referred to as a first sense electrode combination. Processor 40 may store the first bioelectrical brain signal resulting from the measurement of the first local field potential within brain 28 via the first subset of electrodes 24, 26 within memory 42 of IMD 16.

In examples in which sensing module 46 senses a plurality of bioelectrical brain signals, switch module 48 may subsequently selectively couple sensing module 46 to a second subset of electrodes 24, 26, i.e., a second sense electrode combination, which differs from the first subset by at least one electrode. Sensing module 46 may sense a local field potential within brain 28 via the second subset of electrodes 24, 26. Processor 40 may store the second bioelectrical brain signal resulting from the measurement of the local field potential within brain 28 via the second subset of electrodes 24, 26 within bioelectrical brain signals 60 of memory 42 of IMD 16. Processor 40 may continue sensing bioelectrical brain signals within brain 28 with any suitable number of sense electrode combinations. The sense electrode combinations may be stored in memory 42 of IMD 16 or a memory of another device. In the example shown in FIG. 8, processor 40 transmits the sensed bioelectrical brain signals to programmer 14 via the respective telemetry module 50, 86 of IMD 16 and programmer 14.

Processor 80 of programmer 14 selects a stimulation electrode combination based on a signal characteristic of a sensed bioelectrical brain signal (122). For example, processor 80 can select a sense electrode combination as the stimulation electrode combination or processor 80 can select the stimulation electrode combination by referencing memory 82 and determining which stimulation electrode combination is associated with a selected sense electrode combination, as described above with respect to FIG. 3. Processor 80 can, for example, select the stimulation electrode combination associated with a sense electrode combination with which sensing module 46 of IMD 16 sensed a bioelectrical brain signal exhibiting a certain signal characteristic (e.g., a potential or frequency domain characteristic).

As an example, processor 80 can select the stimulation electrode combination associated with a sense electrode combination with which sensing module 46 of IMD 16 sensed a bioelectrical brain signal having a mean, median, peak or lowest amplitude greater or less than a predetermined threshold value. The threshold value can be stored in memory 82 of programmer 14 or a memory of another device, such as IMD 16. As another example, processor 80 can select the stimulation electrode combination associated with a sense electrode combination with which sensing module 46 of IMD 16 sensed a bioelectrical brain signal having a pattern (e.g., a time domain pattern) substantially correlating (e.g., a 100% match may not be required, but may be within a threshold percentage, such as about a 75% to about a 100% match) to a template stored by programmer 14. In other examples, processor 80 can select the stimulation electrode combination associated with a sense electrode combination with which sensing module 46 of IMD 16 sensed a bioelectrical brain signal having a particular number of spikes within a particular time frame. In addition, in other examples, processor 80 can select the stimulation electrode combination based on the one or more sense electrodes with which the bioelectrical brain signal having a variability that matches or substantially matches (e.g., is within a threshold percentage, such as about 1% to about 25%) a predetermined threshold variability was sensed.

As another example, processor 80 can select the stimulation electrode combination associated with a sense electrode combination with which sensing module 46 of IMD 16 sensed a bioelectrical brain signal having a frequency domain characteristic greater than or less than a predetermined threshold value or a signal that substantially matches a template. The template can be predetermined and stored in memory 82 of programmer 14 or a memory of another device, such as IMD 16.

In examples in which processor 80 selects a stimulation electrode combination based on a plurality of bioelectrical brain signals sensed via respective sense electrode combinations, processor 80 can select one of the sense electrode combinations based on the values of a signal characteristic (e.g., a time domain characteristic or a frequency domain characteristic) of each of the sensed signals. For example, processor 80 may determine a plurality of relative values of a frequency domain characteristic based on a plurality of sensed bioelectrical brain signals, compare the relative values of a plurality of sense electrode combinations, and determine the sense electrode or electrodes that are located closest to the target tissue site based on the relative values. Techniques for selecting a stimulation electrode combination based on a plurality of bioelectrical brain signals sensed via respective sense electrode combinations are described below with reference to FIGS. 12, 13, 15A-15C, 16, and 17. A frequency domain characteristic of the biosignal may include, for example, a power level (or energy) within one or more frequency bands of the biosignal, a ratio of the power level in two or more frequency bands, a correlation in change of power between two or more frequency bands, a pattern in the power level of one or more frequency bands over time, and the like.

In some examples, processor 80 selects the stimulation electrode combination associated with one or more sense electrodes that are closest to a target tissue site. This may, in some patients with movement disorders, be indicated by a bioelectrical signal comprising the highest relative beta band power level compared to the other sensed bioelectrical brain signals. In other examples, processor 40 may select a stimulation electrode combination that is associated with the sense electrode combination that is closest to a target tissue site, as indicated by a bioelectrical brain signal comprising a power level in a particular frequency band above a threshold value, which may be stored in memory 82 of programmer 14 or a memory of another device, such as IMD 16.

In some examples, processor 80 implements an algorithm stored by memory 82 of programmer 14 in order to determine which individual sense electrodes are located closest to a target tissue site, e.g., a region of brain 28 that exhibits a bioelectrical signal with the highest relative beta band power level. Processor 80 may then select a stimulation electrode combination based on determining which sense electrodes are located closest to the target tissue site in order to provide the most effective stimulation therapy to brain 28. In some examples, memory 82 of programmer 14 stores an algorithm that includes instructions that cause processor 40 to evaluate the relative beta band power levels for a plurality of bioelectrical signals sensed by a respective one of a plurality of sense electrode combinations and determine which sense electrode combination is closest to the target tissue site with the highest relative beta band power level. Processor 80 can then select the stimulation electrode combination based on the sense electrode combination associated with a bioelectrical signal having the highest relative beta band power level.

After selecting a stimulation electrode combination based on a signal characteristic of one or more sensed bioelectrical brain signals (122), processor 80 of programmer 14 confirms the stimulation electrode combination selection based on a physiological model (124). The physiological model generated by processor 80 indicates the position of the subset of electrodes 24, 26 of the stimulation electrode combination relative to one or more anatomical structures of brain 28 of patient 12. Thus, in one example, after mapping at least the subset of electrodes 24, 26 of the selected stimulation electrode combination to patient anatomy data that indicates the anatomical structures of brain 28, processor 80 determines whether the physiological model indicates the subset of electrodes 24, 26 of the selected stimulation electrode combination are proximate the target tissue site within brain 28. The target tissue site can be, for example, the tissue site for stimulation signals that effectively manages the patient condition. The anatomical structures of brain 28 of patient 12 that serve as the target tissue site for stimulation delivered by IMD 16 may be selected based on the patient condition. For example, stimulating an anatomical region such as the substantia nigra in brain 28 may reduce the number and magnitude of tremors experienced by patient 12. Other target anatomical regions for treatment of movement disorders may include the subthalamic nucleus, globus pallidus interna, ventral intermediate, and zona incerta.

Processor 80 can determine whether the physiological model indicates the subset of electrodes 24, 26 of the selected stimulation electrode combination are proximate the target tissue site within brain 28 using any suitable technique. In one example, processor 80 approximates a distance between electrodes 24, 26 of the selected stimulation electrode combination and the target tissue site within brain 28, which can be stored by memory 82 of programmer 14 and/or inputted by a clinician. In another example, processor 80 merely determines whether the subset of electrodes 24, 26 of the selected stimulation electrode combination are directly adjacent the target tissue site within brain 28, or whether the subset of electrodes 24, 26 are separated from the target tissue site by another anatomical structure. Other techniques are also contemplated.

As discussed above, the patient anatomy data can include an anatomical image of patient 12, a reference anatomical image not specific to patient 12, or an anatomical atlas. Thus, in some examples, processor 80 merely confirms that the location of the electrodes of the selected stimulation electrode combination is in the approximate region of the target tissue site. In examples in which the physiological model is generated based on an anatomical image of patient 12, processor 80 can more accurately determine that electrodes of the selected stimulation electrode combination are positioned to deliver stimulation to the target tissue site.

In examples in which the physiological model indicates a therapy field model, processor 80 can confirm the stimulation electrode combination selection based on the location of the therapy field relative to the target tissue site and/or the tissue site associated with stimulation-induced side effects. Processor 80 can generate the therapy field model based on the selected stimulation electrode combination. For example, processor 80 can determine the electrical or activation field that results when stimulation is delivered via the selected stimulation electrode combination and a predetermined set of other stimulation parameter values (e.g., stimulation signal frequency, amplitude, and the like).

After determining the size, location, and other characteristics of the therapy field, processor 80 can determine whether the therapy field overlaps with a physiologically significant location within brain 28. The physiologically significant location can be, for example, a target tissue site or the tissue site associated with stimulation-induced side effects. The overlapping (e.g., overlays or otherwise is positioned in the same region) of the therapy field with the target tissue site can indicate that the selected stimulation electrode combination is useful for delivering stimulation to the target tissue sites. Thus, if processor 80 determines that the therapy field model resulting from stimulation delivery via the selected stimulation electrode combination overlaps with the target tissue site, processor 80 can confirm the selected stimulation electrode combination (124).

On the other hand, if processor 80 determines that the therapy field resulting from stimulation delivery via the selected stimulation electrode combination does not substantially overlap with the target tissue site, processor 80 may not confirm the selected stimulation electrode combination and generate an indication that the physiological model indicates the selected stimulation electrode combination may not provide efficacious stimulation therapy. The indication can be presented to a user via user interface 84 of programmer 14 or another device, or can be a signal, flag or value stored by processor 80 in memory 82 of programmer 14 and associated with the selected stimulation electrode combination.

The physiologically significant location within brain 28 can also include one or more anatomical structures of brain 28 associated with stimulation-induced side effects. That is, a region within brain 28 can be considered physiologically significant if stimulation delivery to that region results in one or more stimulation-induced side effects perceived by patient 12 or otherwise affecting patient 12. In some examples, the clinician provides input identifying one or more anatomical structures of brain 28 associated with stimulation-induced side effects. In other examples, processor 80 determines the one or more anatomical structures of brain 28 associated with stimulation-induced side effects by accessing a database, which may be stored by memory 82 of programmer or a memory of another device (e.g., a remote database), which may identify such anatomical structures and associate the anatomical structures with the patient condition. The anatomical structures may be identified within a patient anatomy model or atlas.

Thus, in some examples, in addition to or instead of determining whether the therapy field resulting from stimulation delivery via the selected stimulation electrode combination overlaps with the target tissue sites, processor 80 can determine whether the therapy field overlaps with a tissue site associated with a stimulation-induced side effect. If processor 80 determines that the therapy field resulting from stimulation delivery via the selected stimulation electrode combination does not substantially overlap with the tissue site associated with a stimulation-induced side effect, processor 80 can confirm the selected stimulation electrode combination (124).

On the other hand, if processor 80 determines that the therapy field resulting from stimulation delivery via the selected stimulation electrode combination overlaps with the tissue site associated with a stimulation-induced side effect, processor 80 may not confirm the selected stimulation electrode combination and generate an indication that the physiological model indicates the selected stimulation electrode combination may result in one or more stimulation-induced side effects. The indication can be presented to a user via user interface 84 of programmer 14 or another device, or can be a signal, flag or value stored by processor 80 in memory 82 of programmer 14 and associated with the selected stimulation electrode combination.

While DBS may successfully reduce symptoms of some neurological conditions, the stimulation may cause unwanted side effects as well. Side effects may include muscle contractions, cognitive deficits, ocular disturbances, mood changes, incontinence, tingling, loss of balance, paralysis, slurred speech, loss of memory, and many other neurological problems. Side effects may be mild to severe; however, most side effects are reversible when stimulation is stopped. DBS may cause one or more side effects by inadvertently providing electrical stimulation to anatomical regions near the targeted anatomical region. For this reason, programmer 14 that includes processor 80 that automatically evaluates whether a particular stimulation electrode combination is positioned to deliver stimulation that may generate one or more side effects can be useful for programming efficacious stimulation therapy for patient 12.

In some examples, processor 80 confirms the stimulation electrode combination selection based on both the one or more anatomical structures proximate the electrodes of the selected stimulation electrode combination and the therapy field model, although only one type information ascertained from the physiological model can be used to confirm the stimulation electrode selection.

In other examples of the technique shown in FIG. 8, a clinician, with the aid of a graphical user interface that presents a physiological model, confirms the selected electrode combination based on the physiological model. Processor 80 can display both the anatomical structures of brain 28 of patient 12 proximate implanted electrodes 24, 26 and at least the electrodes of the selected electrode combination. In some examples, the clinician can determine, based on the graphical display of the anatomical structures of brain 28 of patient 12 and the electrodes of the selected electrode combination, whether the electrodes of the selected electrode combination are proximate the target tissue site or proximate a tissue site associated with a stimulation-induced side effect.

In other examples, processor 80 can also display a graphical representation of a therapy field (e.g., as shown with respect to FIG. 18) via a display of user interface 84 in addition to or instead of the electrodes of the selected stimulation electrode combination. The clinician can determine, based on the graphical display of the therapy field, whether the therapy field resulting from delivery of stimulation according to the selected electrode combination overlaps with the target tissue site or the tissue site associated with a stimulation-induced side effect. In these examples, processor 80 may or may not display the anatomical structures of brain 28 in addition to the therapy field. Because processor 80 generates the therapy field model based on patient anatomy data, such as tissue conductivity data, the graphical display the therapy field alone may be useful for the clinician to visualize how the therapy delivered via the selected stimulation electrode combination may affect surrounding tissue.

After determining whether the selected stimulation electrode combination is useful, the clinician can provide input (e.g., via one or more input mechanisms of user interface 84 of programmer 14) confirming the selected electrode combination or input indicating that the selected electrode combination should not be programmed as a therapy parameter of IMD 16. Thus, in some examples, processor 80 can confirm the selected stimulation electrode combination based on the physiological model by first displaying the physiological model and subsequently receiving user input confirming or rejecting the stimulation electrode combination selection.

After selecting stimulation electrode combination in accordance the technique shown in FIG. 8, a clinician, alone or with the aid of a computing device, such as programmer 14, may select the other stimulation parameter values that provide efficacious therapy to patient 12. These other stimulation parameter values may include, for example, a frequency and amplitude of stimulation signals, and, in the case of stimulation pulses, a duty cycle and pulse width of the stimulation signals.

Figure 9:
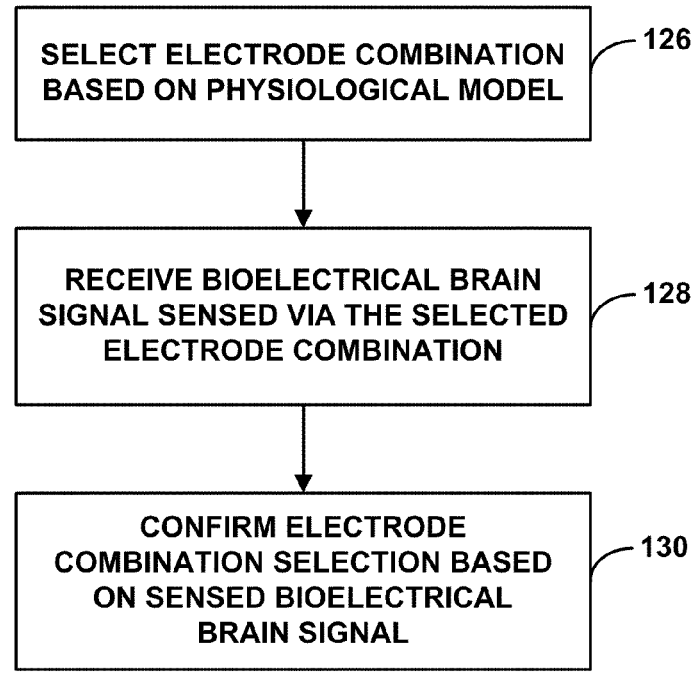

FIG. 9 is a flow diagram illustrating another example technique for selecting stimulation electrodes based on a bioelectrical brain signal and a physiological model that indicates one or more anatomical structures proximate implanted electrodes 24, 26. In the example shown in FIG. 9, processor 80 of programmer 14 generates a physiological model and selects an electrode combination based on the physiological model (126). In some examples, processor 80 selects one or more electrodes that the physiological model indicates are proximate the target tissue site within brain 28 and/or not proximate a tissue site associated with a stimulation-induced side effect. For example, to generate the physiological model, processor 80 can map electrodes 24, 26 of leads 20 to patient anatomy data that indicates the layout of brain 28, and select electrodes proximate the target tissue site within brain 28 as the stimulation electrodes. In examples in which processor 80 accesses a previously generated physiological model from a memory, processor 80 can also can map electrodes 24, 26 of leads 20 to patient anatomy data that indicates the layout of brain 28, and select electrodes proximate the target tissue site within brain 28 as the stimulation electrodes. Proximity of electrodes to the target tissue site can be an indicator of reliable therapeutic efficacy.

Processor 80 can determine the electrodes 24, 26 that are proximate the target tissue site within brain 28 using any suitable technique. In one example, processor 80 approximates a distance between each electrode 24, 26 and the target tissue site within brain 28 and compares the distance to a threshold value. Processor 80 can select the one or more electrodes that are less than the threshold value away from the target tissue site.

Example devices, systems, and techniques for determining a distance between an electrode and an anatomical target are described in U.S. Patent Application Publication No. 2009/0196471 by Goetz et al., which is entitled, "CHARACTERIZATION OF ELECTRICAL STIMULATION ELECTRODES USING POST-IMPLANT IMAGING" and published on Aug. 6, 2009. U.S. Patent Application Publication No. 2009/0196471 by Goetz et al. is incorporated herein by reference in its entirety. Processor 80 can implement any of the techniques described in U.S. Patent Application Publication No. 2009/0196471 by Goetz et al. to determine the electrodes 24, 26 that are proximate the target tissue site within brain 28. For example, processor 80 can perform image analysis of an anatomical image of electrodes 24, 26 and the target tissue site to determine positioning of electrodes relative to anatomical targets. For example, processor 80 can assign an x-axis and a y-axis coordinate origin to a post-implant lead image (e.g., the origin may be the bottom left corner of the image), analyze pixels of the image to identify electrodes and a target tissue site, and establish a pixel to distance dimensional scale to determine actual relative positioning of electrodes and the target tissue site. In some examples, multiple images may be obtained from different perspectives to ascertain the positioning of electrodes relative to the target tissue site in different dimensions.

Information identifying the target tissue site and the tissue site associated with a stimulation-induced side effect can be stored in memory 82 of programmer 14 (or a memory of another device) as, for example, respective templates that correspond to the shape and size of the tissue site within the patient anatomy data. As another example, processor 80 can receive input from a user that identifies the target tissue site or the tissue site associated with a stimulation-induced side effect within a graphical representation of brain 28 displayed by processor 80. As described above, the graphical representation of brain 28 can be an image of brain 28 of a specific patient 12, a patient non-specific image of brain 28, or a non-image graphical representation of brain 28 (e.g., a drawing).

In another example, a plurality of predetermined electrode combinations are stored by memory 82 of programmer 14. Processor 80 can select one or more of the predetermined electrode combinations that are proximate the target tissue site as stimulation electrode combinations. For example, after generating a physiological model that maps electrodes 24, 26 of leads 20 to patient anatomy data that indicates the layout of brain 28, processor 80 can determine a distance between each electrode of a predetermined electrode combination and the target tissue site based on the physiological model. Processor 80 can then select the predetermined electrode combination that has electrodes closest to the target tissue site (e.g., based on a mean or median distance between the electrodes and the target tissue site) or the greatest number of electrodes within a threshold distance of the target tissue site. The threshold distance can be a value, e.g., determined by a clinician, and stored by memory 82 of programmer or a memory of another device.

In another example, processor 80 selects a stimulation electrode combination based on a physiological model that includes a therapy field model. For example, processor 80 can select an electrode combination that results in a therapy field that substantially overlaps with a target tissue site and/or substantially avoids a tissue site associated with a stimulation-induced side effect. In some examples, processor 80 initially selects one electrode combination, determines a therapy field model based on the selected electrode combination, and selects the electrode combination if the therapy field overlaps (e.g., partially or fully) with a target tissue site and/or does not overlap with a tissue site associated with a stimulation-induced side effect. If the initial electrode combination does not satisfy one or both of the criteria, processor 80 can select another electrode combination and compare the therapy field resulting from the delivery of therapy via the selected electrode combination until an electrode combination that satisfies one or both of the criteria is determined.

A plurality of electrode combinations can be stored in memory 82 of programmer 14 (or another device) and processor 80 can generate therapy field models based on each of the electrode combinations until the satisfactory electrode combination is determined. In other examples, the electrode combinations are not predetermined, but, rather are determined by processor 80 during the stimulation electrode selection process, e.g., using an algorithm for selecting an electrode combination. Any suitable algorithm for generating an electrode combination can be used.

As an example, processor 80 can implement a genetic algorithm-based technique, such as the one described in commonly-assigned U.S. Pat. No. 7,239,926 to Goetz et al., entitled, "SELECTION OF NEUROSTIMULATION PARAMETER CONFIGURATIONS USING GENETIC ALGORITHMS," which issued on Jul. 3, 2007. In one example described in U.S. Pat. No. 7,239,926 to Goetz et al., genetic algorithms provide guidance in the selection of stimulation parameters by suggesting the parameters that are most likely to be efficacious given the results of tests already performed during an evaluation session. Genetic algorithms encode potential solutions to a problem as members of a population of solutions. This population is then judged based on a fitness function. The best therapy programs are then retained and a new generation is created based upon their characteristics. The new generation is composed of solutions similar in nature to the best performers of the previous generation.

In accordance with the techniques described in U.S. Pat. No. 7,239,926 to Goetz et al., processor 80 may select a first electrode combination (i.e., the electrodes selected for therapy delivery and the polarities of the selected electrodes) for therapy delivery by IMD 16, generate a therapy field model based on therapy delivery with the first electrode combination and a predetermined set of other stimulation parameter values (e.g., amplitude, frequency, pulse width, and the like), and select a second electrode combination for IMD 16 based on a comparison of the size and location of the therapy field based on therapy delivery with the first electrode combination with the target tissue site and tissue site associated with stimulation-induced side effects. The genetic algorithm may suggest cross-over between different solutions identified by the genetic algorithm or mutation of one or more solutions identified by the genetic algorithm, or random electrode changes.

In other examples, processor 80 initially compares the therapy fields of a plurality of the electrode combinations and selects the electrode combination that is associated with a therapy field model that has the most overlap with the target tissue site and/or the least overlap with the tissue side associated with stimulation-induced side effects. Again, the electrode combinations can be predetermined and stored in memory 82 prior to the programming session or processor 80 can determine the electrode combinations during the stimulation electrode selection process.

In other examples of the technique shown in FIG. 9, a clinician, with the aid of a graphical user interface of a physiological model displayed by programmer 14, selects the electrode combination. The clinician can provide user input via user interface 84 (FIG. 3) indicating the selected electrode combination. Processor 80 receives the user input and selects the electrode combination based on the physiological model and user input (126).

Processor 80 can display both a graphical representation of at least a portion of brain 28 of patient 12 proximate implanted electrodes 24, 26 and at least the electrodes of the selected electrode combination. The graphical representation of at least a portion of brain 28 can be at least one of an anatomical image of a patient, a patient non-specific reference anatomical image, or an anatomical atlas. In some examples, the clinician can determine, based on the graphical display of brain 28 of patient 12 and implanted electrodes 24, 26, which electrodes are proximate the target tissue site or proximate a tissue site associated with a stimulation-induced side effect. The clinician can then select the electrodes that are visually determined to be proximate the target tissue site or proximate a tissue site associated with a side effect.

In other examples, processor 80, automatically or with the aid of user input, can select one or more electrodes 24, 26, and display a graphical representation of a therapy field model (e.g., as shown with respect to FIG. 18) via a display of user interface 84 that indicates a therapy field that results from delivery of stimulation via the one or more selected electrodes and a predetermined set of other stimulation parameter values. The therapy field model can be displayed instead of or in addition to displaying the electrodes 24, 26. The clinician can determine, based on the graphical display of brain 28 of patient 12 and the therapy field model, whether the therapy field resulting from delivery of stimulation according to the selected electrode combination substantially overlaps with the target tissue site or the tissue site associated with a stimulation-induced side effect.

If the therapy field resulting from delivery of stimulation according to the selected electrode combination substantially overlaps with the target tissue site and does not substantially overlap with the tissue site associated with a stimulation-induced side effect, the clinician can provide input via user interface 84 indicating processor 80 should select the electrode combination and confirm the electrode combination based on a bioelectrical brain signal sensed with the electrode combination, as described in further detail below. On the other hand, if the therapy field resulting from delivery of stimulation according to the selected electrode combination either does not substantially overlap with the target tissue site or substantially overlaps with the tissue site associated with a stimulation-induced side effect, the clinician can provide input via user interface 84 indicating processor 80 should not select the electrode combination.

In some examples, the clinician can also provide user input selecting another electrode combination, e.g., by selecting another one or more electrodes 24, 26 of leads 20 or by interacting with the graphical display of the therapy field model to adjust the size, location or other field characteristic of the displayed therapy field. Processor 80 can then automatically select the electrode combination with which stimulation delivered by IMD 16 results in the adjusted therapy field. An example graphical user interface presented by programmer 14 with which the clinician can adjust the size, location or other field characteristic of the displayed therapy field to select another electrode combination is described below with respect to FIG. 18.

Processor 80 of programmer 14 receives a bioelectrical brain signal sensed by IMD via the selected electrode combination (128). In some examples, processor 80 initiates the sensing of the bioelectrical brains signal. For example, processor 80 of programmer 14 can transmit a message to IMD 16 via the respective telemetry modules 86, 50, where the message requests that processor 40 of IMD 16 control sensing module 46 to sense a bioelectrical brain signal via the selected electrode combination. Processor 40 can then transmit the bioelectrical brain signal (or data based on the signal) to processor 80 of programmer 14 via the respective telemetry modules 50, 86. In other examples, such as examples in which processor 40 of IMD 16 selects the electrode combination based on a physiological model, processor 40 of IMD 16 can automatically (e.g., independently of any control by programmer 14) control sensing module 46 to sense a bioelectrical brain signal via the selected electrode combination. Other techniques for controlling the sensing of the bioelectrical brain signal by IMD 16 via the selected electrode combination are contemplated.

In addition, in other examples, processor 40 of IMD 16 controls sensing module 46 to sense a plurality of bioelectrical brain signals with different combinations of electrodes 24, 26, and transmits all the sensed bioelectrical signals to programmer 14, which stores the signals in memory 82. Processor 80 of programmer 14 can retrieve the bioelectrical brain signal sensed via the selected electrode combination from memory 82.

Figure 10:
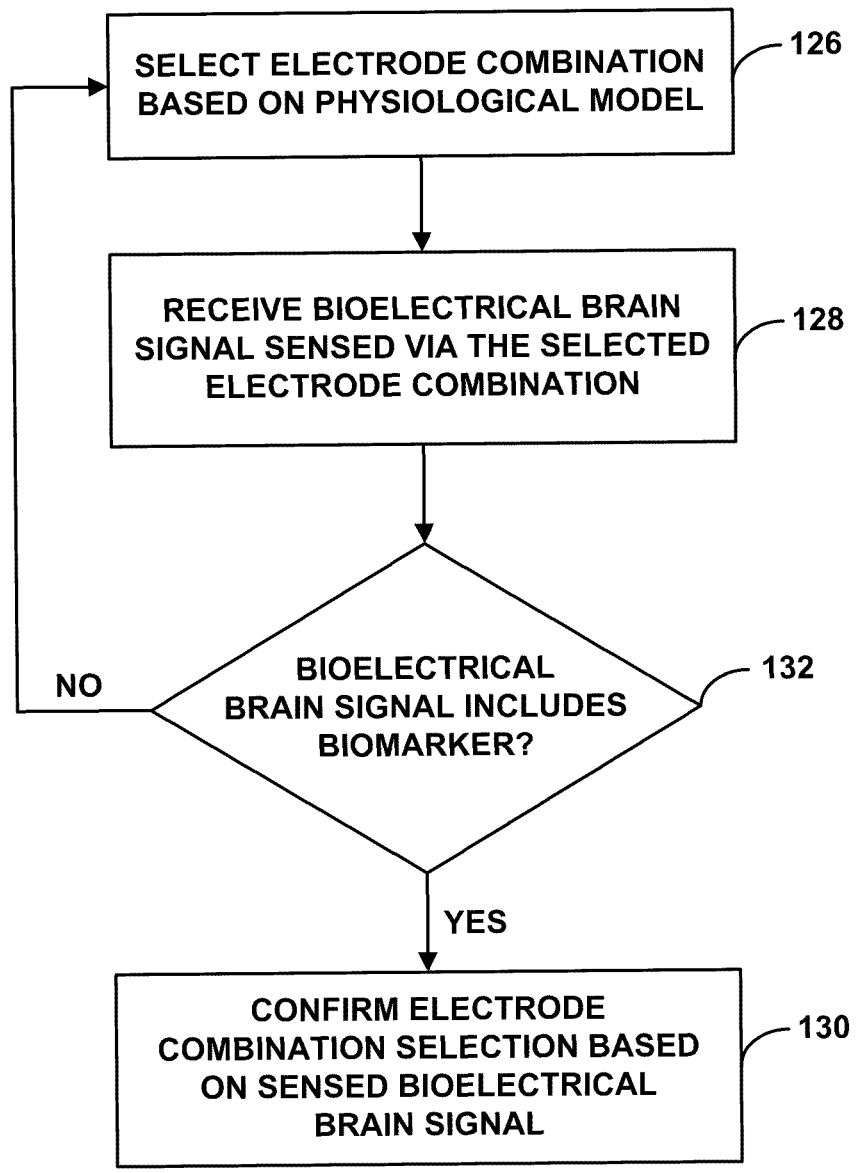

Processor 80 confirms the electrode combination selection based on the sensed bioelectrical brain signal (130). FIG. 10 is an example technique with which processor 80 can utilize a sensed bioelectrical brain signal to confirm an electrode combination selected based on the physiological model. After selecting an electrode combination based on a physiological model (126) and receiving a bioelectrical brain signal sensed via the sensed electrode combination (128), processor 80 determines whether the bioelectrical brain signal includes a biomarker indicative of the target tissue site (132). The biomarker can be, for example, a signal characteristic, such as the mean, median, peak or lowest amplitude of the section of the bioelectrical brain signal or a frequency domain characteristic of the sensed bioelectrical brain signal (e.g., the power level within a particular frequency band or a ratio of power levels within two frequency bands). Different regions of brain 28 may exhibit different potentials, such that bioelectrical brain signals sensed with electrodes in the different regions of brain 28 can result in bioelectrical brain signals having different signal characteristics. These different signal characteristics are biomarkers for the target tissue site. In this way, the signal characteristics of a bioelectrical brain signal can be used to determine whether the electrodes of the selected electrode combination are proximate the target tissue site or the tissue site associated with the stimulation-induced side effect. Memory 82 of programmer 14 or a memory of another device can store signal characteristics.

In some examples, processor 80 compares a characteristic of the sensed bioelectrical brain signal with a predetermined threshold value or template stored by memory 82 of programmer 14 or a memory of another device. The predetermined threshold value or template stored by memory 82 of programmer 14 can be selected by a clinician or processor 80 to represent a biomarker, e.g., characteristic of a signal that is sensed within the target tissue site within brain 28. Processor 80 confirms the electrode combination selection based on the sensed bioelectrical brain signal (130). For example, if processor 80 determines that the sensed bioelectrical brain signal exhibits the biomarker for the target tissue site (132), processor 80 confirm the electrode combination selection (134).

Processor 80 can then store the electrode combination in memory 82 as a useful stimulation electrode combination for therapy delivery by IMD 16 or transmit the selected electrode combination to IMD 16 for storage as part of a therapy program. On the other hand, if processor 80 determines that the sensed bioelectrical brain signal does not exhibit the biomarker for the target tissue site (132), processor 80 may not confirm the electrode combination selection. Instead, processor 80 can automatically select another electrode combination based on a physiological model or prompt the clinician to select another electrode combination (126).

In other examples of FIG. 10, a biomarker indicative of a tissue site associated with one or more stimulation-induced side effects can be used to confirm a selected electrode combination based on a sensed bioelectrical brain signal instead of or in addition to the biomarker indicative of the target tissue site. In these examples, processor 80 determines, based on the bioelectrical brain signal, whether the selected electrode combination is proximate one or more anatomical structures of brain 28 associated with a stimulation-induced side effect. This can be useful for, e.g., selecting an electrode combination that balances side effects experienced by patient 12 and the extent to which the symptoms of the patient's movement disorder (or other patient condition) are mitigated.

As discussed above, a bioelectrical brain signal sensed with a particular electrode combination can indicate whether the electrodes of the electrode combination are positioned within a particular tissue site of brain 28 (e.g., the target tissue site for therapy delivery or a tissue site associated with one or more stimulation-induced side effects). Thus, one or more characteristics of a bioelectrical brain signal can be useful for selecting a stimulation electrode combination. As an example, as discussed with respect to FIG. 8, a stimulation electrode combination can be selected based on a bioelectrical brain signal sensed via a sense electrode combination associated with the stimulation electrode combination. In addition, as discussed with respect to FIGS. 9 and 10, a selected electrode combination can be confirmed as a useful stimulation electrode combination based on a bioelectrical brain signal sensed via the selected electrode combination.

For a particular patient condition, one or more specific frequency bands may be more revealing of a useful target tissue site for providing stimulation therapy to patient 12 than other frequency bands. Processor 40 (shown in FIG. 2) of IMD 16, processor 80 (shown in FIG. 3) of programmer 14 or a processor of another device may perform a spectral analysis of the bioelectrical brain signal in the revealing frequency bands. The spectral analysis of a bioelectrical signal may indicate the power level of each bioelectrical signal within each given frequency band over a range of frequencies. While the beta frequency band is primarily referred to herein, in other examples, processor 40 or processor 80 may select a stimulation electrode combination based on the power level within one or more frequency bands other than the beta band.

For example, processor 40 or processor 80 may compare the power levels of a frequency band other than the beta band in bioelectrical signals sensed by different electrodes to determine relative values of the power levels for combinations of electrodes. Processor 40 or processor 80 may then determine which of the electrodes is closest to a target tissue site based on the relative values. In some examples, the beta band includes a frequency range of about 10 Hz to about 35 Hz, such as about 10 Hz to about 30 Hz or 13 Hz to about 30 Hz.

Different frequency bands are associated with different activity in brain 28. It is believed that some frequency band components of a bioelectrical brain signal from within brain 28 may be more revealing of particular patient condition and abnormal brain activity associated with the particular patient condition than other frequency components. One example of the frequency bands is shown in Table 1:

TABLE 1

| Frequency bands | |
|---|---|
| Frequency (f) Band Hertz (Hz) | Frequency Information |
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

The frequency ranges for the frequency bands shown in Table 1 are merely examples. The frequency ranges may differ in other examples. For example, another example of frequency ranges for frequency bands are shown in Table 2:

TABLE 2

| Frequency bands | |
|---|---|
| Frequency (f) Band Hertz (Hz) | Frequency Information |
| f < 5 Hz | δ (delta frequency band) |
| 5 Hz ≤ f ≤ 8 Hz | q (theta frequency band) |
| 8 Hz ≤ f ≤ 12 Hz | α (alpha frequency band) |
| 12 Hz ≤ f ≤ 16 Hz | s (sigma or low beta frequency band) |
| 16 Hz ≤ f ≤ 30 Hz | High β (high beta frequency band) |
| 50 Hz ≤ f ≤ 100 Hz | γ (gamma frequency band) |
| 100 Hz ≤ f ≤ 200 Hz | high γ (high gamma frequency band) |

In one example, a clinician may select the frequency band of a bioelectrical brain signal for selecting stimulation electrode combinations based on information specific to patient 12 or based on data gathered from more than one patient 12. The frequency bands that are useful for identifying a target tissue site for stimulation to manage a patient condition can be specific to a particular patient 12 or general to a group of patients with similar conditions. In some examples, a clinician may utilize medical imaging techniques to identify which portions of brain 28 exhibit abnormal activity when symptoms of the patient condition are observed. For example, the clinician may utilize an imaging device, such as magnetoencephalography (MEG), positron emission tomography (PET) or functional magnetic resonance imaging (fMRI) to identify the region of brain 28 associated that exhibits the greatest detectable change when certain patient symptoms (e.g., a difficulty initiating movement) are observed. In other examples, the clinician can select the target tissue site known to be associated with the patient condition based on, e.g., past knowledge or past studies on subjects with similar patient conditions. In the examples described below, the beta band is used as an example to describe the techniques for selecting stimulation electrode combinations based on a bioelectrical brain signal. However, the techniques described below are applicable to other frequency bands.

Some movement disorder symptoms of patient 12, such as bradykinesia, may be associated with abnormal synchronization of beta frequency band activity within particular structures of brain 28 of patient 12. Thus, in some patients, identifying the location within brain 28 that exhibits the highest relative beta band activity may indicate the location at which electrical stimulation may relatively effectively suppress the abnormal synchronization of beta frequency band activity associated with the patient's movement disorder. The location within brain 28 that demonstrates the highest relative beta band activity may indicate the location within brain 28 that is a suitable stimulation target for electrical stimulation to manage the patient's movement disorder.

As a result of directing stimulation to this stimulation target that exhibits a relatively high level of beta band energy, the intensity of stimulation that IMD 16 may deliver in order to provide efficacious stimulation therapy may be lower than the intensity of stimulation that may be required to provide efficacious stimulation therapy to other tissue sites that may be further from the stimulation target or less functionally related to the stimulation target. An intensity of stimulation may be related to the current or voltage amplitude of a stimulation signal, a frequency of the stimulation signal, and, if the signal comprises a pulse, a pulse width, and/or pulse shape of the stimulation signal.

In some examples, a group of sense electrodes that are closest to the tissue site with the highest relative beta band (or other selected frequency band) activity within brain 28 may provide the best relative efficacy for patient 12 when stimulation therapy is delivered via the electrodes of the group. A group of electrodes can include one electrode or more than one electrode (e.g., two, three, four, or more electrodes), and can include ring electrodes or a one or more segmented or partial ring electrodes. Thus, in some examples, a stimulation electrode combination is selected based on the electrodes with which IMD 16 sensed a bioelectrical brain signal having a relatively high beta band power. In some examples, electrical stimulation may be delivered to substantially the same location at which a bioelectrical brain signal having a relatively high relative beta band power was sensed in order to effectively suppress the abnormal synchronization of beta frequency band activity associated with the patient's movement disorder.

In other examples, the stimulation electrode combination may comprise a different subset of electrodes than the groups of sense electrodes that are closest to the tissue site with the highest relative beta band activity. For example, a sense electrode combination may include at least two electrodes 24, 26 of leads 20A, 20B, whereas a stimulation electrode combination may include a single electrode of leads 20A, 20B (e.g., to provide unipolar stimulation) or more than two electrodes. In a unipolar configuration, stimulation may be provided between an electrode of one of the leads 20A, 20B and a housing of IMD 16 or another reference electrode located farther away. In the case of stimulation electrode combinations, it may be possible for more than one electrode to share a polarity. Therefore, in some cases, the stimulation electrode combination selected based on a bioelectrical brain signal can include more electrodes than the sense electrode combination. If the stimulation electrode combination and an associated group of sense electrodes include at least one different electrode, the stimulation electrode combination and sense electrode combination may be positioned within different regions of brain 28. The regions may or may not overlap.

In some examples, the sense electrodes closest to the highest relative beta band activity within brain 28 may be mapped to a stimulation electrode combination that may provide relatively efficacious stimulation therapy. For example, the sense electrode combinations and the stimulation electrode combinations may be related by a functional relationship between different regions of brain 28. For example, a group of sense electrodes that senses a bioelectrical signal having a relatively high beta band power within a first part of the thalamus of brain 28 may be mapped to a second part of the thalamus that is functionally connected to first part. This functional relationship may indicate that if electrical stimulation is delivered to the second part of the thalamus via a particular stimulation electrode combination, any irregular oscillations or other irregular brain activity within the first part of the thalamus may be effectively suppressed.

One example method in which relative beta band power levels are recorded, analyzed, and compared to one another, and in which the sense electrode with the highest power level is selected as the sense electrode closest to the target tissue site is described in commonly assigned U.S. patent application Ser. No. 12/563,845 by Carlson et al., entitled "STIMULATION ELECTRODE SELECTION," which was filed on Sep. 21, 2009 and is incorporated herein by reference in its entirety. This technique may be useful for selecting stimulation electrode combinations based on the frequency domain characteristics of one or more bioelectrical brain signals sensed with respective sense electrode combinations. In some cases, however, when the bioelectrical brain signals are sensed with a bipolar sensing configuration (e.g., sensing between electrodes of leads 20A, 20B), the sense electrode combination with the highest recorded relative beta band power level may not be the closest to the target tissue site. For example, if the target tissue site (e.g., the site within brain 28 that exhibits the highest relative beta band power) is situated between two electrodes, the relative value for the electrode combination may have the lowest relative beta band power instead of the highest.

Techniques described in commonly assigned U.S. patent application Ser. No. 12/639,717 by Molnar et al., entitled, "STIMULATION ELECTRODE SELECTION" and filed on Dec. 19, 2009 and commonly assigned U.S. patent application Ser. No. 12/639,678 by Molnar et al., entitled, "STIMULATION ELECTRODE SELECTION" and filed on Dec. 19, 2009 may facilitate determining the sense electrode or electrodes closest to a target tissue site, including in cases in which the target tissue site is between two sense electrodes. By comparing the relative beta band power levels of bioelectrical brain signals sensed with different electrodes (or different combinations of electrodes), a processor of a device (e.g., IMD 16 or programmer 14) can determine whether the target tissue site is closer to certain electrodes because the strength of the relative beta band power level is revealing of the location of the target tissue site relative to the electrodes. The entire content of U.S. patent application Ser. Nos. 12/639,717 and 12/639,678 is hereby incorporated by reference.

Figure 11:
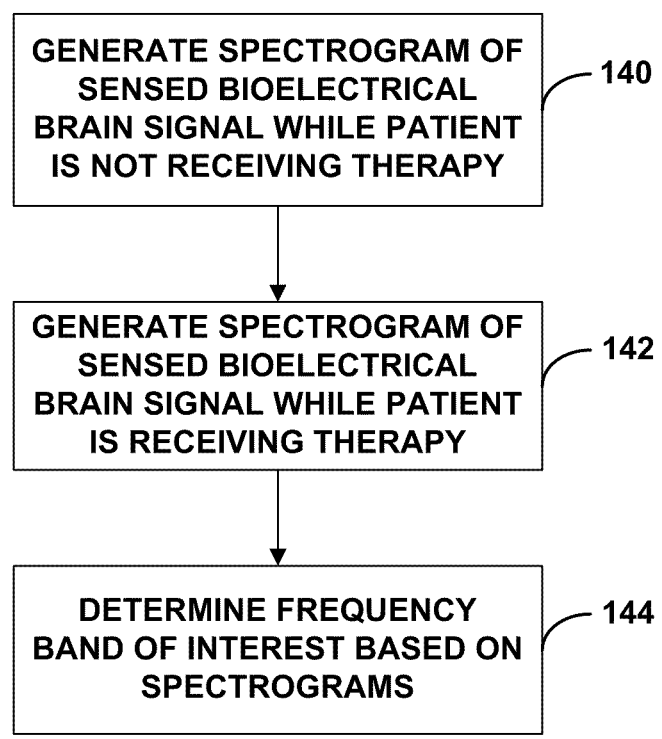
FIG. 11 is a flow diagram illustrating an example technique for determining a frequency band of interest for evaluating sense electrode combinations.

FIG. 11 is a flow diagram illustrating an example technique that processor 40 of IMD 16, processor 80 of programmer 14, or another computing device can implement to identify a frequency band of interest. The processor can utilize the frequency band of interest as a signal characteristic with which to compare bioelectrical brain signals and select a stimulation electrode combination, as described in further detail below. Processor 40 is referred to throughout the description of FIG. 11. In other examples, processor 80 of programmer 14 or another computing device may implement the technique shown in FIG. 11.

In the example shown in FIG. 11, processor 40 generates a spectrogram of a bioelectrical brain signal of patient 12 during a first time period in which patient 12 is in a pathological state, e.g., is not receiving any therapy to manage the movement disorder or other patient condition (140). Processor 40 generates a spectrogram during a second time period in which patient 12 is receiving therapy to manage the movement disorder or other patient condition (142). Processor 40 determines a frequency band of interest that indicates a biomarker for the patient's condition based on the spectrograms (144). In some examples, processor 40 may determine which frequency bands exhibited a relatively large and/or discernable change between the first and second time periods.

Therapy system 10 can select a sense electrode or electrode combination that is closest to a target tissue site based on a frequency band of interest in accordance with the techniques described herein, such as the techniques described with respect to FIGS. 12, 13, 15A-15C, 16, and 17. The selected sense electrode or electrode combination can then be used to select a stimulation electrode combination. In some examples, processor 40 may sense bioelectrical brain signals within brain 28 of patient 12 with each sense electrode combination of a plurality of stored sense electrode combinations.

Processor 80 of programmer 14 selects a stimulation electrode combination based on the sense electrode combination associated with one or more sensed bioelectrical brain signals having the greatest relative power level in the frequency band of interest. In other examples, processor 80 of programmer may select a stimulation electrode combination based on the sense electrode combination associated with a sensed bioelectrical brain signal having a lowest relative power level in the frequency band of interest. In some examples, the different sense electrode combinations and associated beta band power levels may be presented to a user, such as a clinician, via a display of a device, such as programmer 14.

FIGS. 12-15C, 16, and 17 are flow diagrams illustrating example techniques for selecting one or more sense electrode combinations that are closest to a target tissue site based on a bioelectrical brain signal. In some examples, after processor 40 of IMD 16 or processor 80 of programmer 14 selects the one or more sense electrodes that sensed the bioelectrical signal that is closest to the target tissue site using the techniques described with respect to FIGS. 12-15C, processor 40 or processor 80 may determine one or more stimulation electrodes based on the one or more sense electrodes. For example, processor 40 or 80 can determine one or more stimulation electrodes that are associated with the sense electrodes in the respective memories 42, 82. In another example, processor 40 or 80 selects the one or more sense electrodes as the stimulation electrodes. After determining the one or more stimulation electrodes based on the bioelectrical brain signal, processor 40 or 80 can confirm the selection of the one or more sense electrodes based on a physiological model, e.g., as described with respect to FIG. 8.

Other techniques can also be used to select a stimulation electrode combination based on a bioelectrical brain signal. For example, any of the techniques described in U.S. patent application Ser. Nos. 12/639,717 and 12/639,678 by Molnar et al. can be implemented by processor 40 of IMD 16, processor 80 of programmer 14 or a processor of another device in order to select a stimulation electrode combination for delivering efficacious therapy to patient 12 based on a bioelectrical brain signal. In addition, other types of biomarkers can be used to indicate whether a sense electrode combination includes electrodes that are positioned proximate to a target tissue site.

Figure 12:
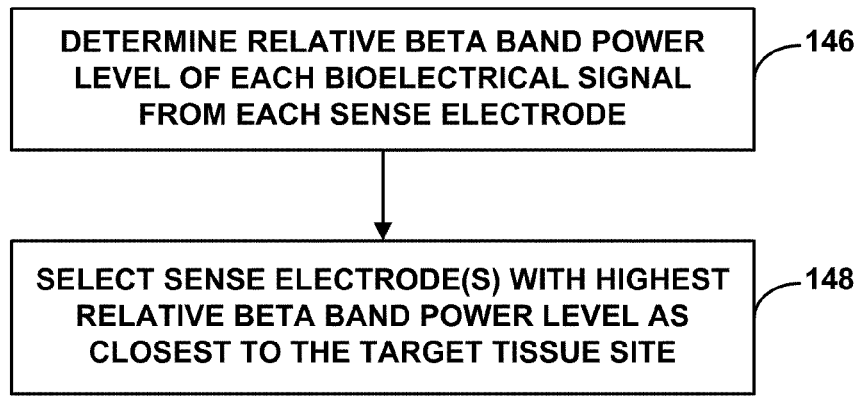
FIGS. 12 and 13 are flow diagrams illustrating example techniques for selecting sense electrode combinations that are closest to a target tissue site.
Figure 13:
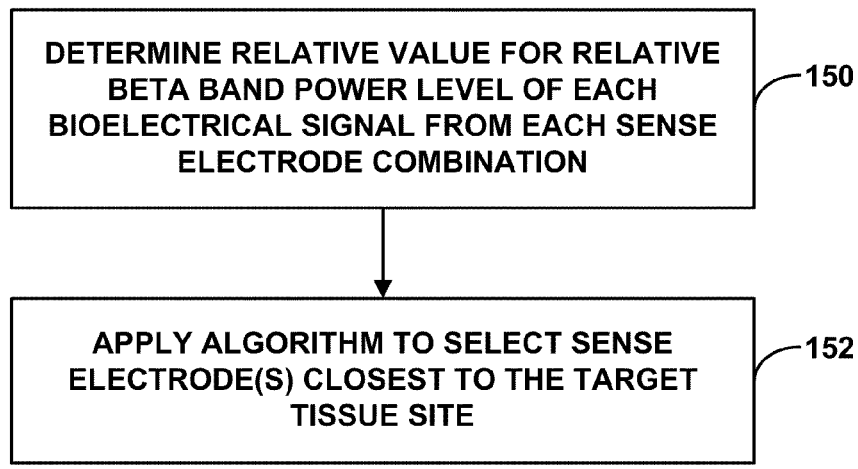

FIGS. 12 and 13 are flow diagrams illustrating example techniques for selecting sense electrode combinations that are closest to a target tissue site based on a bioelectrical brain signal. The target tissue site may be the tissue site within brain 28 of patient 12 that exhibits a bioelectrical signal with the highest relative power level in a particular frequency band or that exhibits another predetermined frequency domain characteristic (e.g., a lowest relative power level). As discussed above, with respect to movement disorders, a high relative beta band power level may be associated with abnormal oscillations or activity within brain 28. Selection of sense electrode combinations that are closest to the target tissue site may facilitate selection of stimulation electrode combinations that are most effective in providing stimulation therapy to patient 12.

Processor 40 controls sensing module 46 of IMD 16 to sense bioelectrical signals in the brain of patient 12 with a plurality of sense electrode combinations including one or more electrodes from electrodes 24, 26. In some examples, processor 40 controls sensing module 46 to sense bioelectrical signals with unipolar electrode configurations, in which sensing module 46 senses a bioelectrical signal between each of one or more individual electrodes 24, 26 and the housing of IMD 16 (e.g., a housing electrode coupled to or defined by an outer housing of IMD 16) or another reference. While sensing in a unipolar configuration may be useful for sensing bioelectrical brain signals, sensing between an electrode of one of the leads 20A, 20B and a housing of IMD 16 or another reference may introduce noise into the sensed brain signal and, in some cases, distort the sensed bioelectrical brain signal.

For example, unipolar sensing of bioelectrical signals in brain 28 of patient 12 may result in the sensing of a relatively high amount of electrical cardiac activity of patient 12 or other electrical activity of patient 12 or external to patient 12 compared to bipolar sensing between electrodes 24, 26 of leads 20. Therefore, in other examples, processor 40 controls sensing module 46 to sense bioelectrical signals with bipolar electrode configurations, in which sensing module 46 senses a bioelectrical signal between pairs of electrodes 24, 26, e.g., between electrodes 24A and 24B, between electrodes 24A and 24D, etc. Unipolar and bipolar sensing configurations may also be used with other electrode configurations, such as the configuration defined by electrodes 66, 68, 70, and 72 of lead 62 (FIGS. 4A and 4B).

FIG. 12 is a flow diagram illustrating a general technique for selecting a group of sense electrodes when using a unipolar sensing configuration. As an example, processor 40 can control sensing module 46 (FIG. 2) of IMD 16 to sense bioelectrical signals with each of electrodes 24 in a unipolar configuration. For example, processor 40 may control sensing module 46 to sense a first bioelectrical signal between electrode 24A and the housing of IMD 16 (e.g., an electrically conductive outer housing of IMD 16 or an electrode coupled to a conductive or nonconductive outer housing), a second bioelectrical signal between electrode 24B and the housing of IMD 16, a third bioelectrical signal between electrode 24C and the housing of IMD 16, and a fourth bioelectrical signal between electrode 24D and the housing of IMD 16.

Processor 40 determines the relative beta band power level for each bioelectrical brain signal from each sense electrode (146). For example, processor 40 may determine the relative beta band power level for each of the first, second, third, and fourth bioelectrical signals. Processor 40 selects the one or more sense electrodes that sensed the bioelectrical signal with the highest relative beta band power as the sense electrode closest to the target tissue site (148). In some examples, processor 40 selects a stimulation electrode combination or a therapy program based on selecting the sense electrodes closest to the target tissue site. In some examples, the stimulation electrode combination may comprise some or all of the sense electrodes closest to the target tissue site. In other examples, the stimulation electrode combination may comprise different electrodes than the sense electrodes closest to the target tissue site.

FIG. 13 is a flow diagram illustrating an example technique for selecting a group of sense electrodes based on relative values of relative power levels in a selected frequency band in order to simulate a bipolar sensing configuration. In an example of the technique shown in FIG. 13, processor 40 controls sensing module 46 of IMD 16 to sense bioelectrical signals with each of the electrodes 24 in a unipolar configuration. For example, processor 40 may control sensing module 46 to sense a first bioelectrical signal with electrode 24A and a reference (e.g., a housing electrode), a second bioelectrical signal with electrode 24B and a reference, a third bioelectrical signal with electrode 24C and a reference, and a fourth bioelectrical signal with electrode 24D and a reference.

After sensing the bioelectrical brain signals with electrodes 24, processor 40 determines the relative value of the relative beta band power level for each combination of the first, second, third, and fourth bioelectrical signals (150). For example, processor 40 determines a first relative value by determining the absolute difference in the relative beta band power levels of the first and second bioelectrical signals, a second relative value by determining the absolute difference in the relative beta band power levels of the first and third bioelectrical signals, a third relative value by determining the absolute difference in the relative beta band power levels of the first and fourth bioelectrical signals, a fourth relative value by determining the absolute difference in the relative beta band power levels of the second and third bioelectrical signals, a fifth relative value by determining the absolute difference in the relative beta band power levels of the second and fourth bioelectrical signals, and a sixth relative value by determining the absolute difference in the relative beta band power levels of the third and fourth bioelectrical signals.

Each of the determined relative values indicates the difference in relative beta band power levels for signals sensed by respective electrodes. Therefore, the relative value indicates the relative beta band power level of a bioelectrical signal that is sensed between the electrodes associated with the sensed bioelectrical brain signals, i.e., in a bipolar electrode configuration. For example, a relative value determined based on the first and second bioelectrical signals indicates (e.g., is substantially equal to) the relative beta band power level of a bioelectrical signal that is sensed between electrodes 24A, 24B. As a result, the technique for determining the relative values of the relative beta band power level of bioelectrical brain signals sensed via different electrodes can be used as a surrogate for bipolar sensing and determining a beta band power level of a bioelectrical signal sensed via the bipolar sensing configuration. In each example described herein that utilizes a relative value of the relative beta band power levels of bioelectrical brain signals sensed in a unipolar configuration, the relative beta band power level of a bioelectrical signal that is sensed between electrodes in a multipolar (e.g., bipolar) configuration can be substituted to arrive at the same stimulation electrode combination selection.

After determining the relative value of the relative beta band power level for each combination of the first, second, third, and fourth bioelectrical signals (150), processor 40 of IMD 16 or processor 80 of programmer 14 accesses the respective memory 42, 82 and executes an algorithm stored therein to determine and select the one or more sense electrodes closest to the target tissue site based on the relative values for the relative beta band power levels (152).

Figure 15A:
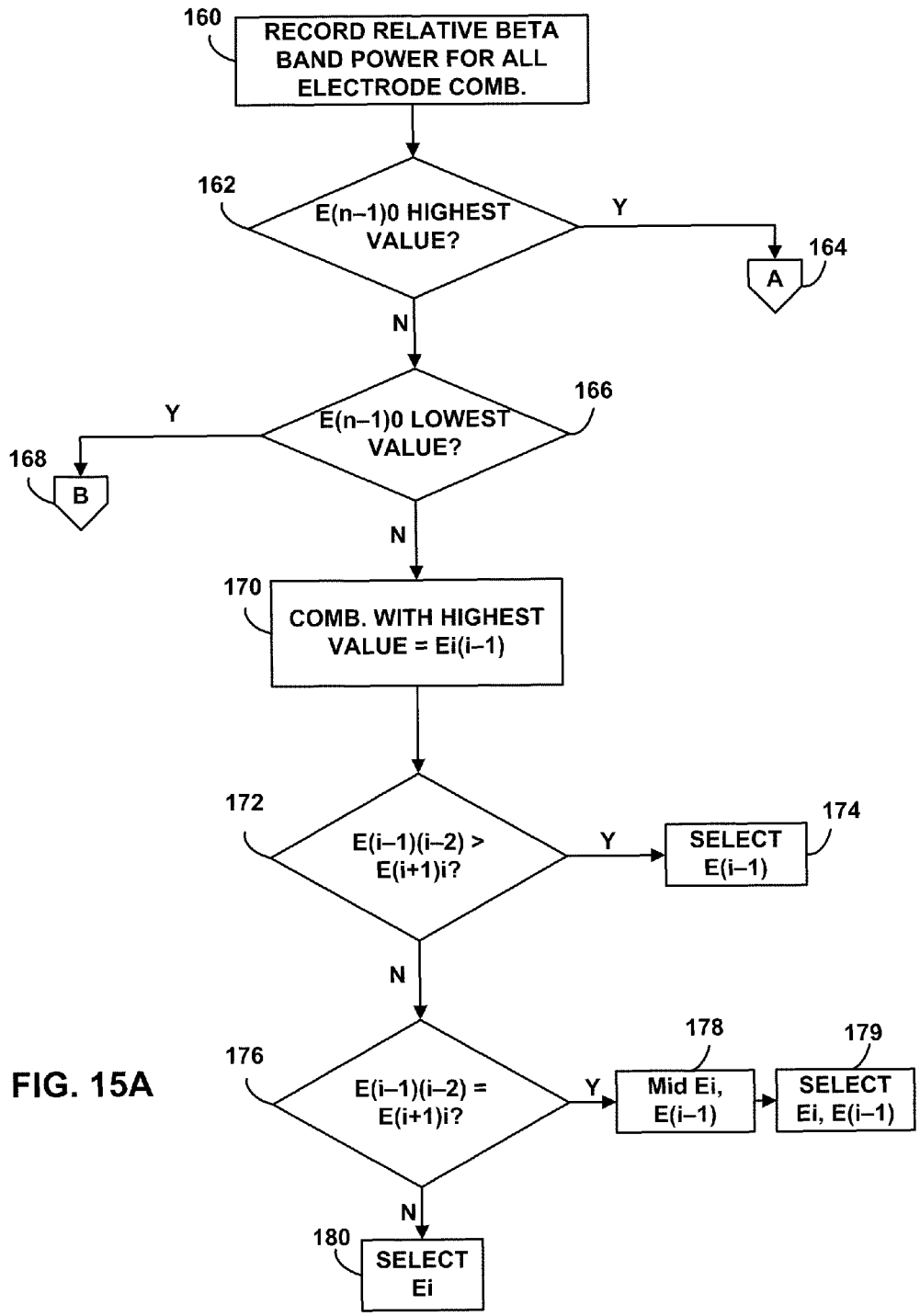
FIGS. 15A-15C are flow diagrams illustrating a general algorithm that can be implemented to select electrodes that are closest to a target tissue site.
Figure 15B:
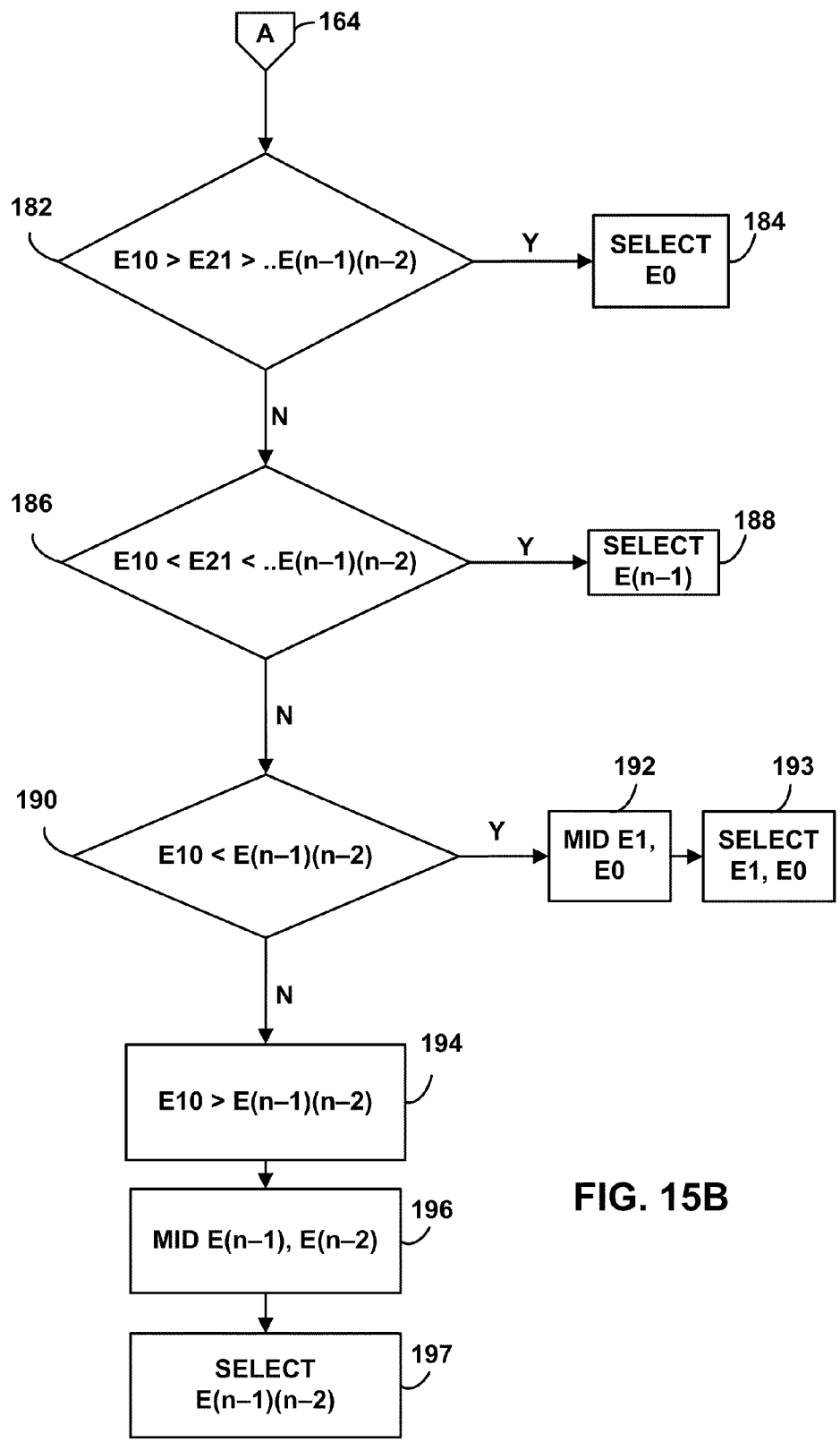
Figure 15C:
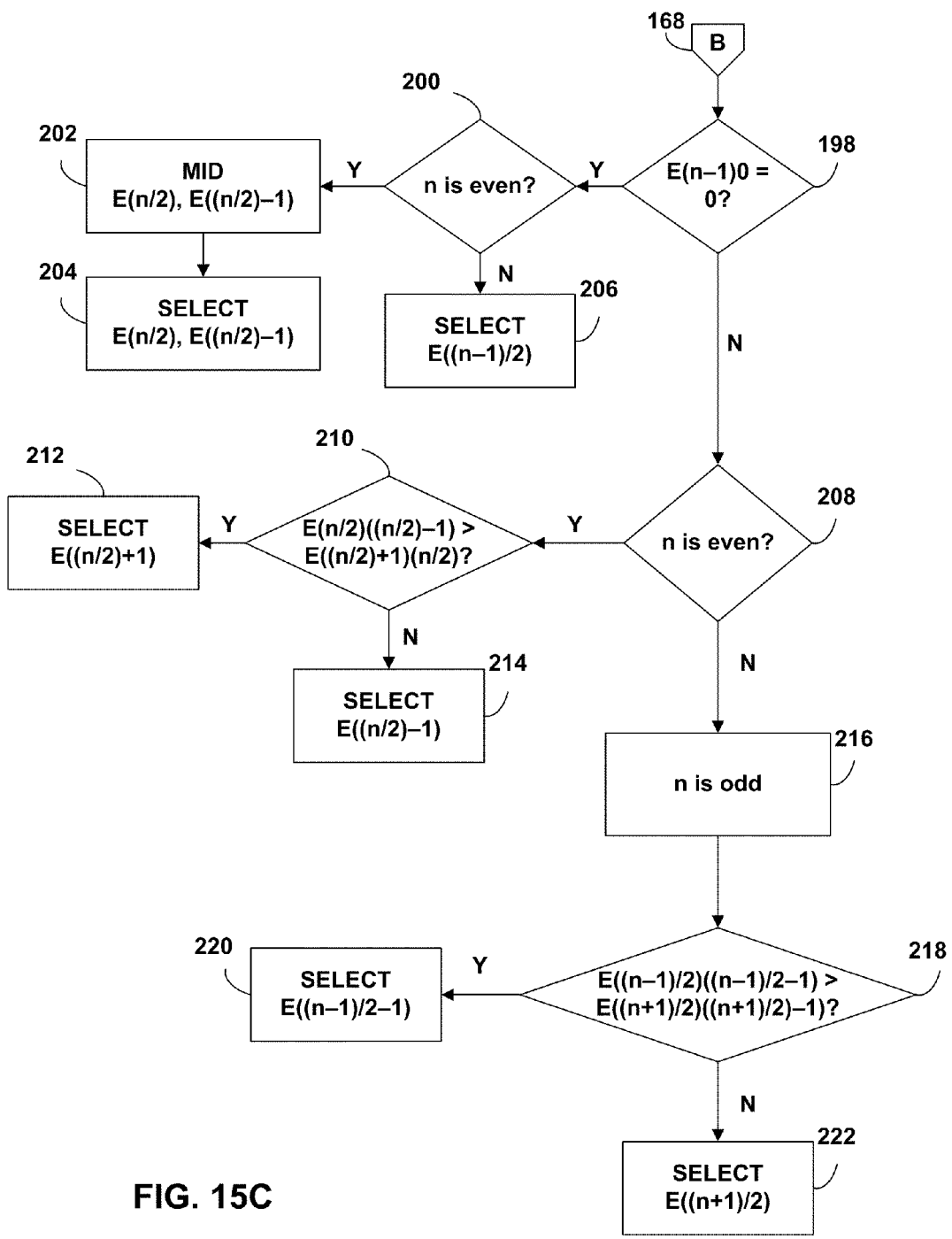

An example algorithm is described with respect to FIGS. 15A-15C. In some examples, processor 40 selects a stimulation electrode combination or a therapy program based on the pair of sense electrodes determined to be closest to the target tissue site. In some examples, the stimulation electrode combination may comprise some or all of the sense electrodes closest to the target tissue site. In other examples, the stimulation electrode combination may comprise different electrodes than the sense electrodes closest to the target tissue site.

Figure 14:
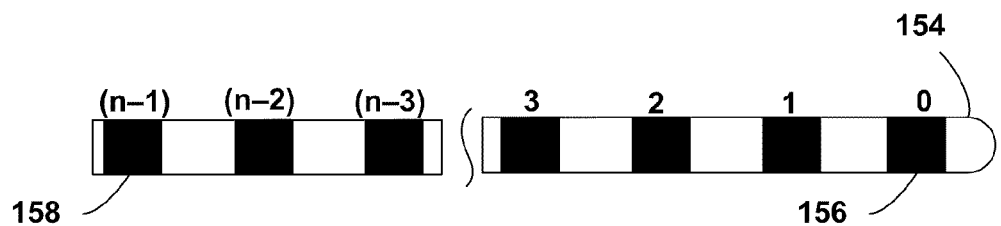
FIG. 14 is a diagram illustrating a medical lead with a plurality of electrodes.

The systems and techniques described herein for selecting one or more sense electrodes that are closest to a target tissue site based on a sensed bioelectrical brain signal may be applicable to medical leads with any number and configuration of electrodes. FIG. 14 illustrates an example lead 154 with a number n of electrodes between the most distal electrode 156 of lead 154, numbered 0, to the most proximal electrode 158 of lead 154, numbered n−1. With respect to the flow diagrams in FIGS. 15A-15C, combinations of sense electrodes will be identified using the electrode numbering system illustrated in FIG. 14 that includes electrodes numbered 0 through n−1. For example, the electrode combination of the most distal pair of electrodes on lead 154 will be referred to as E10, the electrode combination between the second most distal pair of electrodes on lead 154 will be referred to as E21, the electrode combination between the most distal and the most proximal electrodes on lead 154 will be referred to as E(n−1)0, and so forth.

FIGS. 15A-15C illustrate an example technique for selecting one or more sense electrodes of lead 154 (FIG. 14) that are closest to a target tissue site within brain 28. As previously described, the target tissue site can be, for example, the tissue site exhibiting a relatively high beta band energy or the tissue site within brain 28 that exhibits another predetermined frequency band characteristic. The target tissue site can be, for example, the tissue site at which therapy delivery (e.g., stimulation or drug delivery) provides efficacious therapy to patient 12 to mitigate symptoms of the patient condition. Processor 40 of IMD 16, processor 80 of programmer 14 or a processor of another device can implement the algorithm shown in FIGS. 15A-15C. For ease of description, FIGS. 15A-15C are described with respect to processor 80. However, the techniques shown in FIGS. 15A-15C can be carried out by a different processor, such as processor 40 of IMD 16.

The relative beta band power level may be a ratio of the power in a beta band of the sensed signal to the overall power of the sensed signal, and may be used instead of the beta band power in order to normalize the bioelectrical signals sensed by sense electrodes located in different regions of brain 28. The relative value of the relative beta band power level between two electrodes (i.e., the electrodes of an electrode combination) may be defined as the magnitude of the difference in amplitude between the relative beta band power levels sensed with each of the two electrodes in the electrode combination in a unipolar configuration. For example, the relative value of the relative beta band power levels for electrode combination 24A-24B may be defined as the magnitude of the difference in the amplitude of the relative beta band power level sensed by electrode 24A and a reference electrode and the amplitude of the relative beta band power level sensed by electrode 24B and a reference electrode.

In general, the technique shown in FIGS. 15A-15C comprises determining if the target tissue site is closest to either of the most distal or the most proximal electrodes, i.e., either of electrodes 0 or n−1 (shown in FIG. 14), by determining whether the relative value of the relative beta band power level between these two electrodes is the highest. If this relative value is the highest, the target tissue site is closest to either the most distal or the most proximal electrode. If this relative value is not the highest, the technique comprises determining if the target tissue site is closest to the electrodes in the middle of the lead by determining whether the relative value of the relative beta band power level between the most distal and the most proximal electrodes is the lowest. If this relative value is the lowest, the target tissue site is closest to the middle electrode or electrodes. If this value is neither the highest nor the lowest, the technique comprises determining which pair of adjacent electrodes sensed the highest relative value of the relative beta band power level and determining that the target tissue site is closest to one of this pair of adjacent electrodes.

As shown in FIG. 15A, processor 800 determines the relative beta band power level for each bioelectrical signal sensed by each adjacent electrode combination, i.e., E10, E21, E32, etc. and for the electrode combination comprising the most proximal and the most distal electrodes, i.e., E(n−1)0 (160). Next, processor 80 determines whether electrode combination E(n−1)0 has the highest relative value (162). If processor 80 determines that electrode combination E(n−1)0 has the highest relative value, processor 80 executes a portion of the sense electrode selection algorithm referred to as "part A" for ease of description (164), which will be described with respect to FIG. 15B.

If, on the other hand, processor 80 determines that electrode combination E(n−1)0 does not have the highest relative value, processor 80 determines whether electrode combination E(n−1)0 instead has the lowest relative value (166). If processor 80 determines that electrode combination E(n−1)0 has the lowest relative value, processor 80 executes the portion of the sense electrode selection algorithm referred to as "part B" for ease of description, which will be described with respect to FIG. 15C (168).

If processor 80 determines that electrode combination E(n−1)0 has neither the highest nor the lowest relative value, processor 80 determines which electrode combination has the highest relative value. The electrode combination with the highest relative value is referred to as electrode combination Ei(i−1) (170). Next, processor 80 determines whether the electrode combination proximal to the electrode combination with the highest relative value, i.e., electrode combination E(i−1)(i−2), has a higher relative value than the electrode combination distal to the electrode combination with the highest relative value, i.e., electrode combination E(i+1)i (172).

If processor 80 determines that electrode combination E(i−1)(i−2) has a higher relative value than electrode combination E(i+1)i, processor 80 selects the proximal electrode, i.e., E(i−1), of the electrode combination with the highest relative value as the electrode closest to the target tissue site (174). Processor 80 may select a stimulation electrode combination based on determining that E(i−1) is the electrode closest to the target tissue site. In some examples, processor 80 selects a stimulation electrode combination including electrode E(i−1) based on determining that E(i−1) is the electrode closest to the target tissue site.

If, on the other hand, processor 80 determines that electrode combination E(i−1)(i−2) does not have a higher relative value than electrode combination E(i+1)i, processor 80 determines whether electrode combination E(i−1)(i−2) has a relative value substantially equal to the relative value of electrode combination E(i+1)i (176). If processor 80 determines that electrode combination E(i−1)(i−2) has a relative value equal to the relative value of electrode combination E(i+1)i, processor 80 determines that the target tissue site is located closest to the midpoint of electrodes Ei and E(i−1) (128) and selects electrodes Ei and E(i−1) as the electrodes closest to the target tissue site (179). Processor 80 may select a stimulation electrode combination based on determining that Ei and E(i−1) are the electrodes closest to the target tissue site. In some examples, processor 80 selects a stimulation electrode combination including electrodes Ei and E(i−1) based on determining that Ei and E(i−1) are the electrodes closest to the target tissue site.

If processor 80 determines that electrode combination E(i−1)(i−2) does not have a relative value equal to the relative value of electrode combination E(i+1)i, processor 80 selects the distal electrode, i.e., electrode Ei, of the electrode combination with the highest relative value as the electrode closest to the target tissue (180).

FIG. 15B, as mentioned above, illustrates part A of the sense electrode selection algorithm, which processor 80 implements upon determining that electrode combination E(n−1)0 has the highest relative value (164). Processor 80 determines whether the most distal pair of adjacent electrodes, i.e., electrode combination E10, has a higher relative value than the second most distal pair of adjacent electrodes, i.e., electrode combination E21, and whether electrode combination E21 has a higher relative value than the third most distal pair of adjacent electrodes, i.e., electrode combination E32, and whether electrode combination E32 has a higher relative value than the fourth most distal pair of adjacent electrodes, i.e., electrode combination E43, and so on until processor 80 determines whether electrode combination E(n−2)(n−3) has a higher relative value than electrode combination E(n−1)(n−2) (182). If processor 80 determines that electrode combination E10 has a higher relative value than electrode combination E21 and that electrode combination E21 has a higher relative value than electrode combination E32 and that electrode combination E32 has a higher relative value than electrode combination E43 and so on until processor 80 determines that electrode combination E(n−2)(n−3) has a higher relative value than electrode combination E(n−1)(n−2), processor 80 selects the most distal electrode E0 as the electrode closest to the target tissue site (184).

If, on the other hand, processor 80 determines that these criteria are not met, processor 80 determines whether the most distal pair of adjacent electrodes, i.e., electrode combination E10, has a lower relative value than the second most distal pair of adjacent electrodes, i.e., electrode combination E21, and whether electrode combination E21 has a lower relative value than the third most distal pair of adjacent electrodes, i.e., electrode combination E32, and whether electrode combination E32 has a lower relative value than the fourth most distal pair of adjacent electrodes, i.e., electrode combination E43, and so on until processor 80 determines whether electrode combination E(n−2)(n−3) has a lower relative value than electrode combination E(n−1)(n−2) (186). If processor 80 determines that electrode combination E10 has a lower relative value than electrode combination E21 and that electrode combination E21 has a lower relative value than electrode combination E32 and that electrode combination E43 has a lower relative value than electrode combination E32 and so on until processor 80 determines that electrode combination E(n−2)(n−3) has a lower relative value than electrode combination E(n−1)(n−2), processor 80 selects the most proximal electrode E(n−1) as the electrode closest to the target tissue site (188).

If processor 80 determines that these criteria are not met, processor 80 determines whether the most distal pair of electrodes E10 has a lower relative value than the most proximal pair of electrodes E(n−1)(n−2) (190). If processor 80 determines that electrode combination E10 has a lower relative value than electrode combination E(n−1)(n−2), processor 80 determines that the target tissue site is closest to the midpoint of the most distal electrode pair E10 (192) and selects electrodes E1 and E0 as the electrodes closest to the target tissue site (193). If processor 80 determines that electrode combination E10 does not have a lower relative value than electrode combination E(n−1)(n−2), processor 80 determines that electrode combination E10 has a higher relative value that electrode combination E(n−1) (n−2) (194) and determines that the target tissue site is closest to the midpoint of the most proximal electrode pair E(n−1)(n−2) (196). Processor 80 then selects electrodes E(n−1) and E(n−2) as being closest to the target tissue site (197).

FIG. 15B, as mentioned above, illustrates part B the sense electrode selection algorithm, which processor 80 executes upon determines that electrode combination E(n−1)0 has the lowest relative value (168) (FIG. 15A). Processor 80 determines whether electrode combination E(n−1)0 has a relative value equal to zero (198). If processor 80 determines that electrode combination E(n−1)0 has a relative value equal to zero, processor 80 determines whether the number of electrodes n is even (200). If the number of electrodes n is even, processor 80 determines that the target tissue site is located closest to the midpoint between the middle two electrodes E(n/2) and E((n/2)−1) (202). Processor 80 then selects E(n/2) and E((n/2)−1) as the electrodes closest to the target tissue site (204). If processor 80 determines that the number of electrodes n is not even (200), processor 80 determines that the middle electrode E((n−1)/2) is the electrode closest to the target tissue site (206).

If processor 80 determines that electrode combination E(n−1)0 does not have a relative value equal to 0 (198), processor 80 determines whether the number of electrodes n of the lead is even (208). If processor 80 determines that the number of electrodes n is even, processor 80 determines whether the middle electrode combination E(n/2)((n/2)−1) has a higher relative value than the electrode combination comprising the proximal electrode of the middle electrode pair and the electrode proximal to the proximal electrode of the middle electrode pair, electrode combination E((n/2)+1)(n/2) (210). If processor 80 determines that electrode combination E(n/2)((n/2)−1) has a higher relative value than electrode combination E((n/2)+1)(n/2), processor 80 determines that the electrode proximal to the proximal electrode of the middle electrode pair E((n/2)+1) is the electrode closest to the target tissue site (212). If processor 80 determines that electrode combination E(n/2)((n/2)−1) does not have a higher relative value than electrode combination E((n/2)+1)(n/2), processor 80 determines that the distal middle electrode E((n/2)−1) is the electrode closest to the target tissue site (214).

If processor 80 determines that the number of electrodes n is not even (208), processor 80 determines that the number of electrodes n of the lead is odd (216). Processor 80 then determines if the electrode combination comprising the middle electrode and the electrode adjacent and distal to the middle electrode, electrode combination E((n−1)/2)((n−1)/2−1), has a higher relative value than the electrode combination comprising the middle electrode and the electrode adjacent and proximal to the middle electrode, electrode combination E((n+1)/2)((n+1)/2)−1) (218). If processor 80 determines that electrode combination E((n−1)/2)((n−1)/2−1) has a value higher than E((n+1)/2)((n+1)/2)−1), processor 80 selects the middle electrode E((n−1)/2−1) as the electrode closest to the target tissue site (220). If processor 80 determines that electrode combination E((n−1)/2)((n−1)/2−1) does not have a higher relative value than electrode combination E((n+1)/2)((n+1)/2)−1), processor 80 selects the electrode adjacent and proximal to the middle electrode E((n+1)/2) as the electrode closest to the target tissue (242).

Figure 16:
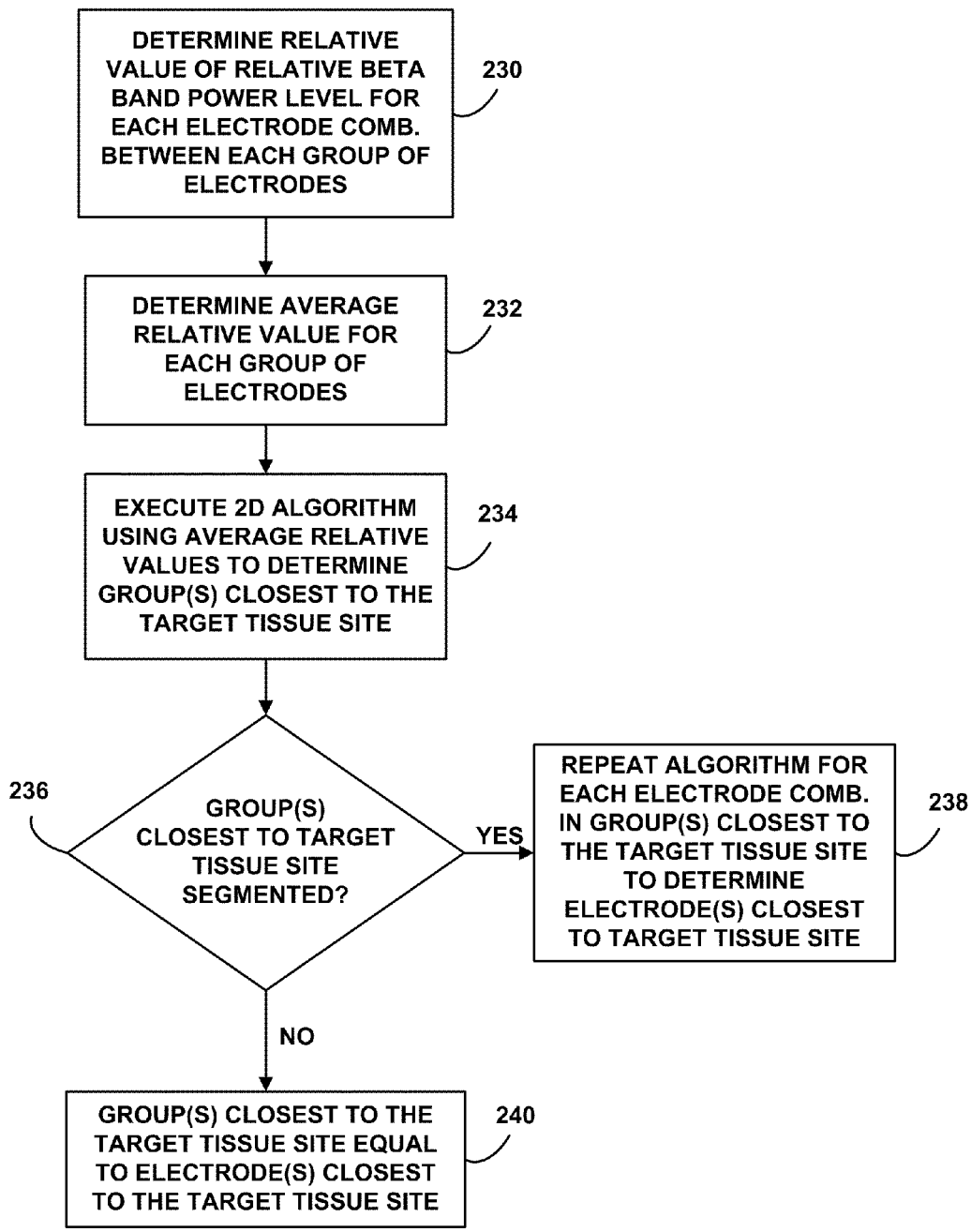
FIG. 16 is a flow diagram illustrating an example technique for determining the electrode or electrodes closest to a target tissue site for a lead comprising one or more groups of segmented electrodes.

In examples in which one or both leads 20 of therapy system 10 include segmented electrodes, processor 80 of programmer 14 (or a processor of another device) can implement an algorithm that specifies which one or more electrodes of a plurality of electrodes that shares a position along a longitudinal axis of the lead, but face in different directions are closest to a target tissue site. FIG. 16 is a flow diagram illustrating an example technique for determining which electrode or electrodes are closest to a target tissue site for a lead comprising groups of segmented electrodes, such as lead 62 (FIGS. 3A and 3B). In this example, the technique is described with respect to lead 62 which comprises groups of electrodes 64 including groups of segmented electrodes 68 and 70. In other examples, however, the technique may be applicable to a lead with any combination and configuration of groups of ring electrodes and segmented electrodes. As with FIGS. 15A-15C, processor 80 can execute an algorithm stored by memory 82 that causes processor 80 to carry out each of the steps of the technique illustrated in FIG. 16. However, in other examples, the technique may be carried out by a different processor, such as processor 40 of IMD 16.

In general, FIG. 16 illustrates a technique that may provide a more robust indication of the location of the target tissue site within brain 28 than the techniques illustrated in FIGS. 15A-15C. For example, in addition to determining the position of the target tissue site along the longitudinal axis of a lead, the technique illustrated in FIG. 16 includes determining the location of a target tissue site relative to a side of lead 62 (e.g., as indicated by a direction nonparallel to a longitudinal axis of lead 62, such as a direction substantially perpendicular to the longitudinal axis). Determining the position of the target tissue site in a first direction, as indicated by the longitudinal axis of the lead, and subsequently in a second direction, as indicated by a direction in which the segmented electrodes are displaced from one another, may provide additional information about the target tissue site location, facilitating selection of a stimulation electrode combination that provides more efficacious therapy to patient 12.

Processor 80 determines the relative values of the relative beta band power level for each electrode combination between each group of electrodes (230). Specifically, processor 80 determines the relative values for each of electrode combinations 72-70A, 72-70B, 72-70C, 70A-68A, 70B-68B, 70C-68C, 68A-66, 68B-66, 68C-66, and 72-66. Processor 80 then determines an average relative value for each group of electrodes (232). In order to determine the average value for group of electrode combinations including electrodes 72-70, i.e., comprised of the most distal group electrodes, processor 80 determines the average of the relative values for electrode combinations 72-70A, 72-70B, and 72-70C. In order to determine the average relative value for group of electrode combinations 70-68, i.e., the middle groups of electrodes, processor 80 determines the average of the relative values for electrode combinations 70A-68A, 70B-68B, and 70C-68C. In order to determine the average relative value for group of electrode combinations 68-66, i.e., the most proximal groups of electrodes, processor 80 determines the average of the relative values for electrode combinations 68A-66, 68B-66, and 68C-66. Processor 80 may not determine an average relative value for electrode combination 72-66, i.e., the most proximal and most distal groups of electrodes, because groups of electrodes 72 and 66 each comprise only one ring electrode.

Next, processor 80 determines the group or groups (i.e., 66,68,70, and 72) of electrodes closest to the target tissue site (234). The process is similar to that shown in FIG. 8, except that processor 80 compares the average relative values for combinations of groups of electrodes 72-70,70-68, and 68-66 and the relative value for combination 72-66 instead of the relative values for each electrode combination. Once processor 80 has selected the group or groups of electrodes closest to the target tissue site, processor 80 determines whether the selected group or groups comprise a segmented array of electrodes, i.e., groups 68 or 70 (236). If processor 80 determines that the selected group or groups determined be closest to the target tissue site comprises a segmented array of electrodes, processor 80 repeats the algorithm described above with respect to determining which group of electrodes is closest to the target tissue site to determine which one or more segmented electrode in the selected group or groups of electrodes are closest to the target tissue site (238).

For example, if processor 80 determines that group of electrodes 68 is closest to the target tissue site, processor 80 determines the relative values for the relative beta band power levels of the electrode combinations 68A-68B, 68B-68C, and 68C-68A of the group. Processor 80 then determines which of electrodes 68A, 68B, and 68C are closest to the target tissue site based on the relative values. The determination of which of the electrodes 68A, 68B, and 68C of the group of segmented electrodes sharing a position along a longitudinal axis of the lead is closest to the target tissue site determines the location of the target tissue site in a different direction relative to the first determination for determining which group of electrodes is closest to the target tissue site.

For example, determining which group of electrodes is closest to the target tissue site includes determining which position along the longitudinal axis of lead 62 is closest to the target tissue site. Determining which of electrodes 68A, 68B, and 68C is closest to the target tissue site may include determining which position around the perimeter of lead 62 at the longitudinal position of electrodes 68 is closest to the target tissue site. Determining the position of the target tissue site in two directions, e.g., the longitudinal position and the position around the perimeter, may provide a more robust indication of the position of the target tissue site along lead 62 than determining the position of the target tissue site in only one direction.

If, on the other hand, processor 80 determines that the selected group or groups of electrodes do not comprise segmented electrodes, processor 80 determines that the electrode closest to the target tissue site is the group or groups closest to the target tissue site (240). For example, if processor 80 selects group of electrodes 72 as closest to the target tissue site, processor 80 consequently selects electrode 72 as the electrode closest to the target tissue site because group of electrodes 72 comprises only electrode 72.

The techniques for selecting an electrode that is closest to a target tissue site based on a bioelectrical brain signal described herein, such as the techniques described with respect to FIGS. 12, 13, 15A-15C, and 16, have been described with respect to sensing bioelectrical signals with electrode combinations in a unipolar configuration and then converting the unipolar bioelectrical signal data into bipolar bioelectrical signal data via the relative values. For example, processor 40 of IMD 16 can control sensing module 46 to sense a first bioelectrical signal with electrode 24A (FIG. 2) and a reference (e.g., a housing electrode), a second bioelectrical signal with electrode 24B and a reference, a third bioelectrical signal with electrode 24C and a reference, and a fourth bioelectrical signal with electrode 24D and a reference. Then, processor 80 of programmer 14 can determine relative values indicating the difference in relative beta band power levels for bioelectrical signals sensed by each electrode combination, i.e., electrode combinations 24A-24B, 24B-24C, 24C-24D, and 24A-24D.

Figure 17:
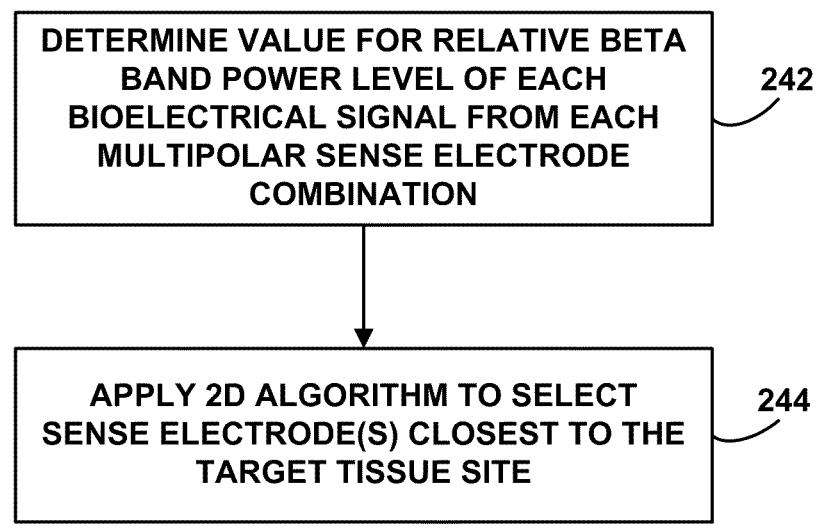
FIG. 17 is a flow diagram illustrating an example technique for determining the electrode or electrodes closest to a target tissue site for an IMD comprising multiple leads that each comprises groups of electrodes.

As shown in FIG. 17, in other examples, rather than determining the relative value of the relative beta band power level for each combination of the first, second, third, and fourth bioelectrical signals, processor 40 can control sensing module 46 to sense bioelectrical brain signals in a bipolar configuration (e.g., with combinations of electrodes 24) and processor 40 of IMD 16 or processor 80 of programmer 14 can determine the value of the relative beta band power level of the bioelectrical brain signal sensed via each bipolar electrode configuration (242). The relative beta band power level of the bioelectrical brain signal sensed via the bipolar electrode configuration is substantially equal to the relative value of the relative beta band power level of a bioelectrical brain signal sensed via the two electrodes of the bipolar configuration in a unipolar configuration. Processor 40 or processor 80 can select the one or more sense electrodes closest to the target tissue site based on the value of the relative beta band power levels of the bioelectrical brain signals sensed via respective bipolar electrode configurations (244).

As described in further detail in U.S. patent application Ser. Nos. 12/639,717 and 12/639,678 by Molnar et al., in some examples, processor 80 of programmer 14 can automatically rank the electrodes 24, 26 based on the proximity to the target tissue site. For example, in examples in which the relative beta band power level indicates proximity to the target tissue site, processor 80 of programmer 14 can rank electrodes 24, 26 based on the relative beta band power levels of bioelectrical brain signals sensed via electrodes 24, 26 in a unipolar configuration.

In some examples, providing a rank of each stimulation electrode may facilitate patient-specific electrical stimulation therapy delivery. For example, in some examples, delivery of electrical stimulation via the highest-ranked electrode combination may cause undesirable side effects. A clinician or user may access the rank of electrodes in order to choose a different electrode combination that may cause fewer side effects but may still be located relatively close to the target tissue site. In other examples, processor 40 of IMD 16 may access the rank of electrodes in order to automatically modify the stimulation electrode combination based on feedback from the patient regarding effects of a particular stimulation electrode combination.

Figure 18:
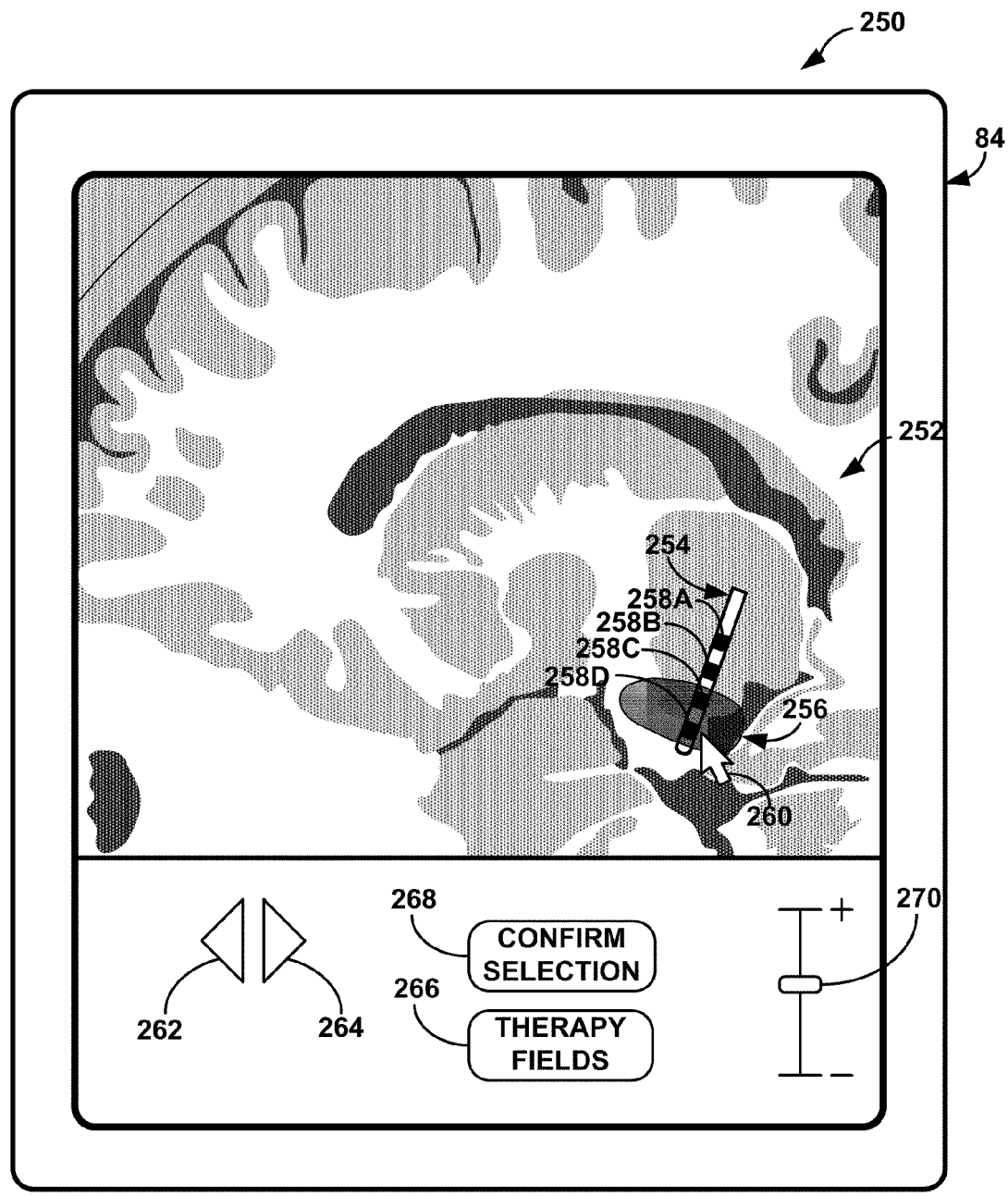
FIG. 18 is a screen diagram illustrating an example graphical user interface displayed by a programmer, where the graphical user interface presents a physiological model to a user.

As discussed above, a physiological model indicates tissue proximate implanted leads 20. Programmer 14 can generate and display a physiological model that helps a clinician visualize lead location, one or more anatomical structures, and/or therapy fields (e.g., volume of tissue activated). FIG. 18 is a screen diagram of an example graphical user interface (GUI) 230 displayed by user interface 84 of programmer 14, where the graphical user interface presents a physiological model to a user. The physiological model shown in FIG. 18 includes a graphical representation of one or more anatomical structures 252 of brain 28 of patient 12, lead icon 254 that provides a graphical representation of a lead implanted in patient 12, and therapy field model 256. Lead icon 254 includes electrodes 258A-258D.

GUI 250 can be presented on a display of user interface 84 of programmer. A user may interact with GUI 250 via one or more user input mechanisms of user interface 84 of programmer 14 in order to, for example, select electrodes 258A-258D as stimulation electrodes. In GUI 250, a lead icon 254 representing one of leads 20A, 20B is displayed to illustrate where the lead 20A or 20B is actually implanted relative to one or more anatomical regions of brain 28 of patient 12. In other examples, GUI 250 can display more than one lead and its respective electrodes. In the example shown in FIG. 18, GUI 250 displays a coronal view of brain 28, which is a front-back vertical section of brain 28. Anatomical structures 252 of brain 28 included in GUI 250 may be an actual image of brain 28 produced with MRI, CT, or another imaging modality. In one example, processor 80 of programmer 14 can generate the graphical representation of anatomical structures 252 based on multiple images of brain 28. In other examples, anatomical structures 252 of brain 28 can include a patient non-specific reference anatomical image, or a non-image based anatomical atlas (e.g., a drawing or computer rendering). These representations of brain 28, whether image based or not, are used to produce the graphical representations of anatomical regions of brain 28 needed to help the clinician visualize the location of electrodes of lead 20A or 20B in brain 28.

In examples in which lead icon 254 is displayed, lead icon 254 can be an image of the actual lead implanted within patient 12 or lead icon 254 can be an image of a type of lead implanted in patient 12, but not the specific lead implanted in patient 12. In other examples, lead icon 254 can be a drawing or computer rendering of the lead implanted within patient 12. The lead icon 254 displayed in GUI 250, however, represents the proper size of the lead implanted within patient 12. For example, electrodes 258A-258D shown in GUI 250 are positioned along lead 260 in the same relative spacing as the electrodes of the lead implanted within patient 12. In addition, processor 80 of programmer 14 generates GUI 250 such that lead icon 254 and anatomical structures 252 are displayed in proper scale, e.g., a substantially similar scale as the implanted lead and brain 28 of patient 12.

In examples in which anatomical structures 252 includes an actual image of brain 28 of patient 12, processor 80 can position lead icon 254 relative to anatomical structures 252 based on patient-specific information. For example, processor 80 may access a pre-operative MRI of brain 28 (e.g., before leads 20 are implanted), and morph brain structure volumes to the patient MRI in order to generate a 3D representation of brain 28, which can be useful for generating graphical representations of different "slices" of brain 28. Processor 80 can then access a post-operative MRI of brain 28 in order to determine the location of leads 20. Processor 80 can merge the pre-operative and post-operative MRI images, and locate the image of the lead relative to brain structure volumes in order to determine where to position lead icon 254 relative to anatomical structures 252.

The view of anatomical structures 252 of brain 28 shown in FIG. 18 is a 2D, cross-sectional (e.g., a coronal slice) of brain 28. Differently shaded portions of anatomical structures 252 indicate varying densities of tissue within brain 28. Darker portions indicate less dense tissue. For example, the darkest portion of anatomical structures 252 is indicative of spaces within brain 28 that contain cerebral spinal fluid (CSF). White portions of brain 28 indicate dense tissue and more neurons. The clinician may be able to recognize target anatomical regions based on the tissue densities of tissue shown by GUI 250. However, in some examples, processor 80 can help improve the clinician's understanding of the displayed anatomical structures 252, such as by labeling or color-coding one or more displayed anatomical structures 252 (e.g., by comparing the structures to an atlas that is pre-labeled).

The coronal view of anatomical structures 252 shown in FIG. 18 is merely an example image, and actual images may include a wider range of shades and higher image resolution. The view shown in FIG. 18 provides one perspective of lead 20A or 20B and the anatomical region in which the lead is implanted. In the example of GUI 250 shown in FIG. 18, the clinician may use arrows 262 and 264 to move to another coronal depth where the lead is implanted in brain 28 in order to view another perspective of the implanted lead.

In other examples of physiological models, other types of views of brain 28 and one or more implanted leads can be displayed by programmer 14 as a physiological model. Other views of brain 28 include other 2D views (e.g., a sagittal view), a 3D view, or any combination of 2D and 3D views. Similarly, lead icon 254 can be displayed as a 3D object, e.g., when a 3D view of anatomical structures 252 is displayed by GUI 250. Processor 80 of programmer 14 can automatically position lead icon 254 within GUI 250 based upon stereotactic data that is generated before lead 20A or 20B is implanted within patient 12. A stereotactic frame may be placed on a cranium of patient 12 to specifically locate areas of brain 128. In addition, this stereotactic information may be used to provide coordinates of the exact location of the implanted lead 20A, 20B. In some cases, processor 80 may automatically place lead icon 254 correctly within the anatomical region displayed by GUI 250 without any input from the user.

A clinician can utilize the graphical display of a physiological model shown in FIG. 18 to select one or more stimulation electrodes. For example, the clinician can interact with GUI 250, such as by using an input mechanism (e.g., cursor or stylus control) to move pointer 260 within GUI 250. In one example, in order to select one or more electrodes 258A-258D as stimulation electrodes, the clinician moves pointer 260 to the one or more electrodes 258A-258D and clicks a button or otherwise provides input to select the electrode. As another example, the clinician can select one or more electrodes 258A-258D as stimulation electrodes by manually inputting an alphanumeric identifier associated with the electrode (e.g., by typing "Electrode 1" into a text box) into a textbox presented by GUI 250, by checking a box associated with the electrode, or using any suitable technique.

Upon receiving the clinician input selecting one or more electrodes 258A-258D, processor 80 of programmer 14 can confirm the electrode selection based on one or more bioelectrical brain signals, as described with respect to FIG. 9. For example, processor 80 can transmit instructions to processor 40 of IMD 16 to control sensing module 46 of IMD 16 (FIG. 2) to sense one or more bioelectrical brain signals with the clinician-selected electrodes or retrieve the sensed bioelectrical brain signal from memory 82. Processor 80 can receive the signal from processor 40 of IMD 16 or memory 82, and determine one or more characteristics of the bioelectrical brain signal to determine whether the bioelectrical brain signal indicates the selected electrodes are proximate the target tissue site or at least distanced from the tissue site associated with a stimulation-induced side effect.

In some examples, the clinician selects one or more electrodes 258A-258D of lead icon 254 as stimulation electrodes based on the position of the electrodes relative to anatomical structures 252 displayed by GUI 250. For example, the clinician can select the electrodes 258A-258D that are displayed proximate one or more target tissue sites and/or not positioned proximate a tissue site related to stimulation-induced side effects. In order to decrease the knowledge required to interact with GUI 250, processor 80 can highlight or otherwise mark the one or more target tissue sites and/or any tissue sites related to stimulation-induced side effects. Processor 80 can highlight the tissue sites by displaying the tissue sites in a different color, by outlining the tissue sites, or using any other technique to help the clinician visually identify the tissue sites.

In addition to or instead of selecting one or more electrodes 258A-258D of lead icon 254 as stimulation electrodes based on the position of electrodes 258A-258D relative to anatomical structures 252, the clinician can select one or more electrodes 258A-258D of lead icon 254 as stimulation electrodes based on therapy field 256. Therapy field 256 represents a region of the patient's tissue to which therapy is delivered when IMD 16 delivers stimulation via a set of stimulation parameter values, such as a particular electrode combination and parameters values that define the stimulation signal (e.g., current or voltage amplitudes, pulse rates, pulse widths, frequency, and/or duty cycle). Processor 80 generates therapy field 256 based on one or more electrodes 258A-258D selected by a clinician (e.g., using the techniques described above) and a set of stimulation parameter values (e.g., current or voltage amplitudes, pulse rates, pulse widths, frequency, and/or duty cycle) stored by memory 82 or inputted by the clinician via user interface 84.

In some examples, therapy field 256 is an electrical field that is generated based upon a patient's anatomy and a therapy program defining stimulation parameter values, and therapy field 256 represents the regions of the patient's anatomical region that will be covered by an electrical field during therapy. For example, processor 80 can generate therapy field 256 based on tissue impedance models, field propagation models, and the like, as described above with respect to FIG. 7 and described in further detail in U.S. Patent Application Publication No. 2007/0203541 by Goetz et al. and U.S. Patent Application Publication No. 2007/0203546 by Stone et al.

In other examples, therapy field 256 is an activation field, which indicates the nerve or muscle tissue, e.g., neurons, that will be activated by the electrical field in the target anatomical region of the patient. Other types of therapy fields 256 that processor 80 can display include a current density field or a voltage gradient field of the electrical field, where the tissue conductivity is determined based on generic human tissue or tissue characteristics specific to patient 12. In some examples of GUI 250, the clinician may be able to switch between any of these types of therapy fields, such as by selecting the type of therapy field from a pull down menu displayed by selecting button 266.

In the example of GUI 250 shown in FIG. 18, therapy field 256 is a cross-sectional view of volumetric electrical field, which may be further defined in other orthogonal views. Although a 2D view of therapy field 256 is shown in FIG. 18, in other examples, processor 80 displays a 3D view of therapy field 256. In this way, GUI 250 can include therapy field 256 that indicates the 3D volume of tissue affected by stimulation delivery according to a selected electrode combination Processor 80 can establish the size and shape of electrical field 256 established based on generic physical characteristics of human tissue and known physical characteristics of the electrodes of the lead 20A or 20B implanted in patient 12. In other words, therapy field 256 displayed in GUI 250 may only be an approximation of what the electrical field would be in brain 28 of a specific patient 12. However, in some examples, physical characteristics of the actual anatomical structure of patient 12 being treated may be used to generate therapy field 256. This anatomical structure information may be stored by memory 82 of programmer 14 as a form of patient anatomical data generated by an imaging modality, such as CT, MRI, or any other volumetric imaging system and stored as patient anatomy data of memory 82 (FIG. 4).

In some examples, the clinician selects one or more electrodes 258A-258D as stimulation electrodes and processor 80 generates and displays therapy field 256 based on the selected electrode combination. The clinician can modify the electrode selection by interacting with user interface 84 (FIG. 3) of programmer 14 if, upon viewing GUI 250, the clinician determines that therapy field 256 does not sufficiently overlap with a target tissue site or overlaps with a tissue site related to stimulation-induced side effects. In response to the user input modifying the electrode selection, processor 80 can update therapy field 256 and display the updated therapy field, such that the clinician can view how the modification to the stimulation electrode selection affected the therapy field.

Instead of or in addition to selecting electrodes by identifying the specific electrode within GUI 250 (e.g., by moving pointer 260 to the electrode to be selected and clicking on the electrode with a mouse or another peripheral pointing device), a clinician can select one or more electrodes 258A-258D by adjusting therapy field 256. Processor 80 can then determine the stimulation electrodes that are required to achieve the therapy field 256. In addition, in some examples, processor 80 also determines other stimulation parameter values (e.g., stimulation amplitude or frequency) that are required to achieve the therapy field 256.

The clinician may also move therapy field 256 along the length of lead icon 254 and processor 80 may automatically select which electrode levels to activate to produce the therapy field 256. In addition, in the example shown in FIG. 18, the clinician (or other user) may use pointer 260 to drag therapy field 256 to define a smaller or larger size, which corresponds to a lower or higher voltage or current amplitude. For example, the user may click on a border, or perimeter of therapy field 256, and then drag the border to expand or contract the field 256. Additionally or alternatively, the clinician can use pointer 260 to move control slide 270 up to slightly increase the size of therapy field 256 or down to slightly decrease the size of therapy field 256. In some examples, processor 80 displays the actual electrodes 258A-258D or other stimulation parameter values associated with therapy field 256 in GUI 250 as therapy field 256 changes characteristics.

Processor 80 of programmer 14 may limit the rate of movement of therapy field 256. In other words, therapy field 256 may only be moved a certain number of steps per second within GUI 250, or any other user interface that allows the clinician to drag the therapy field. This rate movement limit may prevent unnecessary calculations by processor 80.

In some examples, processor 80 determines the initial size of therapy field 256 by a minimal threshold voltage previously determined to provide some efficacious results to patient 12. The size of therapy field 256 may be limited by a volume parameter value or a maximum voltage limit previously defined by the user or processor 80. The limit may be associated with capabilities of IMD 16 or safe voltage or current levels for patient 12. Once the maximum size of therapy field 256 is met, the clinician may no longer be able to drag the size of the therapy field away from lead icon 254. Therapy field 256 may grow in size or split if the clinician selects more than one electrode level 258A-258D. Processor 80 can make these determinations based on the equations used to generate therapy field model 256.

Example devices, systems, and techniques with which the clinician can adjust modify therapy field 256 are described in further detail in U.S. Patent Application Publication No. 2007/0203541 by Goetz et al. and U.S. Patent Application Publication No. 2007/0203546 by Stone et al. In accordance with systems and techniques described in U.S. Patent Application Publication No. 2007/0203541 by Goetz et al., processor 80 of programmer 18 may present a user interface to a user that enables the user to manipulate a representation of an electrical stimulation field (i.e., one type of therapy field) produced by therapy delivery via a selected electrode combination. Processor 80 may then select the appropriate electrode combination, electrode polarities, amplitudes, pulse widths, and pulse rates of electrical stimulation that best fit a stimulation field created by a user via a user interface of programmer 14.

After determining one or more electrodes 258A-258D that results in a satisfactory therapy field 256, the clinician can select button 268 in order to confirm the electrode selection. Upon receiving the clinician input, processor 80 of programmer 14 can confirm the electrode selection based on one or more bioelectrical brain signals, as described with respect to FIG. 9. For example, processor 80 can transmit instructions to processor 40 of IMD 16 to control sensing module 46 of IMD 16 (FIG. 2) to sense one or more bioelectrical brain signals with the clinician-selected electrodes. Processor 80 can receive the signal from processor 40 of IMD 16 and determine one or more characteristics of the bioelectrical brain signal to determine whether the bioelectrical brain signal indicates the selected electrodes are proximate the target tissue site or at least distanced from the tissue site associated with a stimulation-induced side effect.

In other examples, programmer 14 can display a physiological model that includes other types of data, such as only a graphical representation of one or more anatomical structures 252 of brain 28 of patient 12 and lead icon 254, in which case the physiological model can be referred to as an anatomic model. As another example, the physiological model can include only the graphical representation of one or more anatomical structures 252 of brain 28 and therapy field model 256, in which case the physiological model can be referred to as a therapy field model. Another type of therapy field model includes only the graphical representation of therapy field model 256 and lead icon 254. Processor 80 of programmer 14 (or another computing device) can generate a physiological model that includes any suitable information pertinent to conveying tissue proximate electrodes 24, 26 of implanted leads 20.

A computing device, such as programmer 14, can present a plurality of GUIs with which a user may interact to program IMD 16. Programming of IMD 16 can include, for example, selecting one or more stimulation parameter values that define the stimulation signal that IMD 16 generates and delivers to patient 12, and/or selecting one or more stimulation electrodes with which IMD 16 delivers electrical stimulation to a target tissue site within brain 28 (FIG. 1) of patient 12. FIGS. 19A-19M are conceptual diagrams of example graphical user interface screens displayed by user interface 84 of programmer 14. The graphical user interface screens each provide an interface with which a user can interact to select one or more stimulation electrodes with which IMD 16 delivers therapy to patient 12 based on one or more bioelectrical brain signals sensed in a brain of a patient with respective sense electrode combinations and one or more physiological models that indicate one or more characteristics of tissue proximate the electrode within the brain of the patient. The screens shown in FIGS. 19A-19M illustrate GUIs with which a user can interact with processor 80 of programmer 14 to select one or more stimulation electrodes.

Figure 19A:
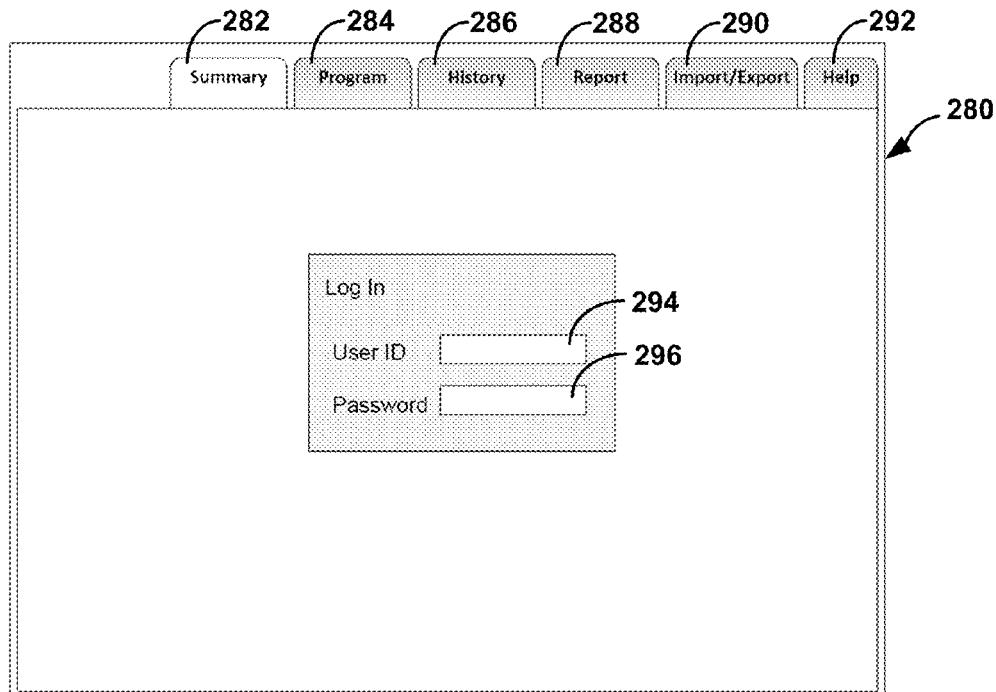
FIGS. 19A-19M are screen diagrams illustrating example graphical user interfaces displayed by a programmer.

FIG. 19A is a conceptual diagram of GUI 280, which processor 80 of programmer 14 can present via a display of user interface 84 of programmer 14. GUI 280 includes a plurality of tabs 282, 284, 286, 288, 290, 292. A user can select one of the tabs 282, 284, 286, 288, 290, 292 to access different features of programmer 14. A user can select a tab 282, 284, 286, 288, 290, 292 by, for example, using a peripheral pointing device (e.g., a mouse, stylus or finger in the case of a touch screen) to move a cursor within GUI 280 over the tab and provide input selecting the tab by, e.g., clicking a button of a mouse, double clicking the tab icon, pressing down on the displayed tab, depressing an enter button on a keypad or keyboard, and the like. In other examples, the user can select a tab 282, 284, 286, 288, 290, 292 by manually typing in the name associated with the tab into a text box presented by GUI 280 or using another technique.

Upon selection of each of the tabs 282, 284, 286, 288, 290, 292 by a user, processor 80 of programmer 14 presents a respective graphical user interface screen with which a user can program IMD 16 or access and/or enter patient data for storage by memory 82 of programmer 14 or another memory (e.g., a remote database). For example, upon receiving user input selecting summary tab 282, processor 80 can display information for initiating the IMD programming process, such as a screen with which the user can select a patient and/or therapy system hardware information. In addition, in some examples, within summary tab 282, processor 80 can provide information about the current model of leads 20 implanted in patient 12, the current model of IMD 16 implanted in patient 12, and, if relevant, the current stimulation parameter values with which IMD 16 delivers therapy to patient 12. Further, in some examples, processor 80 can provide information about the lead integrity (e.g., results of recent electrode impedance tests) and battery status. Summary tab 282 can also include one or more screens for displaying patient information, such as any one or more of the patient name, age, weight, height, diagnoses, medications, or the like.

Upon selection of program tab 284, processor 80 can present one or more graphical user interface screens with which the user can interact to select one or more stimulation parameter values and/or electrode combinations, as described with respect to FIGS. 19E-19I. In some examples, the programming screens can provide guided programming of IMD 16 in the sense that processor 80 presents the screens in a predetermined order that guides the user through the different steps (e.g., steps associated with the selection of a respective therapy parameter value) of the programming of IMD 16. In other examples, processor 80 may not present the screens in any particular order and may merely provide a menu from which the user selects the desired programming screen. In some examples, in either case, processor 80 may permit the user to move through the different programming screens in any particular order.

Upon selection of history tab 286, processor 80 can provide information about the current and/or previous programming sessions for the particular patient, and, in some cases, physiological parameter values of patient 12 sensed by IMD 16 or another implanted or external medical device. A user can select report tab 288 to view a report relating to the current programming session for patient 12, and, in some cases, past programming sessions for patient 12. Processor 80 can provide the user with different report formats, such as graphs and pie charts, and, in some examples, processor 80 can present screens with which the user can manipulate the data in different manners (e.g., to generate different statistics about therapy delivery by IMD 16, such as the percentage of time IMD 16 delivered therapy according to a particular therapy program).

Upon receiving user input selecting import/export tab 290, processor 80 can import data from another device, such as IMD 16 or a remote database, via telemetry module 86 (FIG. 4) which can store information about patient 12 (e.g., the patient condition, the type of IMD 16 and leads 20 implanted in patient 12, and so forth). In addition to or instead of importing information from another device, upon receiving user input selecting import/export tab 290, processor 80 can export data to another device (e.g., IMD 16, a remote or local computing device, or a printer) via telemetry module 86 (FIG. 4). The data can include, for example, one or more therapy parameter values or stimulation electrodes selected during the programming session. Programmer 14 can also include a help option, whereby a user can input a question and processor 80 can search a database for an answer. To access this feature of programmer 14, a user can select help tab 292.

In the example shown in FIG. 19A, upon receiving user input selecting summary tab 282, as shown in FIG. 19A, processor 80 presents a GUI 280, which prompts the user for a user identification (ID) 294 and password 296. However, in some examples, processor 80 can present GUI 280 as the first screen after start-up of programmer 14. IMD programming can be confidential in nature, and, therefore, it may be desirable to provide security measures for accessing the programming data. Moreover, it may be desirable to limit access to the programming functions of programmer 14 in order to minimize the possibility of an unauthorized user from programming IMD 16.

Figure 19B:
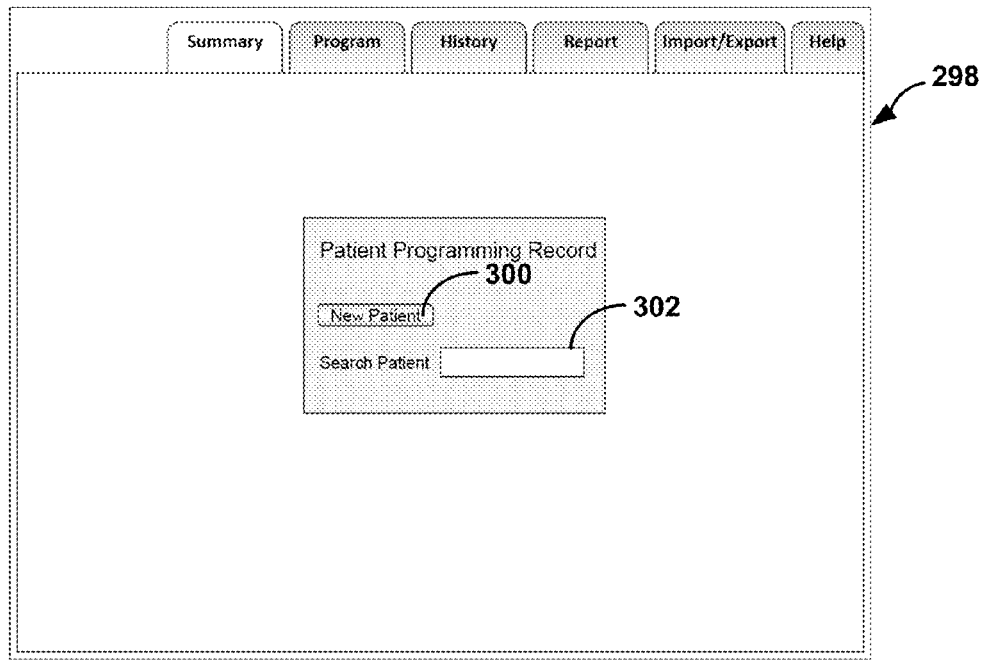
Figure 19C:
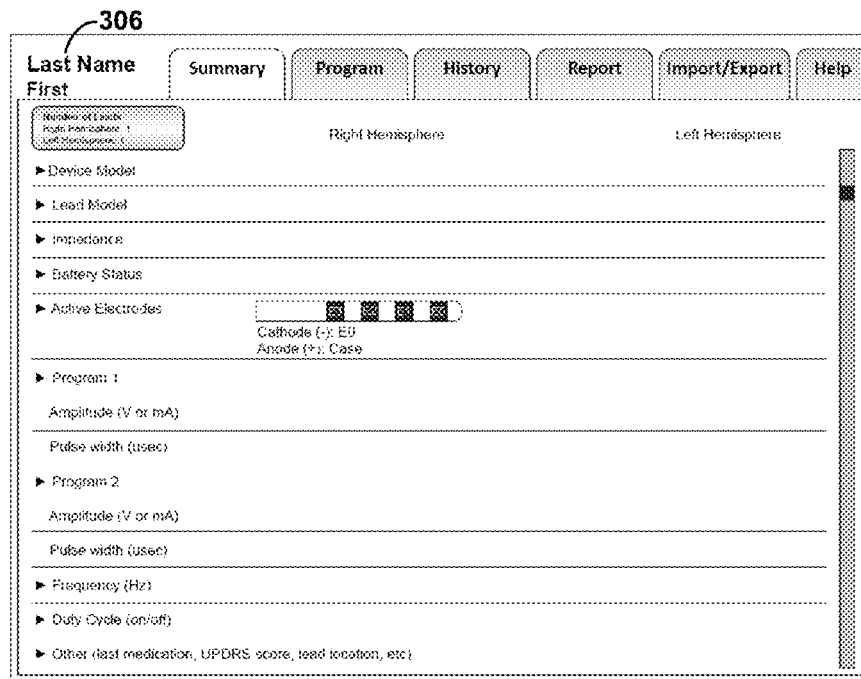

After confirming the user identification 294 and password 296 provided by the user are authorized (e.g., by comparing the identification and password to user information stored in memory 82 of programmer 14 or a remote database), processor 80 can present GUI 298, a conceptual diagram of which is shown in FIG. 19B. GUI 298 includes a virtual button 300 that the user can select to enter data for a new patient. Example data includes, but is not limited to, identifying information (e.g., the patient name, address, and phone number) patient health information (e.g., patient condition, age, weight, and height), and information about therapy system 10 implanted in patient 12 (e.g., the model of IMD 16 and leads 20 and/or the implant location of leads 20). GUI 298 also includes text box 302 in which the user can enter a patient name or other identifier (e.g., a patient number) to search for a patient that may have an existing file. The user can provide alphanumeric input via user interface 84 of programmer 14, which can include a keyboard, keypad, a microphone and voice recognition software that translates voice input into text or numbers, or any other suitable input mechanism for receiving input from a user.

After receiving user input indicating a patient for which the programming session is implemented, processor 80 can present GUI 304, which indicates the patient name 306, and summarizes information relating to patient 12. In the example shown in FIG. 19C, the summary GUI 304 includes information about the number of leads 20 implanted in patient 12, the location of the leads, the model of IMD 16 and leads 20, the impedance of one or more electrical paths of leads 20 including at least one electrode 24, 26 (which can indicate lead integrity), the battery status (e.g., an estimate of the remaining battery life), the active electrodes 24, 26 from which one or more simulation electrodes can be selected, and the therapy programs currently selected for patient 12. GUI 304 may also include a miscellaneous section that lists the medications prescribed for patient 12, and the patient diagnosis. In the example shown in FIG. 19C, the patient diagnosis is indicated by the Unified Parkinson's Disease Rating Score (UPDRS). However, the patient diagnosis may differ depending on the patient condition for which IMD 16 is implemented to manage.

Figure 19D:
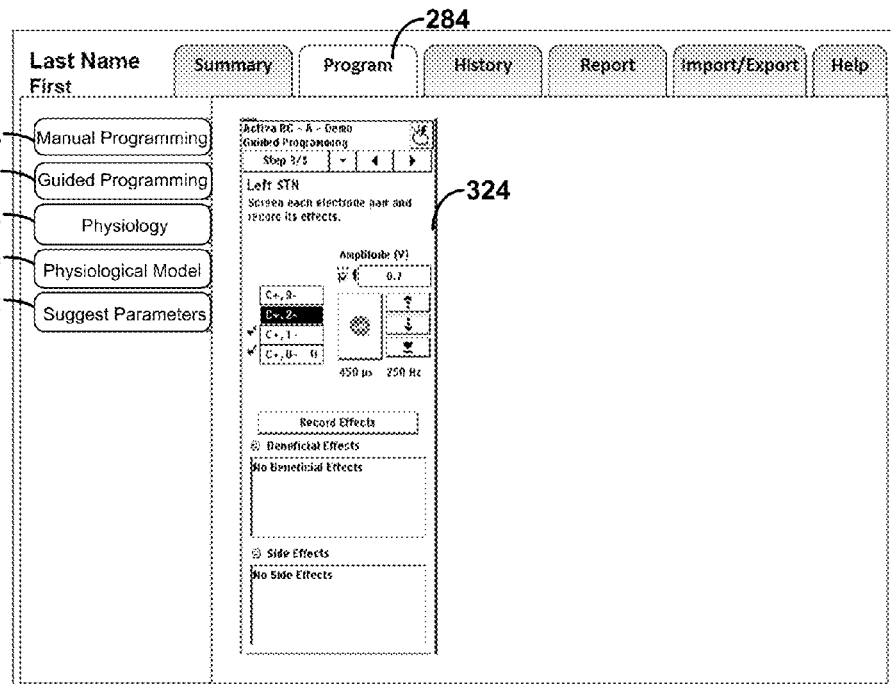

FIG. 19D is a conceptual illustration of a programming GUI 310 presented by processor 80 of programmer 14. In one example, upon selection of program tab 284, processor 80 can present GUI 310, which includes menu 312 of programming options for selection by the user. Menu 312 includes manual programming button 314, guided programming button 316, a physiology button 318, and a physiological model button 320. Each of buttons 314, 316, 318, 320 are associated with a different programming technique, which can differ from each other based on the level of user control of the stimulation parameter value or electrode selection permitted by processor 80 of programmer 14 or the type of information presented by processor 80 for guiding the programming of IMD 16 by the user. Upon receiving user input selecting each of buttons 314, 316, 318, 320 (e.g., using the techniques described above with respect to selecting a tab 282, 284, 286, 288, 290, 292), processor 80 can display a respective GUI screen on a display of user interface 84. Examples of the GUIs for programming IMD 16 are described with respect to FIGS. 19E-19I.

Menu 312 also includes a suggest parameters button 322. As discussed in further detail below with respect to FIG. 19I, upon receiving user input selecting suggest parameters button 322, processor 80 can generate and display a GUI screen which may suggest stimulation electrodes that may provide efficacious stimulation to patient 12 and, in some examples, stimulation parameter values for efficacious therapy delivery to patient 12 (e.g., therapy delivery that provides therapeutic benefits and minimizes side effects).

In the example shown in FIG. 19D, processor 80 presents GUI 310 associated with the manual programming option 314. GUI 310 includes programming screen 324 with which the user can select different electrodes and other stimulation parameter values (e.g., amplitude, pulse width, and/or frequency), deliver test stimulation to patient 12 with the selected electrodes and stimulation parameter values, and determine and record the effects of the stimulation on patient 12. Upon selection of guided programming option 316, processor 80 can present a GUI with a programming screen similar to programming screen 324. However, the guided programming features of programmer 14 can differ from manual programming option 314 in that processor 80 may exercise more control over the order in which the user selects values for at least some of the stimulation parameters.

Figure 19E:
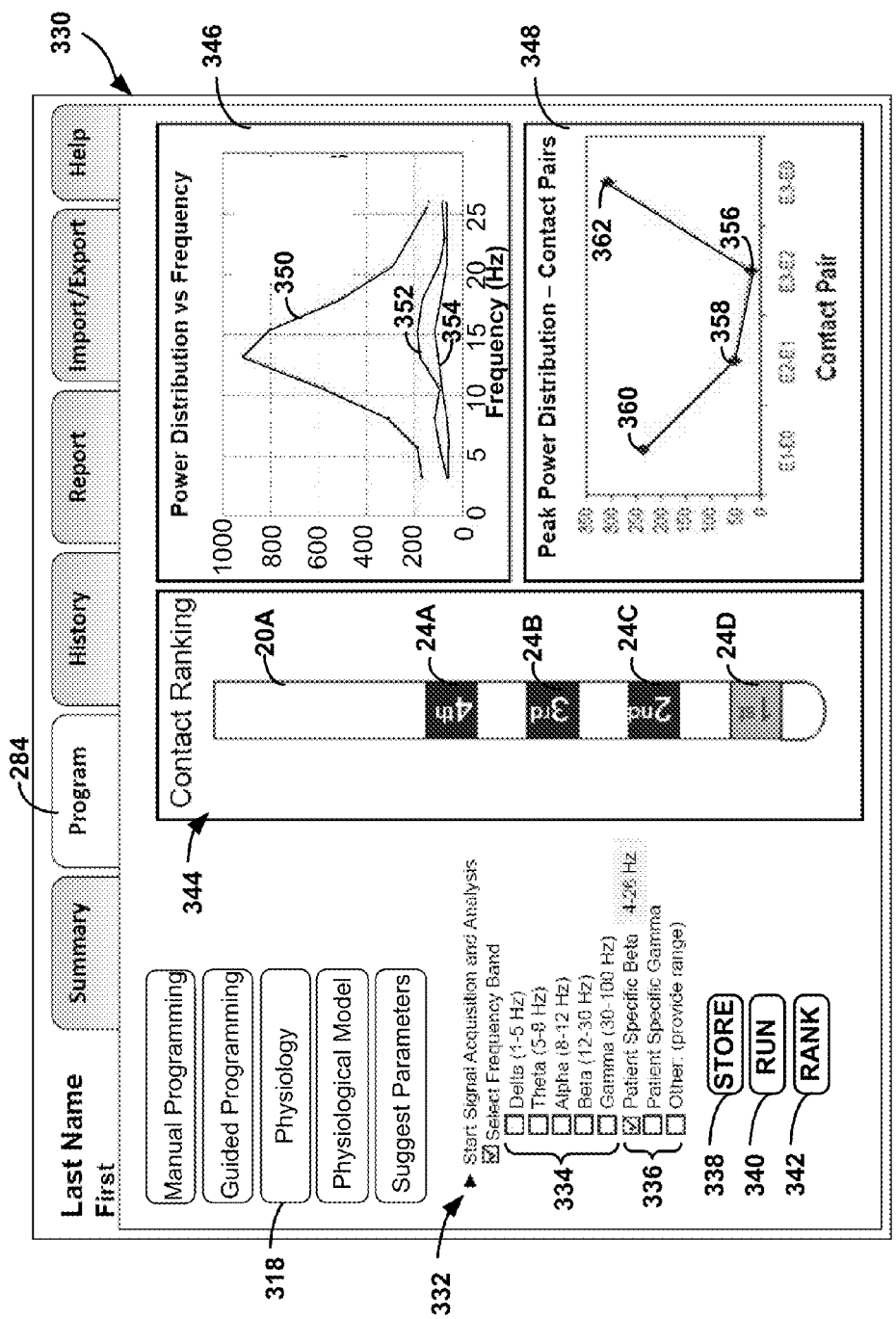

In some examples, upon receiving user input selecting physiology programming option 318, processor 80 may present GUI 330, which a schematic diagram of which is shown in FIG. 19E. Physiology programming option 318 permits a user to evaluate one or more electrodes of one or both leads 20 based on bioelectrical brain signals sensed with the electrodes, as described above with respect to FIGS. 12, 13, 15A-15C, 16, and 17. GUI 330 provides a user interface with which a user may interact to control IMD 16 to sense one or more bioelectrical brain signals via implanted electrodes. In the example shown in FIG. 19E, the user, manually or with the aid of processor 80, may select one or more stimulation electrodes from an array of implanted electrodes and/or at least rank the stimulation electrodes of one or both leads 20 based on bioelectrical brain signals sensed with the electrodes.

In the example GUI 330 shown in FIG. 19E, GUI 330 provides an interface with which the user may evaluate stimulation electrodes 24 of a single lead 20A. In other examples, processor 80 can display a GUI similar to GUI 330 with which a user may interact to select and/or rank stimulation electrodes of another lead (e.g., lead 20B) or multiple leads (e.g., if multiple leads are implanted in patient 12, as shown in FIG. 1) at a time. Thus, in some examples, GUI 330 can include a schematic illustrate of other lead configurations can be schematically illustrated in GUI 330, such as a lead configuration including two leads 20A, 20B with respective sets of electrodes 24, 26. FIGS. 19E-19I are primarily described with respect to selecting stimulation electrodes from array of electrodes 24 of lead 20A for ease of description.

GUI 330 includes a menu with which the user can select the frequency band of interest of the bioelectrical brain signal sensed by IMD 16. As previously indicated, a bioelectrical brain signal may include an EEG, ECoG, single cell recording, or LFP. In some examples, sensing module 46 (FIG. 2) of IMD 16 includes a frequency selective sensing circuit that extracts the energy level within one or more selected frequency bands of a sensed patient parameter signal, which may be, for example, a bioelectrical brain signal. Thus, in some examples, upon selection of frequency band via menu 332, processor 80 can control sensing module 46 to extract the energy level within the user-selected frequency bands of the bioelectrical brain signal.

In some examples, the frequency selective sensing circuit of sensing module 46 can include a chopper-stabilized superheterodyne instrumentation amplifier and a signal analysis unit, and may utilize a heterodyning, chopper-stabilized amplifier architecture to convert a selected frequency band of a physiological signal, such as a bioelectrical brain signal, to a baseband for analysis. The physiological signal may be analyzed in one or more selected frequency bands to determine one or more features as described herein. In some examples, sensing module 46 (FIG. 2) of IMD 16 includes a plurality of channels that extract the same or different frequency bands of one or more signals indicative of one or more patient parameters.

Examples of various additional chopper amplifier circuits that may be suitable for or adapted to the techniques, circuits and devices of this disclosure are described in U.S. Pat. No. 7,385,443 to Denison, which is entitled "CHOPPER STABILIZED INSTRUMENTATION AMPLIFIER" and issued on Jan. 10, 2008, the entire content of which is incorporated herein by reference. Examples of frequency selective monitors that may utilize a heterodyning, chopper-stabilized amplifier architecture are described in U.S. Provisional Application No. 60/975,372 by Denison et al., entitled "FREQUENCY SELECTIVE MONITORING OF PHYSIOLOGICAL SIGNALS," and filed on Sep. 26, 2007, commonly-assigned U.S. Provisional Application No. 61/025,503 by Denison et al., entitled "FREQUENCY SELECTIVE MONITORING OF PHYSIOLOGICAL SIGNALS, and filed on Feb. 1, 2008, and commonly-assigned U.S. Provisional Application No. 61/083,381, entitled, "FREQUENCY SELECTIVE EEG SENSING CIRCUITRY," and filed on Jul. 24, 2008. The entire contents of above-identified U.S. Provisional Application Nos. 60/975,372, 61/025,503, and 61/083,381 are incorporated herein by reference. Further examples of chopper amplifier circuits are also described in further detail in commonly-assigned U.S. Patent Application Publication No. 2009/0082691 by Denison et al., entitled, "FREQUENCY SELECTIVE MONITORING OF PHYSIOLOGICAL SIGNALS" and filed on Sep. 25, 2008. U.S. Patent Application Publication No. 2009/0082691 by Denison et al. is incorporated herein by reference in its entirety.

A sensing module 46 that directly extracts energy in key frequency bands of a bioelectrical brain signal may be used to extract bandpower at key physiological frequencies with an architecture that is flexible, robust, and relatively low-noise. Chopper stabilization is a noise and power efficient architecture for amplifying low-frequency neural signals in micropower applications (e.g., an implanted device) with excellent process immunity. Chopper stabilized amplifiers can be adapted to provide wide dynamic range, high-Q filters. A sensing module 46 that includes a chopper-stabilized amplifier may slightly displace the clocks within the chopper amplifier in order to re-center a targeted band of energy to direct current (DC) in a manner similar to super-heterodyne receivers used in communication systems. In some examples, extracting the bandpower within a selected frequency band requires two parallel signal paths (in-phase and quadrature) that are combined within the power extraction stage. The power output signal can be lowpass filtered, which results in an output that represents the spectral power fluctuations in the frequency band.

Frequency selection menu 332 includes boxes with which the user can select from predetermined frequency bands 334, which may be patient non-specific, or patient specific frequency bands or an otherwise user-specified frequency band 336. For example, the user can provide input, e.g., via a peripheral pointing device, touch screen or another input mechanism, to check a box next to the frequency band of interest shown in menu 332. If the frequency band of interest is not displayed, in some examples, the user can provide input, e.g., via a keyboard, keypad or another input mechanism, to select a frequency band.

Different frequency bands are associated with different activity in brain 28 of patient 12. It is believed that some frequency band components of a bioelectrical brain signal sensed within brain 28 may be more revealing of a particular patient condition (e.g., symptoms) and abnormal brain activity symptoms of the patient condition than other frequency components. A user can select a frequency band from menu 332 or input a patient-specific frequency band based on the patient condition for which IMD 16 is implemented to manage. One example of the frequency bands is shown in Table 1:

TABLE 1

Frequency bands

| Frequency (f) Band Hertz (Hz) | Frequency Information |
|---|---|
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

The frequency ranges for the frequency bands shown in Table 1 are merely examples. The frequency ranges may differ in other examples. For example, another example of frequency ranges for frequency bands are shown in Table 2:

TABLE 2

Frequency bands

| Frequency (f) Band Hertz (Hz) | Frequency Information |
|---|---|
| f < 5 Hz | δ (delta frequency band) |
| 5 Hz ≤ f ≤ 8 Hz | q (theta frequency band) |
| 8 Hz ≤ f ≤ 12 Hz | α (alpha frequency band) |
| 12 Hz ≤ f ≤ 16 Hz | s (sigma or low beta frequency band) |
| 16 Hz ≤ f ≤ 30 Hz | High β (high beta frequency band) |
| 50 Hz ≤ f ≤ 100 Hz | γ (gamma frequency band) |
| 100 Hz ≤ f ≤ 200 Hz | high γ (high gamma frequency band) |

In one example, a user may select the frequency band of a bioelectrical brain signal for selecting stimulation electrode combinations based on information specific to patient 12 or based on data gathered from more than one patient 12. As described above, the frequency bands that are useful for identifying a target tissue site for stimulation to manage a patient condition can be specific to a particular patient 12 or general to a group of patients with similar conditions. Processor 80 may, in some examples, suggest a frequency band to extract from a sensed bioelectrical brain signal based on a patient condition indicated by the user. In some examples, some electrodes 24 may only sense or only deliver stimulation, in which case processor 80 may indicate such constraints on the electrode combinations with which IMD 16 may sense bioelectrical brain signals via GUI 330.

GUI 330 also includes store button 338, run button 340, and rank button 342. Buttons 334, 336, 342 as well as other buttons of other GUIs described herein, are displayed as selectable objects (e.g., also referred to herein as buttons or virtual buttons) within the respective GUI. A user can select buttons 334, 336, 342 using any suitable technique, such as by moving a cursor within GUI 330 over the desired button 334, 336, 342 and double clicking the cursor over the selected button, by selecting an enter button (e.g., on a keyboard or keypad) while the cursor is over the selected button, or using any other suitable technique. In other examples, buttons 334, 336, 342 are not objects displayed within GUI 330, but are dedicated physically depressible buttons or soft keys that are a part of user interface 84 of programmer 14.

Upon receiving user input selecting run button 340, processor 80 of programmer 14 may control sensing module 46 of IMD 16 to sense a plurality of bioelectrical brain signals with electrodes 24 of lead 20A, e.g., using one or more of the techniques described with respect to FIGS. 12, 13, 15A-15C, 16, and 17. For example, processor 80 of programmer 14 may control sensing module 46 of IMD 16 to sense a bioelectrical brain signal with each electrode 24 of lead 20A in a unipolar configuration or with each combination of electrodes 24 of lead 20A in a bipolar configuration. In some examples, upon receiving user input selecting run button 340, processor 80 may transmit instructions (e.g., a signal) to processor 40 of IMD 16, which can then control sensing module 46 to sense the bioelectrical brain signals. The instructions may be transmitted from programmer 14 to IMD 16 via the respective telemetry modules 86, 50.

After IMD 16 senses the bioelectrical brain signals, e.g., using one or more of the techniques described with respect to FIGS. 12, 13, 15A-15C, 16, and 17, the user can rank the electrodes based on the proximity of electrodes to a target tissue site. In the example GUI 330 shown in FIG. 19E, the user can select rank button 342 in order to provide input to processor 80 indicating that a ranking of electrodes 24 is desired. In response to receiving user input selecting rank button 342, processor 80 may determine whether the user has selected a frequency band for signal analysis via menu 332. If a frequency band has not been selected, processor 80 can analyze the bioelectrical brain signals based on a default frequency band stored by memory 82. In other examples, if frequency band has not been selected, processor 80 may prompt the user to select a frequency band, such as by displaying a textual prompt to the user and/or highlighting menu 332.

Upon receiving user input selecting rank button 342, processor 80 automatically ranks electrodes 24 based on at least one characteristic of the bioelectrical brain signals sensed by sensing module 46 of IMD 16. In some examples, processor 80 ranks electrodes 24 based on the proximity of the electrodes to the target tissue site, which can be indicated by the power level within the user-selected frequency band of a bioelectrical brain signal sensed with the electrode. Example techniques processor 80 can implement to automatically rank the electrodes 24, 26 based on the proximity to the target tissue site is described in further detail in U.S. patent application Ser. Nos. 12/639,717 and 12/639,678 by Molnar et al. In other examples, processor 80 implements one or more of the techniques described with respect to FIGS. 12, 13, 15A-15C, 16, and 17 to determine which electrodes 24, 26 are closest to the target tissue site.

As described in further detail in U.S. patent application Ser. Nos. 12/639,717 and 12/639,678 by Molnar et al., in some examples, the proximity of an electrode to a target tissue site can be determined based on the relative band power (or energy) level in a selected frequency band (e.g., indicated by the frequency band selection in menu 332). The relative band power may be a ratio of the power in a beta band of the sensed signal to the overall power of the sensed signal. Thus, in some examples, processor 80 ranks the electrode 24 with which sensing module 46 of IMD 16 sensed a bioelectrical brain signal with the greatest relative beta band power as the electrode closest to the target tissue site.

In other examples, as described in further detail in U.S. patent application Ser. Nos. 12/639,717 and 12/639,678 by Molnar et al., in order to determine the proximity of an electrode to a target tissue site, processor 80 can implement an algorithm, such as the one described with respect to FIGS. 15A-15C, which indicates which electrode is closest to a target tissue site when the target tissue site for therapy delivery may be located between two sense electrodes. If the target tissue site is located directly between two sense electrodes, determining which of the sense electrodes is closest to the target tissue site may require a more complex technique than simply determining the electrode or electrodes that sensed the bioelectrical signal with the highest relative power level within the selected frequency band. In examples described herein, processor 80 can execute an algorithm (which can be stored as instructions stored by memory 82 or another memory) that determines whether the target tissue site is located between sensed electrodes may be applied to determine the electrode or electrodes that are located closest to a target tissue site. The algorithm further includes determining a plurality of relative values of the relative beta band power level, where each relative value is based on the relative beta band power levels of two bioelectrical signals sensed by two different electrodes, and selecting the sense electrode or electrodes that are closest to the target tissue site based on the plurality of relative values.

In some examples, GUI 330 includes a graphical representation 344 of the one or more leads implanted inpatient 12 (in the example shown in FIG. 19E, only one lead is shown for ease of illustration), and data relating to the bioelectrical brain signals. For example, in the example shown in FIG. 19E, GUI 330 includes graph 346 illustrating the power distribution of the bioelectrical brain signals sensed via each of the different groups of electrodes of the implanted lead and graph 348, which illustrates the peak power level sensed by the different groups of electrodes of the implanted lead. In other examples, processor 80 can include other types of graphs in GUI 330, such as graphs of other formats (e.g., a line graph) or a graph providing other types of information.

After automatically ranking electrodes 24, processor 80 can update the different data screens of GUI 330. For example, in the example shown in FIG. 19E, processor 80 updates graphical representation 344 of lead 20A and electrodes 24 to indicate a ranking of electrodes 24 relative to the target tissue site. In the example GUI 330 shown in FIG. 19E, processor 80 determined that electrode 24D is closest to the target tissue site, electrode 24C is second closest to the target tissue site, electrode 24B is third closest to the target tissue site, and electrode 24A is the fourth closest to the target tissue site. GUI 330 includes textual indication of the electrode ranking, such that a user can view GUI 330 and ascertain relatively quickly which electrodes 24 are closest to the target tissue site according to the bioelectrical brain signal sensed via the electrodes. Other indications of the electrode ranking can also be used in other examples. For example, in other examples, processor 80 can color code the graphical representations of electrodes 24 based on the determined proximity to the target tissue site.

The order in which electrodes 24 are ranked may or may not necessarily indicate which electrode may provide the most efficacious stimulation therapy. For example, although electrode 24D is closest to a target tissue site in the example shown in FIG. 19E, it may later be determined that stimulation therapy delivered via electrode 24D results in stimulation-induced side effects not present when stimulation therapy is delivered via electrode 24C. In such a case, the user or processor 80, based on user input indicating the side effects, may select the next-highest electrode or a different electrode to deliver stimulation.

Processor 80 can rank the electrodes based on the proximity to the target tissue site when the electrodes are displaced in a direction substantially along a longitudinal axis of lead 20A, as shown in FIG. 19E. In addition, in some examples, processor 80 can rank the electrodes based on the proximity to the target tissue site when the electrodes are arranged in a direction other than a direction indicated by the longitudinal axis of one or both leads 20. For example, processor 80 can implement one or more of the algorithms described with respect to FIGS. 16 and 17 help to identify the location of a target tissue site in a direction indicated by each of a plurality of segmented or partial ring electrodes that share an axial position along a longitudinal axis of a lead, but have different radial positions (e.g., a direction substantially perpendicular to the longitudinal axis of the lead). In these examples, graphical representation 344 of lead 20A can be updated to include the relevant electrode arrangement and the ranking of the electrodes.

Graph 346 illustrates the power distribution of the bioelectrical brain signals sensed via each of the different groups of electrodes 24 of implanted lead 20A. In particular, in the example shown in FIG. 19E, graph 346 illustrates the power distribution of first bioelectrical brain signal 350 sensed with electrodes 24D and 24C in a bipolar electrode configuration, second bioelectrical brain signal 352 sensed via electrodes 24C and 2B in a bipolar configuration, and third bioelectrical brain signal 354 sensed via electrodes 24B and 24A in a bipolar configuration. Graph 346 may provide useful information related to the relative power levels of bioelectrical brain signals 350, 352, 354 sensed via electrodes 24, and the distribution of the power levels relative to more than one frequency band. A user may, for example, determine relatively quickly based on graph 346 that first bioelectrical brain 350 signal sensed via electrodes 24D and 24C had a much higher overall power level than third bioelectrical brain signal 354 sensed via electrodes 24B and 24A. The user can also determine relatively quickly based on graph 346 that first bioelectrical brain signal 350 sensed via electrodes 24D and 24C had a much higher overall power level within a specific frequency band than third bioelectrical brain signal 354 sensed via electrodes 24B and 24A.

Graph 348 illustrates the relative values of relative beta band power levels of each electrode combination of lead 20A (including electrodes 24A-24D) for a scenario in which the target tissue site is located closest to electrode 24D. In the example shown in FIG. 19E, both graphs 346 and 348 were generated using Microsoft Office Excel, made commercially available by Microsoft Corporation of Redmond, Wash. The target tissue site was modeled as a point source and the extracellular electrical potentials sensed by each of the sense electrodes were determined using the following equation:

$$Ve = \frac{Isrc}{4\pi\sigma r}$$

where Ve is the extracellular potential, Isrc (Isource) is the magnitude of the modeled point source, σ is the conductivity of the extracellular medium tissue and r is the distance between the point source and the recording site. In this case, σ was modeled as 0.23 Siemens per meter and r was modeled as 1 millimeter from a longitudinal axis of a lead on which the electrodes are positioned. The electrical potentials (e.g., which can be representative of bioelectrical brain signals) were sensed at four locations along a linear lead. Three millimeter spacing between each location was used to model the spacing between electrodes on one type of commonly-used linear lead, which includes multiple electrodes with three millimeter spacing between each. In other examples, electrodes may have different spacing, e.g., two millimeters.

Graph 348 illustrates the relative values of the relative beta band power level for a plurality of electrode combinations, whereby the relative value of the relative beta band power level indicates the absolute difference in a beta band power level of a first bioelectrical brain signal sensed with a first electrode in a unipolar configuration and a beta band power level of a second bioelectrical brain signal sensed with a second electrode 24D in a unipolar configuration. In the example shown in FIG. 19E, graph 348 illustrates a scenario in which electrode combination 24A-24B has a relative value 356 of approximately 12.9243 milliVolts (mV), electrode combination 24B-24C has a relative value 358 of approximately 29.3284 mV, electrode combination 24C-24D has a relative value 360 of approximately 116.865 mV, and electrode combination 24A-24D has a relative value 262 of approximately 159.117 mV. Because relative value 360 is greater than relative value 358 and relative value 358 is greater than relative value 356, processor 80, when implementing an algorithm such as the one shown in FIGS. 15A-15C determines that the target tissue site is closest to electrode 24D compared to electrodes 24A-24C.

After the user determines bioelectrical brain signals and ranks the electrodes based on a frequency domain characteristic within the frequency band selected by the user via menu 332, the user can store the electrode ranking by selecting store button 338. Upon receiving user input selecting store button 338, processor 80 may store the current ranking of electrodes 24 displayed by graphical representation 344 of lead 20A illustrated by GUI in memory 82 of programmer 14 or a memory of another device. Instead of or in addition to storing the electrode ranking, the user may elect to rerun the electrode ranking based on the proximity to the target tissue site as indicated by a different frequency domain characteristic within the frequency band selected by the user via menu 332. The user can select another frequency band via menu 332 and then select run button 340.

The user may rerun the bioelectrical brain signal sensing via the different combinations of electrodes 24 for various reasons. For example, the user may review graph 346 and determine that the power distribution of each of the bioelectrical brain signals within the selected frequency band is relatively the same, thereby indicating that the selected frequency band is not useful for ranking electrodes 24. As another example, the user may review graph 348 and determine that the peak power distribution of the different pairs of electrodes 24 is relatively the same or at least at a level that does not help rank electrodes 24 based on their proximity to the target tissue site. In some examples, trial and error may be utilized to determine the specific frequency band that is revealing of the target tissue site and useful to distinguish between the proximity of electrodes 24 to a target tissue site. While the user may know than a broad frequency band is revealing of the target tissue site associated with a particular patient condition, the specific sub-frequency band may not be known until one or more trial rankings are executed via GUI 330.

Figure 19F:
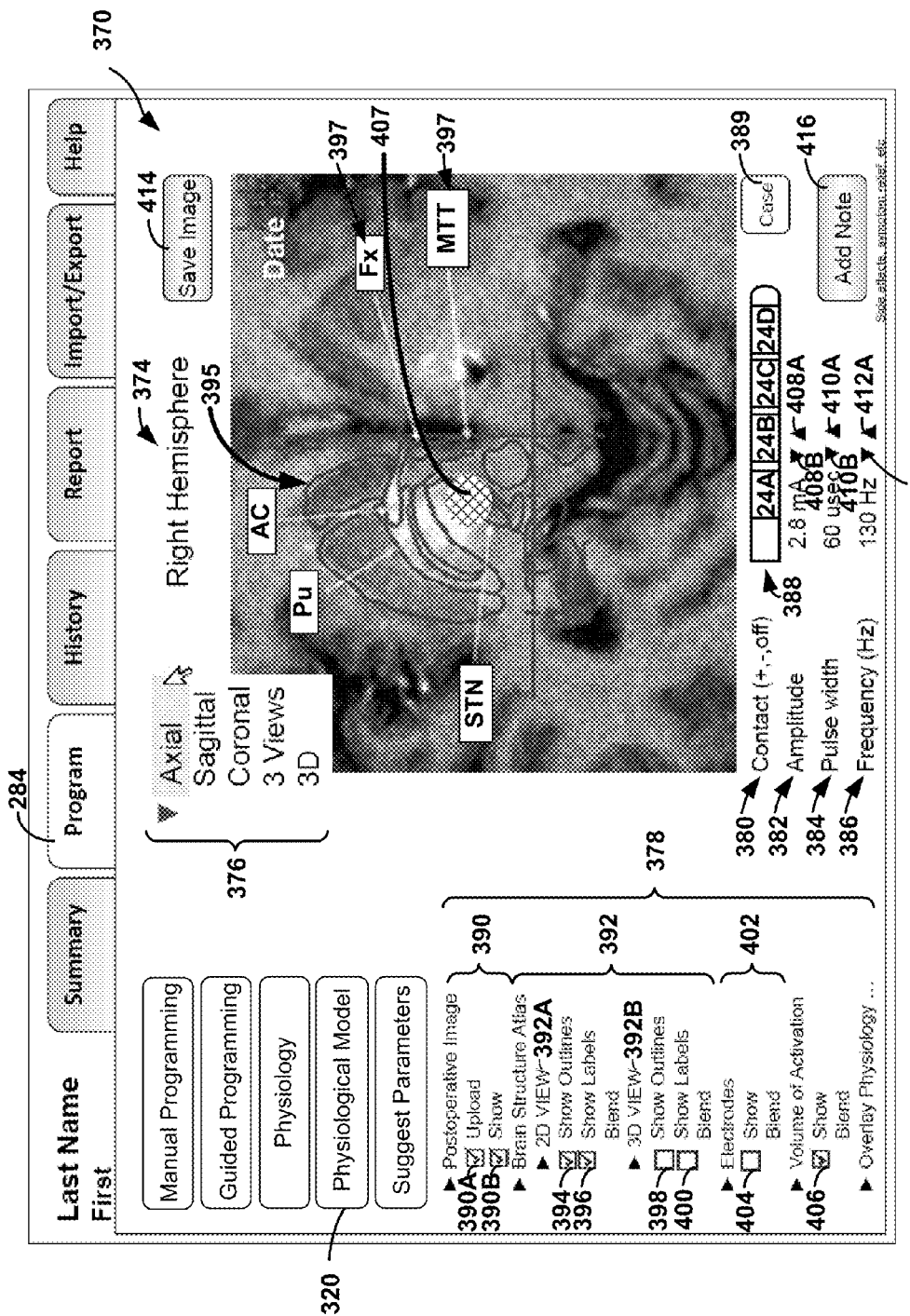

As shown in FIG. 19F, processor 80 of programmer 14 also may also present GUI 370 with which a user may interact to select one or more stimulation electrodes with which IMD 16 delivers stimulation to patient 12 based on a physiological model of tissue of patient 12 proximate implanted leads 20. As described with respect to FIGS. 8 and 9, processor 80 can select one or more stimulation electrode combinations based on the sensed bioelectrical brain signal, e.g., based on the patient data generated using GUI 330 shown in FIG. 19E and confirm the electrode combination selection based on a physiological model, e.g., the physiological model displayed by GUI 370, or processor 80 can select the one or more stimulation electrode combinations based on a physiological model, e.g., patient data generated using GUI 370, and confirm the electrode combination selection based on a bioelectrical brain signal. The user may view GUI 370 before or after ranking electrodes 24 based on the proximity of electrodes to a target tissue site, e.g., as described with respect to GUI 330 shown in FIG. 19E.

Processor 80 may display GUI 370 upon receiving user input selecting physiological model button 320. Physiological model button 320 provides a user with the option to select one or more stimulation electrodes with which IMD 16 delivers stimulation to patient 12 based on a physiological model that indicates a characteristic of tissue of patient 12 proximate the implanted electrodes. As discussed above with respect to FIG. 18, programmer 14 can generate and display a physiological model that helps a clinician visualize lead location, one or more anatomical structures, and/or therapy fields (e.g., volume of tissue activated). GUI 370 is another example of a graphical user interface that displays a physiological model.

GUI 370 includes graphical representation of tissue 372 of patient 12 proximate implanted electrodes 24, indicator 374 that indicates the hemisphere of brain 28 illustrated by graphical representation of tissue 372, menus 376, 378 for controlling the detail of tissue illustrated by graphical representation of tissue 372, and various user interface mechanisms with which the user can interact to modify one or more stimulation parameter values. In the example shown in FIG. 19F, GUI 370 includes electrode selection control 380, amplitude control 382, pulse width control 384, frequency control 386, graphical representation of lead 388, and graphical representation of case electrode 389. Graphical representation of lead 388 includes a graphical representation of electrodes 24. In some examples, such as examples in which therapy system 10 does not include a case electrode, GUI 370 may not include a graphical representation of case electrode 389 or the case electrode 389 may be included in GUI 370, but as a non-selectable object, such that the user cannot select case electrode 389 as a stimulation electrode.

In the example shown in FIG. 19F, graphical representation of tissue 372 illustrates a graphical representation of tissue within brain 28 of patient 12 because leads 20 are implanted within brain 28. In addition, in the example shown in FIG. 19F, an image of tissue of brain 28 is illustrated, and, in particular, an axial view of brain 28. In other examples, other types of graphical representations can be included in GUI 370, such as a schematic representation (e.g., a computer-aided rendering) of at least a portion of brain 28 or images or schematic representation of tissue at regions of patient 12 other than brain 28. Because a portion of brain 28 is illustrated in FIG. 19F and patient 12 includes two leads 20 implanted within brain 28, indicator 374 indicates the hemisphere for brain 28 illustrated by GUI 370. In other examples, however, such as examples in which leads are implanted in another region of tissue, indicator 374 can provide a different region (e.g., the side of the midline illustrated by GUI 370). In addition, in some examples, GUI 370 may not include indicator 374.

In the example shown in FIG. 19F, tissue proximate to lead 20A, which is implanted in right hemisphere of brain 28, is illustrated. In examples in which a therapy system includes multiple leads, processor 80 can generate and display separate GUIs similar to GUI 370 for each of the implanted leads, and/or a single GUI that illustrates tissue proximate to multiple leads. For example, with respect to therapy system 10, processor 80 can also generate and display a GUI similar to GUI 370 with which a user can interact to select one or more electrodes 26 of lead 20B as stimulation electrodes based on a physiological model. Thus, the description of GUI 370 may also be applicable to a description of a GUI that illustrates tissue proximate lead 20B.

Leads 20 are implanted within a volume of brain 28. Thus, if processor 80 presents a 2D view of brain 28, as shown in FIG. 19F, the tissue at only one depth of the brain 28 or the representation of tissue as viewed from one angle may be illustrated. In the example shown in FIG. 19F, GUI 370 includes options with which the user can select the view of brain 28 illustrated by the displayed graphical representation of tissue 372. The user can interact with menu 376 to select the view of tissue of brain 28 that illustrated by graphical representation of tissue 372. In one example, as shown in FIG. 19F, menu 376 is a pull-down menu that provides options with which the user can view an axial view of tissue proximate implanted electrodes 24 of lead 20A (which is implanted in the right hemisphere of brain 28 as illustrated in FIG. 1), a sagittal view, a coronal view, all three of the axial, sagittal, and coronal views, and a 3D view of tissue of brain 28 proximate electrodes 24. An axial view may be a view of brain 28 of patient 12 from a perspective looking towards the central axis of brain 28. A coronal view may be a front-back vertical section of brain 28. A sagittal view of brain 28 may be taken from a perspective substantially perpendicular to the coronal view or the axial view.

In response to receiving user input selecting a view from menu 376, processor 80 can update graphical representation of tissue 372 shown in GUI 370 to include the selected view of tissue of brain 28 proximate leads 20. In some examples, the different images or other digital representations of brain 28 (e.g., computer renderings) can be stored as part of physiological model data 92 (FIG. 4) of memory 82 of programmer 14. Instead of or in addition to storing the different graphical representations of tissue locally within programmer 14, the images and other physiological model data 92 can be stored in a remote database. Menu 378 includes sub-menu 390, which provides a user with to upload a post-operative image of brain 28 (e.g., after leads 20 are implanted) and update GUI 370 to include the post-operative image. Menu 390 includes upload box 390A and show box 392A that the user can select (e.g., by clicking within the box with a peripheral pointing device) in order to initiate the post-operative image uploading by processor 14 and the updating of GUI 370 to include the post-operative image, respectively. The post-operative image of brain 28 can be stored by memory 82 (FIG. 4) of programmer 14 or a memory of another device (e.g., a remote database). The options provided by menu 390 may be selected by a user when the user initially interacts with physiological model button 320 of programmer 14, e.g., in order to generate the relevant graphical representation of tissue 372 displayed by GUI 370.

The user can also control the type of information displayed by graphical representation of tissue 372 by interacting with menu 378 of GUI 370. For example, processor 80 of programmer 14 can aid the user's understanding of graphical representation of tissue 372 illustrated by GUI 370 by, for example, highlighting (e.g., labeling, color coding or outlining) one or more anatomical structures of brain 28 illustrated by graphical representation of tissue 372. In the examples shown in FIG. 19F, menu 378 of GUI 370 includes sub-menu 392 for selecting the view of brain structure processor 80 includes within graphical representation of tissue 372. Menu 392 includes 2D view 392A and 3D view 392B, which, in the example shown in FIG. 19F, are each selection boxes that can be selected by a user, e.g., by clicking within the box with a peripheral pointing device. Upon receiving user input selecting 2D view 392A, processor 80 can control user interface 84 to display a 2D graphical representation of tissue 372 of brain 28 proximate implanted electrodes 24. In addition, upon receiving user input selecting 3D view 392B, processor 80 can control user interface 84 to display a 3D graphical representation of tissue 372 of brain 28 proximate implanted electrodes 24. In some examples, programmer 14 may be configured such that only one of the 2D view or the 3D view of brain 28 can be displayed at a time. In other examples, programmer 14 may be configured such that both the 2D view and the 3D view of brain 28 can be displayed simultaneously (e.g., within different sub-windows) within GUI 370.

GUI 370 also includes options that the user can select upon selecting 2D view 392A and 3D view 392B. In particular, if the user selects 2D view 392A, the user can select "show outlines" 394 box in order to view outlines of the anatomical brain structures of brain 28 and "show labels" box 396 in order to view textual labels of the anatomical structures of brain 28 within graphical representation of tissue 372. In response to receiving user input selecting "show outlines" box 394, processor 80 can access information stored by memory 82 of programmer 14 or a remote database to add outlines 395 to graphical representation of tissue 372 shown in GUI 370. In the example shown in FIG. 19F, each outline 395 may be defined by a line that is drawn around the anatomical structures shown in the image. In some examples, outlines 395 of the anatomical structures may be predetermined, such that processor 80 can access the predetermined outlines and overlay the outlines over graphical representation of tissue 372.

Processor 80 can generate outlines 395 of the anatomical structures of brain 28 using any suitable technique, such as template matching or based on the coordinates of the tissue included in graphical representation of tissue 372. For example, processor 80 can access templates that have predetermined shapes (which can be 2D or 3D) and implement an algorithm that finds a best fit between the templates the regions of tissue included in graphical representation of tissue 372. The algorithm can indicate the percentage match between a template shape (2D or 3D) and the regions of tissue indicated by the different densities of tissue of brain 28 or other tissue characteristics that can be identified from an image or other graphical representation of brain 28.

As another example, processor 80 can generate outlines 395 of the anatomical structures of brain 28 shown in graphical representation of tissue 372 by determining the coordinates of electrodes 24 and/or lead 20A, and mapping the coordinates to an atlas of brain 28 that indicates the anatomical structures of brain 28 and their relative coordinates. Based on the information that indicates the anatomical structure of brain 28 proximate the electrodes 24 and/or lead 20A itself, processor 80 can place lines around the anatomical structures shown in graphical representation of tissue 372 to generate outlines 395 by distinguishing between anatomical structures based on the density of tissue or other tissue characteristics that can be identified from an image or other graphical representation of brain 28 or by mapping the anatomical structures to anatomical landmarks displayed by graphical representation of tissue 372. Processor 80 can, for example, overlay an anatomical atlas over an image (e.g., an MRI) of a portion of brain 28 and automatically, or with the aid of a user, adjust (e.g., stretch or shrink) the atlas to fit over the region of brain 28 shown in the image; the atlas, once sized and positioned over the image, may then indicate the structures shown in the image.

In other examples, rather than positioning outlines 395 within graphical representation of tissue 372, processor 80 may color code the anatomical structures shown in graphical representation of tissue 372 or provide another mechanism for visually distinguishing between the anatomical structures.

Upon receiving user input selecting "show labels" box 396, processor 80 can update graphical representation of tissue 372 to include labels 397 of the anatomical structures within GUI 370. Labels 397 may be alphanumeric indications of one or more of the anatomical structures shown in graphical representation of tissue 372 (e.g., an abbreviation or the full name). In the example shown in FIG. 19F, labels 397 indicate the subthalamic nucleus (STN), the medial border of the putamen (Pu), the anterior commissure (AC), the anterior column of the formix (Fx), and the mamillothalamic tract (MTT). Also shown by graphical representation of tissue 372 but not labeled include the red nucleus, internal capsule, globus pallidus internus, and globus pallidus externus.

Processor 80 can implement techniques similar to those used to access or provide the outlines of the anatomical structures in order to place anatomical structure labels 397 in graphical representation of tissue 372. For example, processor 80 can access data that associates labels 397 with the graphical representation of tissue 372 shown in GUI 370. As another example, processor 80 can generate labels 397 by template matching to determine the anatomical structures shown by the graphical representation of tissue 372 or determining the anatomical structures based on the coordinates of the anatomical structures and lead 20A and/or electrodes 24.

GUI 370 also includes options for including outlines 395 and/or labels 397 of anatomical structures within the 3D view (not shown in FIG. 19F) of graphical representation of tissue 372. Upon receiving user input selecting 3D view 392b and "show outlines" box 398, processor 80 can update graphical representation of tissue 372 to include a 3D view of tissue of brain 28 in addition to outlines of one or more anatomical structures of brain 28. Processor 80 can implement any suitable technique, such as the ones described above with respect to "show outlines" box 394 for generating outlines of respective anatomical structures within a 2D view. However, rather than generating a 2D outline, processor 80 outlines a 3D illustration of the anatomical structure. In either the 2D or 3D example, an entire anatomical structure may not be displayed within the portion of tissue shown in graphical representation of tissue 372. Thus, the outline may only be partial or may only outline a portion of the anatomical structure actually shown by graphical representation of tissue 372.

Similarly, upon receiving user input selecting 3D view 392b and "show labels" box 400, processor 80 can update graphical representation of tissue 372 to include a 3D view of tissue of brain 28 in addition to labels of one or more anatomical structures of brain 28. Processor 80 can implement any suitable technique, such as the ones described above with respect to "show labels" box 396 for generating outlines of anatomical structures within a 2D view.

In the example shown in FIG. 19F, menu 378 with which the user can interact to select the information illustrated by graphical representation of tissue 372 also includes menu 402, which provide a user with the option to view electrodes 24 implanted within brain 28. Upon receiving user input selecting "show" box 404 under the electrodes menu 402, processor 80 can update graphical representation of tissue 372 to include graphical representations of one or more electrodes and, in some examples, lead 20A. The graphical representation of electrodes can be an image of the actual electrodes 24 or similar electrodes, a computer-generated rendering of electrodes 24 implanted within patient 12 or any other suitable graphical representation.

The graphical representations of electrodes illustrated by GUI 370 can be similar to lead icon 254 described above with respect to FIG. 18. As with lead icon 254, the graphical representation of the electrodes presented by GUI 370 can include the same positioning of electrodes 24 relative to tissue of brain 28, the same relative spacing as the electrodes of the lead implanted within patient 12, and a similar scale as the implanted electrodes 24 relative to brain 28. In this way, GUI 370 displays a physiological information with which the user can relatively quickly ascertain the location of electrodes 24 relative to tissue of brain 28 and determine which electrodes 24 are proximate the target anatomical structures for the stimulation and the anatomical structures to avoid.

In examples in which graphical representation of tissue 372 includes an actual image of brain 28 of patient 12, processor 80 can position the graphical representations of electrodes 24 (not shown in FIG. 19F) relative to graphical representation of tissue 372 based on patient-specific information. For example, processor 80 may access a preoperative MRI of brain 28 (e.g., before leads 20 are implanted), and morph brain structure volumes to the patient MRI in order to generate a 3D representation of at least a portion of brain 28, which can be useful for generating graphical representations of different "slices" of brain 28 if 2D view 392A is selected. Processor 80 can then access a post-operative MRI of brain 28 in order to determine the location of leads 20. Processor 80 can merge the pre-operative and post-operative MRI images, and locate the image of the lead relative to brain structure volumes in order to determine where to position the graphical representation of electrodes relative to graphical representation of tissue 372.

As discussed above, in some examples, a physiological model includes a therapy field model that indicates the therapy field that may result from IMD 16 delivering stimulation to patient 12 via the selected stimulation electrode combination and other selected stimulation parameter values. Menu 378 includes an option that the user can select to view a therapy field model of therapy delivered by IMD 16 according to particular set of electrodes and other therapy parameter values. In the example shown in FIG. 19F, the therapy field model includes an activation field, which indicates the neurons that will be activated by the electrical field in the patient anatomical region covered by the stimulation therapy. Menu 378 includes show box 406 for controlling the display of a graphical representation of activation field 407 within GUI 370. Upon receiving user input selecting show box 406, processor 80 can generate and display a graphical representation of activation field 407 over graphical representation of tissue 372 using the techniques described above with respect to FIGS. 7 and 18.

Graphical representation of activation field 407 indicates the neurons that will be activated by the electrical field in the patient anatomical region covered by the stimulation therapy. As with therapy field 256 shown in FIG. 18, graphical representation of activation field 407 displayed by GUI 370 may help the user visualize how therapy delivered by IMD 16 according to a specific set of stimulation electrodes and stimulation parameter values may affect tissue of brain 28. In combination with graphical representation of tissue 372, and, in some examples, outlines 395 and labels 397 of anatomical structures, the user can relatively quickly ascertain, based on graphical representation of activation field 407, whether the selected stimulation electrodes and stimulation parameter values are useful for stimulating the target tissue site (e.g., specific anatomical structures or portions of anatomical structures) or avoiding stimulation of tissue sites associated with stimulation-induced side effects.

Processor 80 may generate graphical representation of activation field 407 based on characteristics of tissue proximate electrodes 24 as well as stimulation electrodes selected via electrode selection control 380 and stimulation parameter values selected by the user via electrode selection control 380, amplitude control 382, pulse width control 384, and frequency control 386. Electrode selection control 380 includes graphical representation of lead 389, which includes a graphical representation of respective electrodes 24, and, if therapy system includes a housing electrode (also referred to as a case electrode), graphical representation of the case electrode 389. The user can select one or more stimulation electrodes from the depicted electrodes 24 and case electrode 389 and assign a polarity to the selected electrodes using any suitable technique.

In one example, electrodes 24 are selectable objects and the user can move a cursor within GUI 370 over the desired electrode 24 or 389 and providing a positive indication of input (e.g., single or double clicking a button on a mouse or by depressing the screen on which GUI 370 is displayed if programmer 14 includes a touch screen) to select the electrode. A first click or another positive indication can assign a first polarity (e.g., a positive polarity) to the electrode and a second, subsequent click or other positive indication can assign a second polarity (e.g., a negative polarity) to the electrode. In another example, electrodes 24 may not be displayed as selectable objects within GUI 370 and a user can select an electrode by moving a polarity symbol (e.g., a positive (+) symbol or a negative (−) symbol) over a displayed electrode 24 or case electrode 389. Other techniques for selecting electrodes 24 and assigning polarities to the selected electrodes are contemplated. Regardless of the specific technique with which processor 80 receives user input selecting an electrode 24, 389, GUI 370 presented by processor 80 provides GUI 370 with which the user can interact to select an electrode and view the corresponding therapy field that may result from delivery of stimulation by IMD 16 via the selected electrodes and a set of stimulation parameter values that define the stimulation signal.

In the example shown in FIG. 19F, GUI 370 enables a user to modify the amplitude, pulse width, and frequency of the stimulation signal. In other examples, GUI 370 can include controls with which the user can modify other stimulation parameter values (e.g., duty cycle) in addition to or instead of amplitude, pulse width, and frequency.

In the example shown in FIG. 19F, amplitude control 382, pulse width control 384, and frequency control 386 are each associated with up arrows 408A, 410A, 412A, respectively, and down arrows 408B, 410B, 412B, which are displayed as selectable objects within GUI 370. The user can increase or decrease the respective stimulation parameter value by selecting the respective arrow 408A, 408B, 410A, 410B, 412A, 412B, e.g., by moving a cursor within GUI 370 over the desired arrow and providing a positive indication of input (e.g., single or double clicking a button on a mouse or by depressing the screen on which GUI 370 is displayed if programmer 14 includes a touch screen). As the user modifies the stimulation parameter value, processor 80 may update GUI 370 to display the current value of the stimulation parameter value, as shown in FIG. 19F.

In some examples, upon receiving user input selecting up arrow 408A associated with stimulation amplitude control 382, processor 80 may increase the stimulation amplitude with which stimulation generator 44 (FIG. 2) of IMD 16 generates stimulation signals delivered to patient 12 by a predetermined increment (e.g., 0.5 milliamps). Similarly, upon receiving user input selecting down arrow 408B, processor 80 may decrease the stimulation amplitude by a predetermined increment. Processor 80 may modify the pulse width of a stimulation signal generated and delivered by IMD 16 in a similar manner upon receiving user input selecting arrows 410A, 410B, and modify the frequency of a stimulation signal generated and delivered by IMD 16 in a similar manner upon receiving user input selecting arrows 412A, 412B.

In order to generate activation field, processor 80 determines how an electrical field propagates away from an origin location with the set of stimulation parameter values selected by amplitude control 382, pulse width control 384, and frequency control 386, and electrodes 24 selected by electrode selection control 380. Processor 80 inputs the stimulation parameter values selected via amplitude control 382, pulse width control 384, and frequency control 386 into the electrical field model equation (or other therapy field model equation), and, together with the physical tissue characteristics (e.g., tissue conductivity or tissue impedance values) of the tissue adjacent electrodes 24, generates an estimated electrical field that will produced when IMD 16 delivers therapy to patient 12. Upon determining the electrical field, processor 80 can determine the activation field using an activation field model equation that defines how a neuron model fits to the electrical field model. As discussed with respect to FIG. 7, the neuron model may be a set of equations, a lookup table, or another type of model that defines threshold action potentials of particular neurons that make up the anatomical structure, as defined by the patient anatomy data, affected by the electrical field determined based on the electrical field model equation.

In the example shown in FIG. 19F, GUI 370 also includes save button 414 that the user can select to save the image displayed by GUI 370 (which may or may not be an actual image of patient tissue). The image displayed by GUI 370 may include graphical representation of tissue 372, and, if displayed, outlines 395, labels 397, and graphical representation of activation field 407 (or another therapy field model). Upon receiving user input selecting save button 414, processor 80 may save the image displayed by GUI 370 as part of physiological model data 92 within memory 82 (FIG. 4) of programmer 14. The user may then retrieve the stored image from memory 82 for later analysis.

GUI 370 also includes add notes button 416. Upon selection of add notes button 416, processor 80 may open up a window within GUI 370 or a separate GUI and the user may enter information via the window, such as notes regarding the user's observations about the selected electrodes and stimulation parameter values or questions to investigate at a later time. The user may input information using any suitable technique, such as by inputting text from a keyboard or keypad of user interface 84 of programmer 14 or by speaking into a microphone. Processor 80 can save the text, audio information or other format of notes in memory 82 and, in some examples, associate the notes with the image displayed by GUI 370, and an indication of the selected electrodes and stimulation parameter values.

Figure 19G:
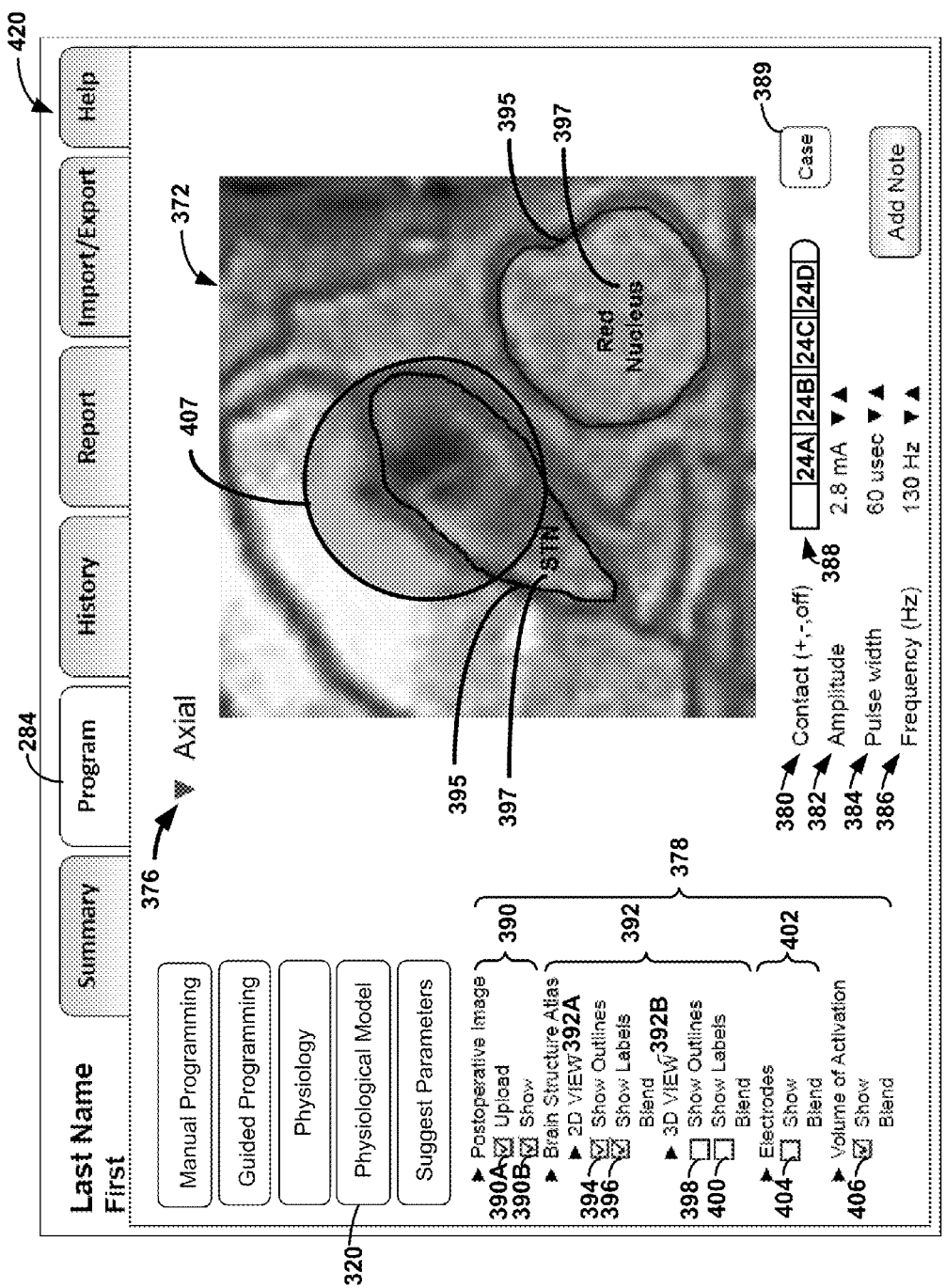

FIG. 19G illustrates GUI 420, which is similar to GUI 370 (FIG. 19F), but includes a closer, axial view of graphical representation of tissue 372 (e.g., an axial orientation of a slice of brain 28). Processor 80 may generate and display GUI 420 upon receiving user input selecting an axial view from menu 376. GUI 420 also includes outlines 395 of anatomical structures shown in graphical representation of tissue 372, labels 397 of the anatomical structures, and graphical representation of activation field 407. In the example shown in FIG. 19G, outlines 395 outline the subthalamic nucleus (STN) and red nucleus of brain 28, and labels 397 provide textual indications of the same.

Figure 19H:
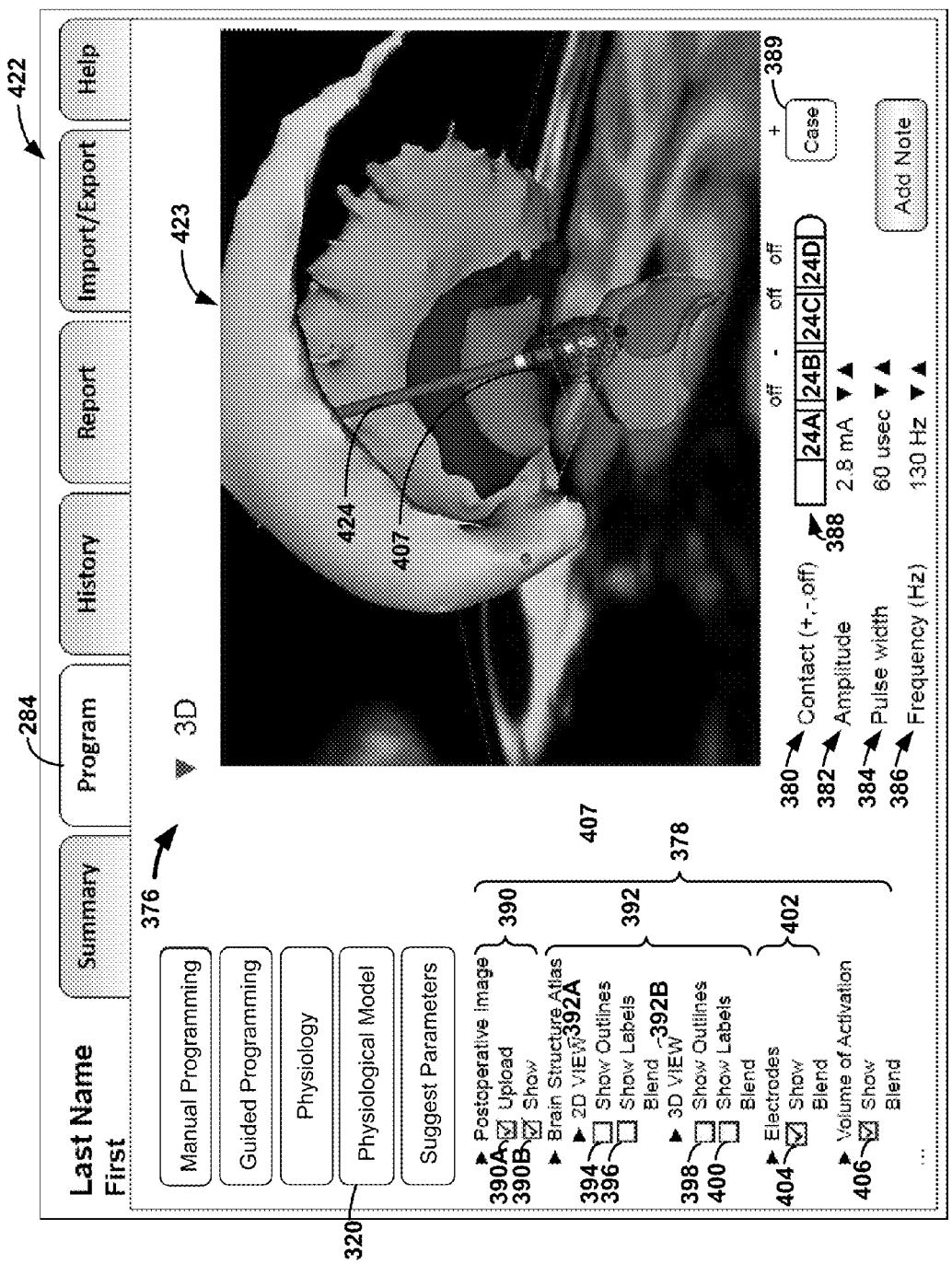

FIG. 19H is a screen diagram illustrating an example GUI 420 displayed by programmer 14, where GUI 420 presents a physiological model to a user. GUI 422 is similar to GUI 370 (FIG. 19F), but includes a 3D view of graphical representation of tissue 423 instead of 2D view of graphical representation of tissue 372. Processor 80 may generate and display GUI 422 upon receiving user input selecting a 3D view from menu 376. Graphical representation of tissue 423 shown in FIG. 19H includes a 3D perspective view of tissue of brain 28 of patient proximate implanted electrodes 24 and lead 20A. Processor 80 can generate GUI 422 to include a 3D view of tissue 423 of brain 28 using any suitable technique. In some examples, processor 80 generates 3D view of graphical representation of tissue 423 based on a 3D medical image (e.g., MRI, CT, or another medical imaging modality) of brain 28 of patient 12.

Instead of or in addition to an image of brain 28, processor 80 may generate 3D view of graphical representation of tissue 423 based on an image of a brain of a patient other than patient 12, or based on a computer rendering of brain 28 of patient 12 or a more general brain not specific to patient, or using any other technique. 3D view of graphical representation of tissue 423 may be displayed on a 2D display of programmer 14 by using partially transparent surfaces and grey or color shades. In the example shown in FIG. 19H, 3D view of graphical representation of tissue 423 is shaded to visibly distinguish between different anatomical structures of brain 28.

In the example shown in FIG. 19H, GUI 420 also includes graphical representation of lead 424, which may be similar to lead icon 254 shown in GUI 250 (FIG. 18). Thus, in some examples, graphical representation of lead 424 may be a schematic illustration of lead 20A or an image of the actual lead 20A implanted within patient 12. Lead 424 is illustrated as a 3D object within GUI 420. Graphical representation of lead 424 includes graphical representations of electrodes, which may correspond to electrodes 24 of lead 20A. Processor 80 can position examples, graphical representation of lead 424 within graphical representation of tissue 372 after receiving user input selecting show electrodes box 404 under electrodes 402 option of menu 378.

As with lead icon 254 in GUI 250, processor 80 may position graphical representation of lead 424 relative to graphical representation of tissue 423 to represent the actual implant location and orientation of lead 20A within brain 28. In other examples, the user may manually place graphical representation of lead 424 within 3D graphical representation of tissue 423 based upon stereotactic data or implant coordinates for the actual lead 20A implanted within patient 12. With the aid of GUI 422, the user can relatively quickly ascertain the location and orientation of lead 20A within brain 28, and the anatomical structures proximate the implanted lead 20A.

GUI 420 also includes graphical representation of activation field 407, which illustrates the activation field that may result when IMD 16 delivers therapy to patient 12 via a specific set of stimulation electrodes and stimulation parameter values. In some examples, the user may select the select the stimulation electrodes and stimulation parameter values via electrode selection control 380, amplitude control 382, pulse width control 384, and frequency control 386. In the example shown in FIG. 19H, activation field 407 is illustrated as a 3D object, and has a size and shape that corresponds to the volume of tissue that processor 80 has determined may be activated by stimulation delivery by IMD 16 via the specific set of stimulation electrodes and stimulation parameter values.

In some examples of GUI 422, the user may rotate graphical representation of tissue 423 in one or more directions (e.g., about a dorsal-ventral axis, about an anterior-posterior axis, about another predefined axis or in all six degrees of freedom). For example, the user may input angles of rotation using a keyboard or keypad of user interface 84 (FIG. 4) of programmer 14, or the user may interact directly with graphical representation of tissue 423 (e.g., moving a cursor within graphical representation of tissue 423) to rotate the displayed graphical representation of tissue 423. In response to receiving user input rotating graphical representation of tissue 423, processor 80 may also rotate the graphical representation of lead 424 and activation field 407.

In accordance with some techniques described herein, processor 80, alone or with the aid of a user, may select one or more stimulation electrodes 24, 26 (FIG. 1) with which IMD 16 delivers stimulation therapy to brain 28 of patient 12 based on data from one or more bioelectrical brain signals sensed via different electrodes 24, 26 or combinations of electrodes 24, 26, and a physiological model that indicates one or more characteristics of tissue proximate the electrodes 24, 26 within brain 28 of patient 12. GUIs 330, 370, 420, 422 described with respect to FIGS. 19E, 19F, 19G, and 19H, respectively, illustrate example diagrams of user interfaces that processor 80 of programmer 14 may present via user interface 84 to aid a user in the programming of one or more stimulation electrodes. For example, the user can initiate the sensing of bioelectrical brain signals with the aid of GUI 330 (FIG. 19E) or review a physiological model with the aid of GUI 370, 420, 422 in order to, e.g., confirm a stimulation electrode selection or select one or more stimulation electrodes.

GUI 330 shown in FIG. 19E illustrates a ranking of electrodes 24 based on one or more characteristics of bioelectrical brain signals sensed via electrodes 24. As described above, in some examples, processor 80 automatically ranks electrodes 24 based on a proximity to a target tissue site, which may be indicated by a signal characteristic (e.g., a power level within a particular frequency band) of a bioelectrical brain signal sensed via a respective electrode in a unipolar configuration or sensed via a respective electrode in combination with another electrode 24 in a bipolar configuration. GUIs 370, 420, 422 shown in FIGS. 19F, 19G, and 19H, respectively, illustrate different physiological models, based on which the user can visualize the proximity of electrodes 24 to a target tissue site or a tissue site associated with one more stimulation-induced side effects, and, in some examples, the proximity of a model of a therapy field (e.g., an activation field as shown in FIGS. 19G and 19H), to the target tissue site or the tissue site associated with one more stimulation-induced side effects.

Figure 19I:
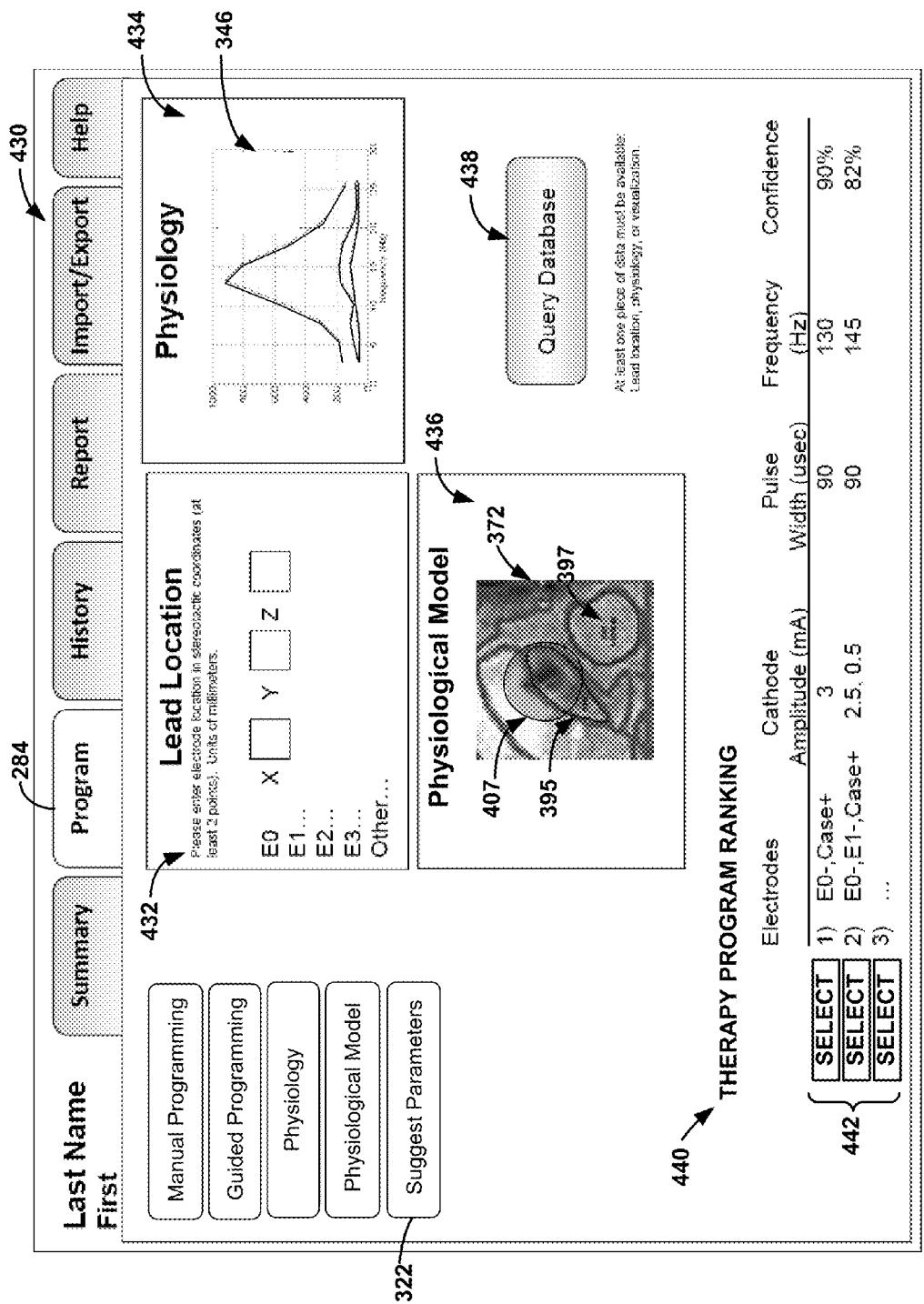

After processor 80 automatically ranks electrodes 24 based on one or more characteristics of bioelectrical brain signals sensed via electrodes 24 or a user provides input ranking electrodes 24, processor can display a summary screen 430 (also referred to as GUI 430), as shown in FIG. 19I, which may suggest stimulation electrodes, and, in some examples, stimulation parameter values that may provide efficacious therapy to patient 12 (e.g., therapy delivery that provides therapeutic benefits and minimizes side effects). Summary screen 430 may be presented by processor 80 via a display of user interface 84 (FIG. 4) of programmer 14 before or after the user visualizes the physiological model that indicates whether electrodes 24 and/or a therapy field resulting from stimulation delivery via specific subset of electrodes 24 are proximate a target tissue site or a tissue site associated with one or more stimulation-induced side effects.

Summary screen 430 includes lead location window 432, physiology window 434, and physiological model window 436. Lead location window 432 summarizes the location of electrodes 24 of lead 20A within brain 28 (as well as electrodes 26 in some examples). In the example shown in FIG. 19I, window 432 indicates the location of electrodes 24 via stereotactic coordinates, although other 3D coordinates may also be used in other examples. The coordinates may be the actual coordinates used to implant lead 20A within brain 28 or the coordinates determined post-implant, e.g., based on one or more medical images of brain 28 and implanted lead 20A. The user can view the location of each electrode 24 illustrated in window 432 and modify the coordinates, if necessary.

Physiology window 434 summarizes the results of the bioelectrical brain signal sensing via the implanted electrodes 24. In the example shown in FIG. 19I, physiology window 434 displays graph 346, which illustrates the distribution of power within one or more frequency bands for a plurality of bioelectrical brain signals sensed via different subsets of electrodes 24. In other example, physiology window 434 may summarize the results of the bioelectrical brain signal sensing via the implanted electrodes 24 by displaying other types of data (e.g., graph 348 shown in FIG. 19E or representation of lead 344 that ranks electrodes 24, as shown in FIG. 19E) in addition to or instead of graph 346.

In some examples, physiology window 434 is a selectable object. Upon receiving user input selecting window 434 (e.g., using the techniques described above with respect to selecting an object within a GUI displayed by programmer 14), processor 80 of programmer 14 may display GUI 330 (FIG. 19E) or another GUI 330 with which the user can control the sensing of the bioelectrical brain signals via electrodes 24. A user may revert to GUI 330 for many reasons, such as if the user determines that the frequency band characteristics extracted from the sensed bioelectrical brain signals were not useful to distinguish between the location of electrodes 24 relative to different regions of brain 28 of patient 12. The user may rerun the bioelectrical brain signal sensing by interacting with GUI 330, e.g., as described above with respect to FIG. 19E.

Physiological model window 436 provides a snapshot of graphical representation of tissue 372 proximate implanted electrodes 24, which may help a user visualize the target tissue site for stimulation therapy and/or the tissue site associated with a stimulation-induced side effect. The graphical representation of tissue 372 can be, for example, an image (e.g., screen shot) of at least a portion of GUI 330 (FIG. 19E) saved by processor 80 within memory 82, e.g., upon receiving user input selecting save image button 414 (shown in FIG. 19F). In some examples, as shown in FIG. 19I, graphical representation of tissue 372 displayed within physiological model window 436 can include activation field model 407 (or another type of therapy field model), outlines 395 of anatomical structures and labels 397 of the anatomical structures, which are described above with respect to FIGS. 19F and 19G. In other examples, physiological model window 436 can include a 3D view of tissue proximate electrodes 24 within brain 28 of patient 12, multiple views of tissue proximate implanted electrodes 24, a graphical representation of lead 426 (FIG. 19H), and/or another therapy field model.

In some examples, physiological model window 436 is a selectable object. Upon receiving user input selecting window 436 (e.g., using the techniques described above with respect to selecting an object within a GUI displayed by programmer 14), processor 80 of programmer 14 may display one or more GUIs 370, 420, 422 or another GUI with which the user can visualize a physiological model that indicates one or more characteristics of tissue proximate implanted electrodes 24. A user may revert to one or more of GUIs 370, 420, 422 for many reasons, such as if the user determines that a therapy field model displayed in physiological model window 436 indicates the selected electrodes and/or stimulation parameter values do not overlap with a target tissue site and/or overlap with a tissue site associated with a stimulation-induced side effect. The user may adjust the stimulation electrode selection using electrode selection control 380 (FIG. 19F) or adjust one or more stimulation parameter values using amplitude control 382, pulse width control 384, and/or frequency control 386 (FIG. 19F) until a desirable therapy field model is achieved. Processor 80 can update the size, shape, and/or location of activation field 407 displayed by GUI 370, 420, and/or 422 as the user adjusts the stimulation electrode selection and/or stimulation parameter values.

GUI 430 also includes query database button 438, which the user may select in order to retrieve additional information from memory 82 of programmer 14 or a memory of another device (e.g., a remote database). The user may select query database button 438 if, for example, one or more of lead location window 432, physiology window 434 or physiological model window 436 are not displayed within GUI 430. Upon receiving user input selecting query database button 438, processor 80 may control user interface 84 of programmer 14 to display a window that indicates different types of information stored by memory 82 or another memory, and the user may select a type of information for display within summary screen 430. Processor 80 can update GUI 430 to include the user-selected type of information (e.g., electrode location, information about bioelectrical brain signals sensed via electrodes 24 or a graphical representation of tissue proximate implanted electrodes 24). The database may also contain information relating lead location (e.g., stereotactic coordinates of electrodes, lead location generated from physiological model) to side effects, clinical effects, and stimulation parameters. This type of information may help the user identify which electrodes and stimulation parameters to start out with to generate a therapy program.

GUI 430 includes list 440 that ranks therapy programs, which each define a stimulation electrode combination (e.g., a combination of one or more electrodes 24 of lead 20A and, in some examples, an electrode on an outer housing of IMD 16, and respective polarities of the electrodes) and one or more stimulation parameter values (e.g., values for a current amplitude, pulse width, and frequency) that define the stimulation signal generated by stimulation generator 46 (FIG. 2) of IMD 16. Processor 80 can automatically order different therapy programs in some examples, while in other examples, the user may provide input ordering the therapy programs and processor 80 can update GUI 430 to reflect the order of therapy programs provided by the user.

In examples in which processor 80 automatically orders therapy programs, processor 80 may order the therapy programs based on the bioelectrical brain signals sensed via the electrodes of the respective therapy program and/or a physiological model that may indicate the tissue proximate the implanted electrodes. In some examples, processor 80 orders therapy programs based on the proximity of the electrodes of the electrode combination of the therapy program to the target tissue site, which can be based on the bioelectrical brain signal characteristic alone, the physiological model alone, or both (e.g., as described with respect to FIGS. 8 and 9).

For example, processor 80 may order the therapy programs in order of the power level within a beta band of a bioelectrical brain signal sensed via the electrodes of the electrode combination of the therapy program, the highest beta band power level indicating the closest proximity to the target tissue site. If the electrode combination includes multiple sub-electrode combinations, such that multiple bioelectrical brain signals are associated with the therapy program, processor 80 can rank the therapy programs based on a mean, median, peak or lowest the beta band power level of each of the bioelectrical brain signals sensed via each of the sub-electrode combinations. As an example of how a therapy program may be associated with multiple bioelectrical brain signals, therapy program that includes an electrode combination including electrodes 24A, 24B, and 24C be associated with three bioelectrical brain signals sensed via electrodes 24A, 24B, and 24C in a unipolar configuration or three bioelectrical brain signals sensed via electrodes 24A-24B in a bipolar configuration, electrodes 24B-24C in a bipolar configuration, and electrodes 24A-24C in a bipolar configuration.

As another example of a technique processor 80 can implement to order therapy programs, processor 80 may order the therapy programs based on a proximity of electrodes of the therapy program to a target tissue site, which can be determined based on the physiological model that maps the electrodes 24 to tissue of brain 28. In one example, processor 80 approximates a distance between the electrodes of a therapy program to the target tissue site using a predetermined scale, and orders a plurality of therapy programs based on the mean, median, maximum or minimum distance of the electrodes of a therapy program to the target tissue site. The therapy program with the electrodes closest to the target tissue site (as indicated by the mean, median, maximum or minimum distance of the electrodes of the electrode combination relative to the target tissue site) may have the highest ranking. Similarly, in some examples, processor 80 may order the therapy programs based on a proximity of electrodes of the therapy program to a tissue site associated with one or more stimulation-induced side effects. The therapy program with the electrodes furthest from the tissue site associated with the stimulation-induced side effects (as indicated by the mean, median, maximum or minimum distance of the electrodes of the electrode combination relative to the tissue site) may have the highest ranking As described above, example devices, systems, and techniques for determining a distance between an electrode and an anatomical target are described in U.S. Patent Application Publication No. 2009/0196471 by Goetz et al., which is entitled, "CHARACTERIZATION OF ELECTRICAL STIMULATION ELECTRODES USING POST-IMPLANT IMAGING" and published on Aug. 6, 2009.

In some examples in which processor 80 ranks the therapy programs based on both the bioelectrical brain signals associated with the therapy programs and the physiological models that indicate a characteristic of tissue proximate the electrodes, processor 80 may assign different weights to a ranking based on the bioelectrical brain signals and the physiological model in order to order the therapy programs. For example, processor 80 may determine that the ranking of therapy programs based on a physiological model is entitled to more weight than the ranking determined based on bioelectrical brain signals because the physiological model may be more revealing of side effects resulting from stimulation according to a particular therapy program. Processor 80 may then rank therapy programs based on a combined score that considers both the ranking based on the bioelectrical brain signals and the ranking based on the physiological model, whereby in the combined score applies a higher weight (e.g., 51%-99%) to the ranking based on the physiological model compared to the weight (e.g., 1%-49%) applied to the ranking based on the bioelectrical brain signal. However, in other examples, processor 80 may determine that the ranking of therapy programs based bioelectrical brain signals is entitled to more weight than the ranking of therapy programs based on a physiological model.

In some examples in which processor 80 ranks the therapy programs based on both the bioelectrical brain signals associated with the therapy programs and the physiological models that indicate a characteristic of tissue proximate the electrodes, processor 80 may first rank the therapy programs based on the characteristics of the bioelectrical brain signals and then determine whether the therapy programs stimulate tissue associated with a stimulation-induced side effect or a target tissue site based on the physiological model, e.g., as described with respect to FIG. 8. If a physiological model indicates a particular therapy program programs stimulate tissue associated with a stimulation-induced side effect or a target tissue site, processor 80 may decrease the ranking of the therapy program, despite the characteristic (e.g., a frequency domain characteristic) of the bioelectrical brain signal indicating the electrodes of the therapy program are proximate the target tissue site.

In some examples in which processor 80 ranks the therapy programs based on both the bioelectrical brain signals associated with the therapy programs and the physiological models that indicate a characteristic of tissue proximate the electrodes, processor 80 may first rank the therapy programs based on whether the physiological model indicates the electrodes are proximate the target tissue site or the tissue site associated with a stimulation-induced side effect and then determine whether a characteristic of the bioelectrical brain signal indicates the electrodes of the therapy program are proximate the target tissue site, e.g., as described with respect to FIG. 9. If the bioelectrical brain signal characteristic indicates a particular therapy program is not proximate a target tissue site, e.g., because the power level within a particular band differs from a target power level by a threshold amount, processor 80 may decrease the ranking of the therapy program, despite the physiological model indicating the electrodes of the therapy program are proximate the target tissue site.

In other examples, processor 80 may order the therapy programs based on a percentage overlap of a therapy field model with physiologically significant location within brain 28. The physiologically significant location can be, for example, a target tissue site or the tissue site associated with stimulation-induced side effects. For each therapy program, processor 80 may generate a therapy field model, e.g., using the technique described above with respect to FIG. 7. As discussed with respect to FIG. 7, the therapy field model may indicate where an electrical field will propagate from the implanted lead when IMD 16 generates therapy according to the stimulation parameter values of the therapy program and delivers the therapy to brain 28 via the electrodes of the electrode combination of the therapy program. After determining the size, location, and other characteristics of the therapy field model, processor 80 can determine whether the therapy field overlaps with the physiologically significant location within brain 28. For example, if the therapy field model and the physiologically significant location are associated with a common coordinate system, processor 80 may determine whether the coordinates indicate an overlap between the therapy field model and the physiologically significant location. Other techniques are contemplated.

In some examples, processor 80 orders the therapy program having the relatively highest percentage overlap with the target tissue site as the highest-ranking therapy program. In other examples, processor 80 orders the therapy program having the relatively lowest percentage overlap with the tissue site associated with stimulation-induced side effects as the highest-ranking therapy program. In addition, in some examples, processor orders the therapy programs based on a combined score of the percentage overlap with the target tissue site and the percentage overlap with the tissue site associated with stimulation-induced side effects.

In some examples, processor 80 may generate a confidence score that assigns a numerical value to the ranking. In the example shown in FIG. 19I, ranking 440 of therapy programs includes a confidence score that indicates the percentage overlap between the therapy field model and the target tissue site. Other types of confidence scores are contemplated.

In some examples, processor 80 may order the therapy programs based on a user-provided criteria. For example, GUI 430 may include a menu with which the user can select the criteria with which processor 80 orders the therapy programs. The menu can include, for example, options for ordering the therapy programs based the proximity of the electrodes of the therapy program to the target tissue site or tissue site associated with stimulation-induced side effects as indicated by a bioelectrical brain signal sensed via the electrodes, the proximity of electrodes to the target tissue site or tissue site associated with stimulation-induced side effects as indicated by a physiological model, proximity of electrodes to the target tissue site or tissue site associated with stimulation-induced side effects as indicated by both the bioelectrical brain signals and physiological models associated with the therapy program, and/or the therapy field that may result from therapy delivery according to each therapy program.

GUI 430 shown in FIG. 19I may also include select buttons 442 associated with a respective therapy program. Upon receiving user input selecting button 442 (e.g., using the techniques described above with respect to selecting an object displayed within GUI 430), processor 80 may store the selected therapy program within memory 82 or a memory of another device, such as a remote database. In some examples, processor 80 also transmits the selected therapy programs to IMD 16 via the respective telemetry modules 86, 50, and processor 50 of IMD 16 may store the program in memory for controlling therapy delivery to patient 12. In other examples, GUI 430 may not include buttons 442, but, instead, each therapy program listed in ranking list 440 can be associated with an alphanumeric identifier (e.g., a number or letter) or a symbol, and the user can select a therapy program from ranking list 440 by inputting the associated alphanumeric identifier or symbol into a text box using a keyboard or keypad of user interface 84 (FIG. 4) of programmer 14.

In some examples, processor 80 of programmer 14 selects at least some of the therapy programs included in list 440 based on information stored by memory 82 or another memory (e.g., a remote database). Processor 80 may query memory 82 (or memory of another device) and suggest therapy programs including stimulation electrodes from array of implanted electrodes 24, 26 and stimulation parameter values based on therapy outcomes in other patients that have the same or similar condition as patient 12. The user may interact with GUI 430, as well as the other GUIs described herein, to determine whether the suggested therapy programs may provide efficacious therapy to patient 12. For example, the user may determine the bioelectrical brain signals sensed via the electrodes of each of the therapy programs and view a physiological model that indicates a therapy field that results from therapy delivery via the selected therapy program in order to determine whether the therapy program may achieve stimulation of the target tissue site and avoid stimulating a tissue site associated with a stimulation-induced side effect.

Figures 19J, 19K:
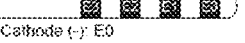

FIG. 19J is a screen diagram that illustrates an example GUI 450 displayed by processor 80 via a display of user interface 84 of programmer 14 upon receiving user input selecting history tab 286. GUI 450 is similar to GUI 304 shown in FIG. 19C, and provides a summary of the history of patient 12 as it pertains to IMD 16 and programming of IMD 16 to the extent programmer 14 has such information stored. As with GUI 304, GUI 450 indicates the patient name 306, and summarizes information relating to patient 12, such as the model of IMD 16 and leads 20 implanted in patient 12, the location of the leads, the impedance of one or more electrodes 24, 26 of leads 20, the battery status (e.g., an estimate of the remaining battery life), the active electrodes 24, 26 from which one or more simulation electrodes can be selected, and the therapy programs currently selected for patient 12. GUI 450 may differ from GUI 304 in that GUI 450 summarizes information acquired since GUI 304 was displayed, such as new therapy programs that were selected and/or generated during the current programming session.

FIG. 19K is a screen diagram that illustrates an example GUI 452 displayed by processor 80 via a display of user interface 84 of programmer 14 upon receiving user input selecting report tab 288. GUI 452 provides options with which a user can generate reports relating to therapy delivery by IMD 16 to patient 12. Processor 80 can provide the user with different report formats, such as graphs and pie charts, and, in some examples, processor 80 can present screens with which the user can manipulate the data in different manners (e.g., to generate different statistics about therapy delivery by IMD 16, such as the percentage of time IMD 16 delivered therapy according to a particular therapy program).

In the example shown in FIG. 19K, GUI 452 includes date range menu 454 for selecting the range of dates for which the one or more reports are generated, menu 456 for selecting the type of information for which one or more reports are generated, patient selection menus 458 for selecting the one or more patients for which the report is generated, report screen 459 which illustrates a report accessed and, in some examples, generated by processor 80, menu 460 for selecting the type of plot (e.g., a line plot, a bar graph, a histogram, and the like) displayed within report screen 459, menu 462 for selecting the type of statistics (if relevant) displayed by report screen 459, and menu 464 for selecting the signal characteristics of a signal displayed within report screen 459. The type of signal characteristic may be relevant if, for example, a bioelectrical brain signal is displayed within report screen 459. Processor 80 can filter the portions of the bioelectrical signal (or other physiological signal) displayed within report screen 459 based on the type of signal characteristic selected by the user via menu 464.

In the example shown in FIG. 19K, date range menu 454 enables a user to select the current date, the date range since a previous follow-up session with patient 12, or a user-specified date range. Processor 80 may utilize the date range selected via menu 454 to filter data displayed within report screen 459.

Menu 456 includes a plurality of boxes with which the user can select the type of information illustrated by the one or more reports displayed in report screen 459. In the example shown in FIG. 19K, menu 456 includes stimulation parameters, impedance of electrical paths including electrodes 24, 26, which may indicate lead integrity, battery status, different physiological signals (e.g., bioelectrical brain signals), UPDRS scores, medication taken by patient 12, and different physiological models. Other types of information may also be plotted, including user-defined fields, or other fields used as input, for example side effects or clinical benefits as a function of stimulation parameters for one or more electrodes. Upon receiving user input selecting a type of stimulation parameter from menu 456, processor 80 may generate any suitable report that provides the requested information to the user. For example, processor 80 may generate a plot that illustrates the mean, median, peak or lowest value of the stimulation delivered by IMD 16 to patient 12 over time or a plot illustrating the electrodes with which IMD 16 delivered stimulation to patient 12 over time. In the example shown in FIG. 19K, report screen 459 includes a plot that illustrates the average amplitude of stimulation delivered by IMD 16 to patient 12 over at time range from Mar. 5, 2006 to Jul. 7, 2010 (e.g., the user-specified date range selected via menu 454).

Upon receiving user input selecting impedance or battery status from menu 456, processor 80 can generate similar reports that provide the requested information to the user. For example, with respect to impedance, the report can illustrate the impedance of an electrical path including a particular electrode 24, 26 over time. With respect to battery status, the report can illustrate the power level of power source 58 of IMD 16 over time or the average consumption of power of IMD 16 over time.

Upon receiving user input selecting physiology from menu 456, processor 80 can generate a report that illustrates a signal indicative of a physiological parameter of patient 12, which may be a signal generated by sensing module 46 (FIG. 2) of IMD 16. In the example shown in FIG. 19K, the physiological information from which the user can select includes the bioelectrical brain signals sensed by sensing module 46 with different subsets of electrodes 24, 26. In some examples, the physiological signal information can include graphs 346, 348 shown in FIG. 19E or the like for some or all of electrodes 24, 26.

Upon receiving user input selecting physiological models from menu 456, processor 80 can generate a report that illustrates a physiological model that indicates one or more characteristics of tissue proximate some or all of the implanted electrodes 24, 26. The physiological models may include, for example, a graphical representation of tissue (e.g., graphical representation of tissue 372 (shown in FIG. 19F) or 3D graphical representation of tissue 423 (shown in FIG. 19H), a graphical representation of lead (e.g., graphical representation of lead 424 shown in FIG. 19H), and/or a therapy field model (e.g., activation field model 407 shown in FIGS. 19F-19H).

Upon receiving user input selecting UPDRS score from menu 456, processor 80 can generate a report that illustrates the UPDRS score of patient 12 over time. In examples in which IMD 16 delivers therapy to patient 12 to manage a condition other than Parkinson's disease, menu 456 may not include UPDRS score. Upon receiving user input selecting medication from menu 456, processor 80 can generate a report that illustrates the medication taken by patient 12 over time, which can provide the user with information to ascertain why or how a patient condition may have changed or is progressing.

Upon receiving user input selecting import/export tab 290, processor 80 can import data from another device, such as IMD 16 or a remote database, via telemetry module 86 which can store information about patient 12 (e.g., the patient condition, the type of IMD 16 and leads 20 implanted in patient 12, and so forth). In addition to or instead of importing information from another device, upon receiving user input selecting import/export tab 290, processor 80 can export data to another device (e.g., IMD 16, a remote or local computing device, or a printer) via telemetry module 86. The data can include, for example, one or more therapy parameter values or stimulation electrodes selected during the programming session. Programmer 14 can also include a help option, whereby a user can input a question and processor 80 can search a database for an answer. To access this feature of programmer 14, a user can select help tab 292.

Figure 19L:
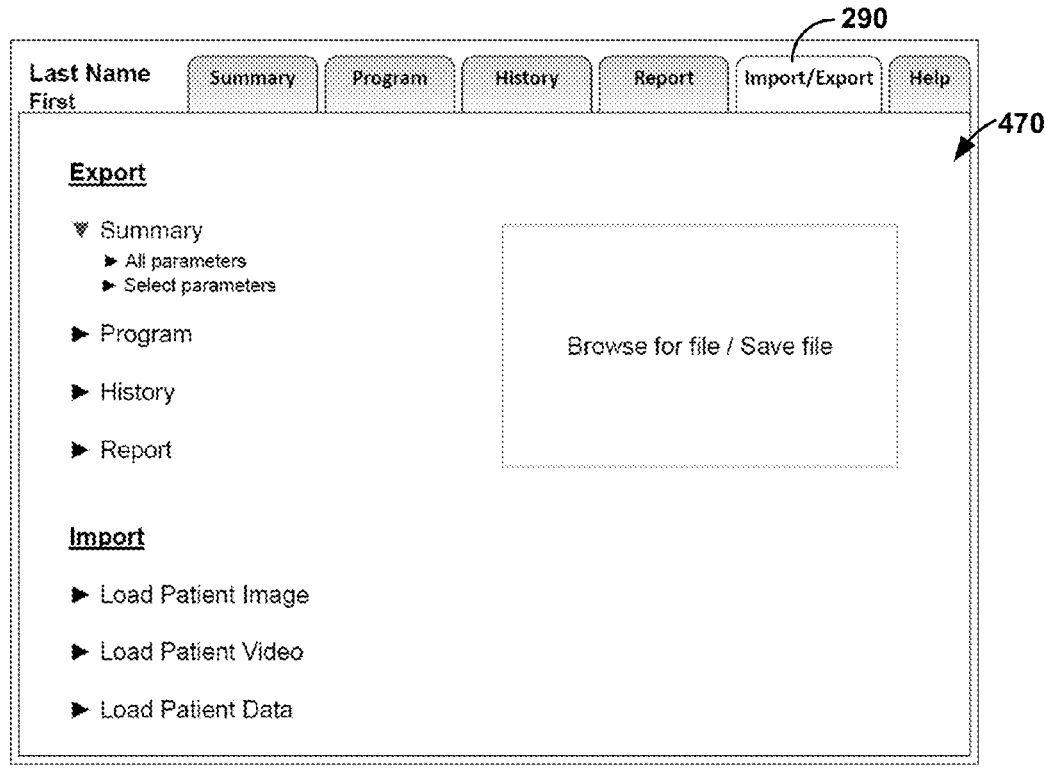

FIG. 19L is a screen diagram that illustrates an example GUI 470 displayed by processor 80 via a display of user interface 84 of programmer 14 upon receiving user input selecting export/import tab 290. Upon receiving user input selecting import/export tab 290, processor 80 can generate GUI 470, with which the user can interact to select the type of information exported to another device (e.g., IMD 16 or a remote computing device or database), or the type of information imported to programmer 14. In the example shown in FIG. 19L, the type of information that the user can select to export to another device includes the therapy programs selected by processor 80 or a user, the information generated or displayed by processor 80 under program tab 284, the patient history (e.g., the information displayed via history tab 286), various reports generated by processor (e.g., the reports displayed via report tab 288). However, GUI 470 may provide an interface with which a user may interact to export other types of information to another device in other examples.

In the example shown in FIG. 19L, the type of information that the user can select to import from another device includes medical images of patient 12 (e.g., images of brain 28 of patient 12), video of patient 12, or other patient data. However, GUI 470 may provide an interface with which a user may interact to import other types of information to programmer 14 in other examples.

Figure 19M:
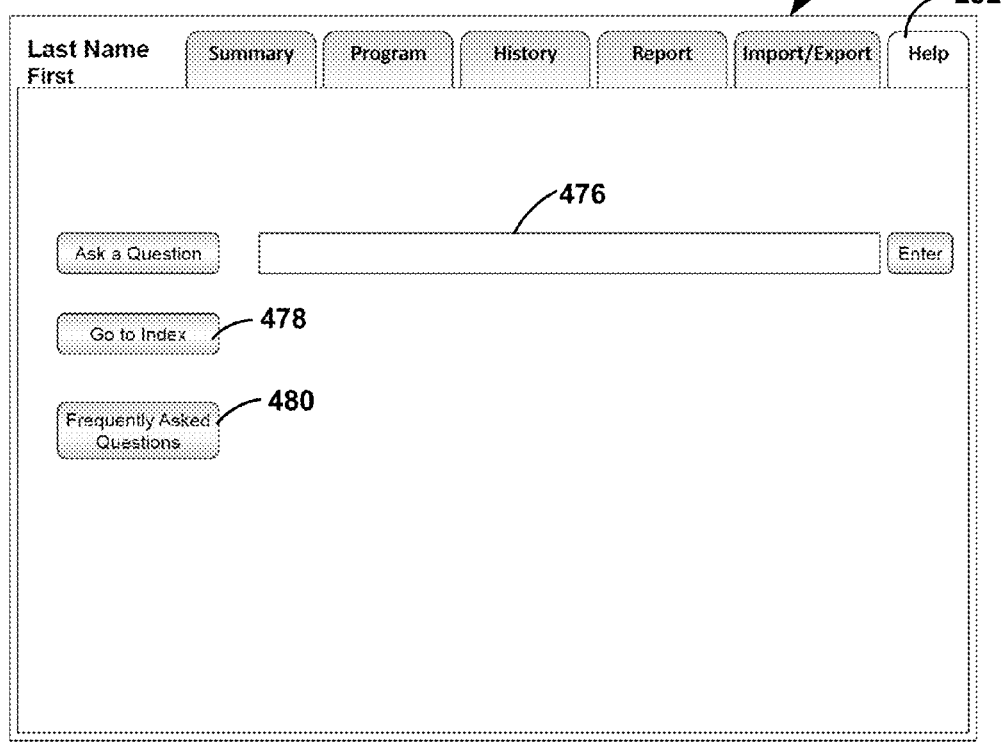

FIG. 19M is a screen diagram that illustrates an example GUI 472 displayed by processor 80 via a display of user interface 84 of programmer 14 upon receiving user input selecting help tab 292. GUI 472 includes text box 476 for receiving a question, index 478 of help topics, and list of frequently asked questions and respective answers 480. Upon receiving user input in text box 476, processor 80 can search memory 82 (FIG. 4) of programmer 14 for an answer to the question or a memory of a remote database. Processor 80 can, for example, match keywords entered into text box 476 with key words stored by memory 82 to select an answer to display to patient 12.

The devices, systems, and techniques described with respect to FIGS. 1-19M refer to selecting a stimulation electrode combination based on a bioelectrical brain signal sensed via electrodes of one or more implanted leads and a physiological model that indicates one or more anatomical structures of brain 28 of patient 12 that are proximate to the one or more implanted leads. In other examples, the devices, systems, and techniques described with respect to FIGS.

1-19M can also be used to select a stimulation electrode combination from a plurality of electrodes on a housing of a medical device (e.g., a leadless electrical stimulator can include one or more electrodes on an outer surface of the housing). Thus, the devices, systems, and techniques described with respect to FIGS. 1-19M can be used to select a stimulation electrode combination for efficacious therapy delivery to patient 12 based on a bioelectrical brain signal sensed via one or more electrodes, regardless of the member to which the electrodes are coupled, and a physiological model that indicates one or more anatomical structures of brain 28 of patient 12 that are proximate to the one or more electrodes.

In addition, in other examples, the devices, systems, and techniques described with respect to FIGS. 1-19M can also be used to select a stimulation electrode combination for efficacious therapy delivery to patient 12 based on a bioelectrical brain signal sensed via a probe and a physiological model that indicates one or more anatomical structures of brain 28 of patient 12 that are proximate to the probe.

The probe can be, for example, an apparatus that includes electrical contacts in a similar configuration as the one or more leads that the clinician anticipates implanting within brain 28 of patient 12. A clinician may position the probe within brain 28 of patient 12 in order to locate the target tissue site or locate a tissue site related to stimulation-induced side effects. For example, the clinician can position the probe within brain 28, sense a bioelectrical signal via one or more of the electrical contacts, and identify an approximate location within brain 28 based on a signal characteristic of the sensed bioelectrical brain signal. Different regions of brain 28 can be associated with respective bioelectrical brain signal characteristics. The signal characteristics can be similar to those discussed above with respect to determining whether a sensed bioelectrical brain signal indicates electrodes used to sense the bioelectrical brain signal are proximate a target tissue site or proximate a tissue site related to stimulation-induced side effects.

The probe and its contacts can be used as surrogates for leads 20. For example, any of the techniques described above for selecting a stimulation electrode combination can be utilized to select one or more electrical contacts of the probe that are proximate a target tissue site and/or distanced from a tissue site related to stimulation-induced side effects. The stimulation electrode combination can then be selected based on the selected electrical contacts of the probe. For example, electrodes that directly correspond to the selected electrical contacts based on placement on the lead and probe, respectively, can be selected as the stimulation electrodes. As another example, processor 80 of programmer 14 or another computing device or a clinician can determine the coordinates (e.g., stereotactic coordinates or other three-dimensional (3D) coordinates) of the selected electrical contacts, and, after leads 20 are implanted within brain 28, the electrodes that are at approximately the same coordinates as the selected electrical contacts can be selected as the stimulation electrodes.

Leads 20 can be implanted within brain 28 of patient based on the coordinates of the probe. For example, after finding the target tissue site within brain 28 with the probe, the clinician or programmer 14 can determine the coordinates of one or more portions of the probe (e.g., the distal tip, each contact, and the like) and the clinician can implant leads 20 such that the corresponding portions (e.g., the distal tips of the leads, the electrode locations, etc.) are implanted at substantially the same coordinates.

It may be useful to utilize the probe and its contacts as surrogates for leads 20 because the probe may be easier to manipulate (e.g., because of its rigidity or other mechanical features). In some examples, the probe may be smaller than leads 20, such that the probe may be used as a less invasive apparatus for locating target tissue site compared to implanting leads 20 within brain 28 without the prior use of the probe.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 80 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the invention have been described. These and other examples are within the scope of the following claims.

The invention claimed is:

1. A method comprising:
sensing a plurality of bioelectrical signals in a brain of a patient with respective sense electrode combinations that each comprise at least one electrode;
selecting one of the sense electrode combinations based on a signal characteristic of each of the sensed bioelectrical signals, the signal characteristic indicating a location of the at least one electrode of the respective sense electrode combination relative to a target tissue site;

accessing a physiological model that indicates one or more characteristics of tissue proximate the at least one electrode within the brain of the patient; and selecting, based on the signal characteristic of the bioelectrical signal sensed with the selected sense electrode combination and the physiological model, a stimulation electrode combination for delivering electrical stimulation to the brain of the patient.

2. The method of claim 1, wherein the physiological model comprises at least one of an electrical field model that indicates where electrical stimulation propagates from the selected stimulation electrode combination, an activation field model that indicates neurons of the brain of the patient that will be activated by the electrical stimulation delivered by the selected stimulation electrode combination, or a voltage gradient or current density model that indicates a distribution of the electrical stimulation delivered via the selected stimulation electrode combination.

3. The method of claim 1, wherein the physiological model indicates one or more anatomical structures of the brain of the patient proximate the at least one electrode within the brain of the patient.

4. The method of claim 1, wherein accessing the physiological model compromises:
generating the physiological model, wherein generating the physiological model compromises:
determining a stereotactic coordinate of a lead comprising the at least one electrode within the brain of the patient;
determining one or more anatomical structures of the brain of the patient proximate the lead based on the stereotactic coordinate; and
generating the physiological model that indicates the one or more anatomical structures of the brain of the patient proximate the lead.

5. The method of claim 1, wherein selecting one of the sense electrode combinations based on the sensed bioelectrical signals comprises:
determining a frequency domain characteristic for each bioelectrical signal of the plurality of bioelectrical signals, the signal characteristic comprising the frequency domain characteristic;
determining a plurality of relative values of the frequency domain characteristic, wherein each relative value of the plurality of relative values is based on at least two of the frequency domain characteristics; and
selecting at least one electrode of the plurality of electrodes for delivering stimulation to the patient based on the plurality of relative values.

6. The method of claim 1, wherein selecting one of the sense electrode combinations based on the sensed bioelectrical signals comprises:
comparing a pattern of the each of the sensed bioelectrical signals to a template, the signal characteristic comprising the pattern; and
selecting one or more sense electrode combinations that correspond to sensed bioelectrical signals that substantially match the template.

7. The method of claim 1, wherein selecting one of the sense electrode combinations comprises selecting the sense electrode combination based on a variability of the respective sensed bioelectrical signal, the signal characteristic comprising the variability.

8. The method of claim 1, wherein selecting one of the sense electrode combinations comprises:
determining at least one of a mean, median, peak or lowest amplitude of each of the sensed bioelectrical signals, the signal characteristic comprising the at least one of the mean, median, peak or lowest amplitude; and
selecting the sense electrode combination based on the mean, median, peak or lowest amplitude of the respective sensed bioelectrical signal.

9. The method of claim 1, wherein the physiological model comprises a therapy field model that indicates where stimulation will propagate from electrodes of the stimulation electrode combination, and wherein selecting the stimulation electrode combination comprises:
determining whether the therapy field at least partially overlaps with a target anatomical structure of the brain of the patient or one or more anatomical structures of the brain associated with stimulation-induced side effects; and
selecting the sense electrode combination as the stimulation electrode combination in response to determining the therapy field at least one of at least partially overlaps with a target anatomical structure of the brain of the patient or does not overlap with the one or more anatomical structures of the brain associated with stimulation-induced side effects.

10. The method of claim 1, further comprising displaying the physiological model via a display of a device, and wherein selecting the stimulation electrode combination comprises, after displaying the physiological model, receiving user input selecting the stimulation electrode combination.

11. The method of claim 1, wherein the physiological model indicates one or more characteristics of tissue proximate electrodes of the sense electrode combination, the method further comprising displaying the physiological model via a display of a device, wherein selecting the stimulation electrode combination comprises, after displaying the physiological model, receiving user input selecting the sense electrode combination as the stimulation electrode combination.

12. A method comprising:
sensing a bioelectrical signal in a brain of a patient with a sense electrode combination that comprises at least one electrode;
accessing a physiological model that indicates one or more characteristics of tissue proximate the at least one electrode within the brain of the patient;
selecting, based on a signal characteristic of the bioelectrical signal, a stimulation electrode combination for delivering electrical stimulation to the brain of the patient, the signal characteristic indicating a location of the at least one electrode relative to a target tissue site; and
confirming the stimulation electrode combination based on the physiological model.

13. The method of claim 12, wherein confirming the stimulation electrode combination based on the physiological model comprises determining whether the electrical stimulation delivered to the brain of the patient via the stimulation electrode combination at least one of stimulates tissue in a target anatomical structure of the brain of the patient or stimulates one or more anatomical structures of the brain associated with stimulation-induced side effects.

14. The method of claim 13, wherein the physiological model comprises a therapy field model that indicates where stimulation will propagate from electrodes of the stimulation electrode combination, and wherein determining whether the electrical stimulation delivered to the brain of the patient via the stimulation electrode combination at least one of stimulates tissue in the target anatomical structure of the brain of the patient or stimulates one or more anatomical structures of the brain associated with stimulation-induced side effects comprises determining whether the therapy field at least partially overlaps with the target anatomical structure or the one or more anatomical structures of the brain associated with stimulation-induced side effects.

15. A method comprising:
sensing a plurality of bioelectrical signals in a brain of a patient with respective sense electrode combinations that each comprise at least one electrode;
selecting one of the sense electrode combinations based on a signal characteristic of each of the sensed bioelectrical signals, the signal characteristic indicating a location of the at least one electrode of the respective sense electrode combination relative to a target tissue site;
accessing a physiological model that indicates one or more characteristics of tissue proximate the at least one electrode within the brain of the patient;
selecting, based on the physiological model, a stimulation electrode combination for delivering electrical stimulation to the brain of the patient; and
confirming the selected stimulation electrode combination based on the signal characteristic of the bioelectrical signal sensed with the selected sense electrode combination.

16. The method of claim 15, wherein confirming the selected stimulation electrode combination based on the bioelectrical signal comprises:
sensing the bioelectrical signal in the brain of the patient with the stimulation electrode combination selected based on the physiological model; and
determining whether the bioelectrical signal sensed via the stimulation electrode combination indicates the stimulation electrode combination is proximate a target stimulation site within the brain of the patient.

17. A system comprising:
a sensing module configured to sense a plurality of bioelectrical signals in a brain of a patient with respective sense electrode combinations that each comprise at least one electrode; and
a processor configured to select one of the sense electrode combinations based on a signal characteristic of each of the sensed bioelectrical signals, the signal characteristic indicating a location of the at least one electrode of the respective sense electrode combination relative to a target tissue site, access a physiological model that indicates one or more characteristics of tissue proximate the at least one electrode within the brain of the patient, and select, based on the signal characteristic of the bioelectrical signal sensed with the selected sense electrode combination and the physiological model, a stimulation electrode combination for delivering electrical stimulation to the brain of the patient.

18. The system of claim 17, wherein the physiological model comprises at least one of an electrical field model that indicates where electrical stimulation propagates from the stimulation electrode combination, an activation field model that indicates neurons of the brain of the patient that will be activated by the electrical stimulation delivered by the stimulation electrode combination, or a voltage gradient or current density model that indicates a distribution of the electrical stimulation delivered via the stimulation electrode combination.

19. The system of claim 17, wherein the physiological model indicates one or more anatomical structures of the brain of the patient proximate the at least one electrode within the brain of the patient.

20. The system of claim 17, wherein the processor is configured to generate the physiological model by at least determining a stereotactic coordinate of a lead comprising the at least one electrode within the brain of the patient and determining one or more anatomical structures of the brain of the patient proximate the lead based on the stereotactic coordinate, wherein the physiological model indicates the one or more anatomical structures of the brain of the patient proximate the at least one electrode.

21. The system of claim 17, wherein the processor is configured to select one of the sense electrode combinations based on the sensed bioelectrical signals by at least:
determining a frequency domain characteristic for each bioelectrical signal of the plurality of bioelectrical signals, the signal characteristic comprising the frequency domain characteristic;
determining a plurality of relative values of the frequency domain characteristic, wherein each relative value of the plurality of relative values is based on at least two of the frequency domain characteristics; and
selecting at least one electrode of the plurality of electrodes for delivering stimulation to the patient based on the plurality of relative values.

22. The system of claim 17, wherein the processor is configured to select one of the sense electrode combinations based on the sensed bioelectrical signals by at least:
comparing a pattern of the each of the sensed bioelectrical signals to a template, the signal characteristic comprising the pattern; and
selecting one or more sense electrode combinations that correspond to sensed bioelectrical signals that substantially match the template.

23. The system of claim 17, wherein the processor is configured to select one of the sense electrode combinations based on the sensed bioelectrical signals based on a variability of the respective sensed bioelectrical signal, the signal characteristic comprising the variability.

24. The system of claim 17, wherein the processor is configured to select one of the sense electrode combinations based on the sensed bioelectrical signals by at least:
determining at least one of a mean, median, peak or lowest amplitude of each of the sensed bioelectrical signals, the signal characteristic comprising the at least one of the mean, median, peak or lowest amplitude; and
selecting the sense electrode combination based on the mean, median, peak or lowest amplitude of the respective sensed bioelectrical signal.

25. The system of claim 17, wherein the physiological model comprises a therapy field model that indicates where stimulation will propagate from electrodes of the stimulation electrode combination, and wherein the processor is configured to select the stimulation electrode combination by at least determining whether the therapy field at least partially overlaps with a target anatomical structure of the brain of the patient or one or more anatomical structures of the brain associated with stimulation-induced side effects, and selecting the sense electrode combination as the stimulation electrode combination if the therapy field at least one of at least partially overlaps with a target anatomical structure of the brain of the patient or does not overlap with the one or more anatomical structures of the brain associated with stimulation-induced side effects.

26. The system of claim 17, further comprising a user interface comprising a display, wherein the processor is configured to display the physiological model via the display, and select the stimulation electrode combination based on user input received via the user interface after displaying the physiological model.

27. A system comprising:
a sensing module configured to sense a bioelectrical signal in a brain of a patient with a sense electrode combination that comprises at least one electrode; and
a processor configured to access a physiological model that indicates one or more characteristics of tissue proximate the at least one electrode within the brain of the patient, select, based on a signal characteristic of the bioelectrical signal, a stimulation electrode combination for delivering electrical stimulation to the brain of the patient, the signal characteristic indicating a location of the at least one electrode relative to a target tissue site, and confirm the stimulation electrode combination based on the physiological model.

28. The system of claim 27, wherein the processor is configured to confirm the stimulation electrode combination based on the physiological model by at least determining whether the electrical stimulation delivered to the brain of the patient via the stimulation electrode combination at least one of stimulates tissue in a target anatomical structure of the brain of the patient or stimulates one or more anatomical structures of the brain associated with stimulation induced side effects.

29. A system comprising:
a sensing module configured to sense a plurality of bioelectrical signals in a brain of a patient with respective sense electrode combinations that each comprise at least one electrode; and
a processor configured to select one of the sense electrode combinations based on a signal characteristic of each of the sensed bioelectrical signals, the signal characteristic indicating a location of the at least one electrode of the respective sense electrode combination relative to a target tissue site, access a physiological model that indicates one or more characteristics of tissue proximate the at least one electrode within the brain of the patient, select, based on the physiological model, a stimulation electrode combination for delivering electrical stimulation to the brain of the patient, and confirm the selected stimulation electrode combination based on the signal characteristic of the bioelectrical signal sensed with the selected sense electrode combination.

30. The system of claim 29, wherein the processor is configured to confirm the selected stimulation electrode combination based on the bioelectrical signal by at least controlling the sensing module to sense the bioelectrical signal in the brain of the patient with the stimulation electrode combination selected based on the physiological model, and determining whether the bioelectrical signal sensed via the stimulation electrode combination indicates the stimulation electrode combination is proximate a target stimulation site within the brain of the patient.

31. A system comprising:
means for sensing a plurality of bioelectrical signals in a brain of a patient with respective sense electrode combinations that each comprise at least one electrode;
means for selecting one of the sense electrode combinations based on a signal characteristic of each of the sensed bioelectrical signals, the signal characteristic indicating a location of the at least one electrode of the respective sense electrode combination relative to a target tissue site; and
means for selecting, based on the signal characteristic of the bioelectrical signal sensed with the selected sense electrode combination and a physiological model that indicates one or more characteristics of tissue proximate the at least one electrode within the brain of the patient, a stimulation electrode combination for delivering electrical stimulation to the brain of the patient.

32. A system comprising:
means for sensing a plurality of bioelectrical signals in a brain of a patient with respective sense electrode combinations that each comprise at least one electrode;
means for selecting one of the sense electrode combinations based on a signal characteristic of each of the sensed bioelectrical signals, the signal characteristic indicating a location of the at least one electrode of the respective sense electrode combination relative to a target tissue site;
means for selecting, based on the signal characteristic of the bioelectrical signal sensed with the selected sense electrode combination, a stimulation electrode combination for delivering electrical stimulation to the brain of the patient, the signal characteristic indicating a location of the at least one electrode relative to a target tissue site; and
means for confirming the stimulation electrode combination selection based on a physiological model that indicates one or more characteristics of tissue proximate the at least one electrode within the brain of the patient, wherein the physiological model comprises a therapy field model that indicates where stimulation will propagate from electrodes of the stimulation electrode combination, and wherein the means for confirming confirms the sitmulation electrode combination by at least determining whether the therapy field at least partially overlaps with a target anatomical structure of the brain of the patient or one or more anatomical structures of the brain associated with stimulation-induced side effects.

33. A system comprising:
means for sensing a plurality of bioelectrical signals in a brain of a patient with respective sense electrode combinations that each comprise at least one electrode;
means for selecting one of the sense electrode combinations based on a signal characteristic of each of the sensed bioelectrical signals, the signal characteristic indicating a location of the at least one electrode of the respective sense electrode combination relative to a target tissue site;
means for selecting, based on a physiological model that indicates one or more characteristics of tissue proximate the at least one electrode within the brain of the patient, a electrode combination for delivering electrical stimulation to the brain of the patient; and
means for confirming the selected stimulation electrode combination based on the signal characteristic of the bioelectrical signal sensed with the selected sense electrode combination.

34. A non-transitory computer-readable medium comprising instructions that cause a programmable processor to:
receive, from a sensing module, a plurality of bioelectrical signals in a brain of a patient with respective sense electrode combinations that each comprise at least one electrode;
select one of the sense electrode combinations based on a signal characteristic of each of the sensed bioelectrical signals, the signal characteristic indicating a location of the at least one electrode of the respective sense electrode combination relative to a target tissue site;

access a physiological model that indicates one or more characteristics of tissue proximate the at least one electrode within the brain of the patient; and select, based on the signal characteristic of the bioelectrical signal sensed with the selected sense electrode combination and the physiological model, a stimulation electrode combination for delivering electrical stimulation to the brain of the patient.

* * * * *